US010662433B2

(12) United States Patent
Coleman et al.

(10) Patent No.: US 10,662,433 B2
(45) Date of Patent: May 26, 2020

(54) METHOD FOR PRODUCTION OF RECOMBINANT *E. COLI* ASPARAGINASE

(71) Applicant: Pfenex Inc., San Diego, CA (US)

(72) Inventors: Russell J. Coleman, San Diego, CA (US); Torben Bruck, Lakeside, CA (US)

(73) Assignee: Pfenex Inc., San Diego, CA (US)

( * ) Notice: Subject to any disclaimer, the term of this patent is extended or adjusted under 35 U.S.C. 154(b) by 0 days.

(21) Appl. No.: 16/163,398

(22) Filed: Oct. 17, 2018

(65) Prior Publication Data
US 2019/0127743 A1 May 2, 2019

Related U.S. Application Data

(60) Provisional application No. 62/578,302, filed on Oct. 27, 2017.

(51) Int. Cl.
| *C12N 15/78* | (2006.01) |
| *C12N 9/82* | (2006.01) |
| *C12N 15/67* | (2006.01) |
| *C12R 1/39* | (2006.01) |

(52) U.S. Cl.
CPC .............. *C12N 15/78* (2013.01); *C12N 9/82* (2013.01); *C12N 15/67* (2013.01); *C12Y 305/01001* (2013.01); *C12R 1/39* (2013.01)

(58) Field of Classification Search
CPC ..................................................... C12N 15/63
See application file for complete search history.

(56) References Cited

U.S. PATENT DOCUMENTS

| 7,807,436 | B2 | 10/2010 | Filpula et al. | |
| 2008/0193974 | A1 | 8/2008 | Coleman et al. | |
| 2010/0273236 | A1* | 10/2010 | Filpula ................. | C12N 9/96 435/229 |
| 2011/0020868 | A1* | 1/2011 | Coleman .............. | C12N 15/625 435/69.1 |
| 2015/0361405 | A1 | 12/2015 | Retallack et al. | |
| 2016/0060613 | A1 | 3/2016 | Abribat | |
| 2016/0159877 | A1 | 6/2016 | Retallack et al. | |
| 2016/0348085 | A1 | 12/2016 | Alves et al. | |
| 2017/0044224 | A1 | 2/2017 | Kim et al. | |

OTHER PUBLICATIONS

Einsfeldt et al.: Recombinant L-Asparaginase from Zymomonas mobilis: A Potential New Antileukemic Agent Produced in *Escherichia coli*; Plos One; 1-18 (2016).
Erwinaze: Highlights of Prescribing Information; Reference ID: 3909112; 9 pages (2016).
European Medicines Agency: Science Medicines Health; List of nationally authorised medicinal products; 2 pages (2016).
Gilbert et al.: Cloning and Expression of the Erwinia chrysanthemi Asparaginase Gene in *Escherichia coli* and Erwinia carotovora; Journal of General Microbiology, 132, 151-160 (1986).
Oncaspar: Product Information; Annex I-Annex III; Summary of Product Characteristics 1-50 (2019) http://www.ema.europa.eu.
Spectrila: Product Inforamtion; Annex I-Annex III; Summary of Product Characteristics 1-31 (2019) http://www.ema.europa.eu.
International Application No. PCT/US2018/056374 International Search Report and Written Opinion dated Jan. 11, 2019.
International Application No. PCT/US2018/056375 International Search Report and Written Opinion dated Jan. 17, 2019.
International Application No. PCT/US2018/056376 International Search Report and Written Opinion dated Feb. 19, 2019.
Gervais et al.: RADAR (Research Archive and Digital Asset Repository); Validation of a 30-year-old process for the manufacture of L-asparaginase from Erwinia Chrysanthemi; Bioprocess and Biosystems Engineering; 36(4); pp. 27 (2013).
Glazyrina et al.: High cell density cultivation and recombinant protein production with *Escherichia coli* in a rocking-motion-type bioreactor; Microbial Cell Factories; 9:42 (2010).
Huser et al.: Cloning, sequence analysis, and expression of ansB from Pseudomonas fluorescens, encoding periplasmic glutaminase/asparaginase; FEMS microbiology letters; vol. 178, No. 1, pp. 327-335 (Sep. 1, 1999).
Latifi et al.: The Cytoplasmic and Periplasmic Expression Levels and Folding of Organophosphorus Hydrolase Enzyme in *Escherichia coli*; Jundishapur J Microbiol.; 8(12);1-5 (2015).
Nakamura et al.: On the Productivity and Properties of L-Asparaginase from *Escherichia coli* A-1-3; Agr. Biol. Chem., vol. 36, No. 12, p. 2251-2253 (1972).
Roberts et al.: New Procedures for Purification of L-Asparaginase with High Yield from *Escherichia coli*; Journal of Bacteriology; vol. 95, No. 6; pp. 2117-2123 (1968).
PCTUS2018056376 PCT Invitation to Pay Additional Fees dated Dec. 18, 2018.
Genbank Acccession No. CP001836 "Dickeya zeae Ech586 chromosome, complete genome" Aug. 30, 2017: https://www.ncbi.nlm.nih.gov/nuccore/CP001836 .
GenBank Accession No. LM996150, May 9, 2015: https://www.ncbi.nlm.nih.gov/nuccore/LM996150.
UniProtKB Accession No. A0A120G5C7_PSEFL, Apr. 13, 2016: https://www.uniprot.org/uniprot/A0A120G5C7 .
UniProtKB Accession No. A0A109LCE2 "Asparaginase from Pseudomonas fluorescens" (Apr. 13, 2016) [Retrieved from the internet on Mar. 6, 2019— < https://www.uniprot.org/uniprot/A0A109LCE2].
Wink, et al.: "Comparison between Two Erwinia carotovora L-Asparaginase II Constructions: cloning, Heterologous Expression, Purification, and Kinetic Characterization" JMBT vol. 2 Issue 1 (7 pages).
Bochtler et al.: Crystal structure of heat shock locus V (Hs1V) from *Escherichia coli*; Proc. Natl. Acad. Sci. USA; vol. 94, pp. 6070-6074 (1997).
Elspar (asparaginase): Highlights of Prescribing Information; Reference ID: 3341544; 7 pages (2013).

(Continued)

*Primary Examiner* — Tekchand Saidha
(74) *Attorney, Agent, or Firm* — Wilson Sonsini Goodrich & Rosati

(57) ABSTRACT

Provided herein are methods of production of recombinant *E. coli* asparaginase. Methods herein allow production of asparaginase in Pseudomonadales host cells at high expression levels and having activity comparable to commercially available asparaginase preparations.

24 Claims, 3 Drawing Sheets
Specification includes a Sequence Listing.

(56) References Cited

OTHER PUBLICATIONS

Maita et al.: Amino Acid Sequence of L-Asparaginase from *Escherichia coli*; J. Biochem., 76, 1351-1354 (1974).
Nakamura et al.: On the Productivity and Properties of I-Asparaginase from *Escherichia coli* A-I-3; Agricultural and Biological Chemistry; 4 pages (1972).
Oncaspar (pegaspargase): Highlights of Prescribing Information; Reference ID: 3996411; 11 pages (2014).
Ramachandran et al.: Functional interactions of HsIV (ClpQ) with the ATPase HsIU (ClpY); Proc. Natl. Acad. Sci.; vol. 99, No. 11, pp. 7396-7401 (2002).
Wang et al.: Crystal Structures of the HsIVU Peptidase—ATPase Complex Reveal an ATP-Dependent Proteolysis Mechanism; Structure, vol. 9, 177-184 (2001).

\* cited by examiner

METHOD FOR PRODUCTION OF RECOMBINANT E. COLI ASPARAGINASE

CROSS-REFERENCE TO RELATED APPLICATIONS

This application claims benefit of U.S. Provisional Application No. 62/578,302, filed Oct. 27, 2017, which is incorporated herein by reference.

SEQUENCE LISTING

The instant application contains a Sequence Listing which has been submitted electronically in ASCII format and is hereby incorporated by reference in its entirety. Said ASCII copy, created on Oct. 16, 2018, is named 38194-751_201_SL.txt and is 54,846 bytes in size.

BACKGROUND OF THE INVENTION

L-asparaginase catalyses the conversion of L-asparagine to L-aspartate. L-asparaginase type II from the bacterium *E. coli* is a tetrameric high-affinity periplasmic enzyme produced with a cleavable secretion signal sequence. Also known as L-asparagine amidohydrolase, it is the active ingredient in commercially approved drug products indicated for the treatment of patients having acute lymphoblastic leukemia (ALL). For example, Elspar®, approved in the United States for ALL treatment, has as its active ingredient *E. coli* L-asparaginase type II. Oncaspar® (pegaspargase) contains L-asparaginase (L-asparagine amidohydrolase) that is covalently conjugated to monomethoxypolyethylene glycol (mPEG). Oncaspar is approved in the United States for treatment of first line ALL, as well as ALL and hypersensitivity to native *E. coli* asparaginase. *E. coli* L-asparaginase type II is also used to treat other neoplastic conditions. The *E. coli* asparaginase can be purified from a culture of *E. coli* to yield the drug substance, e.g., genetically modified *E. coli* that is deficient in native asparaginase. In some cases, it is expressed from a gene fusion with a heterologous secretion signal peptide.

Periplasmic localization of asparaginase can provide advantages in different expression systems including reduced production of inclusion bodies, reduced proteolysis and generation of an authentic protein N-terminus. Expression yields can be lower due to the limited availability of secretion pathway cofactors and/or the spatial restriction of the periplasmic space. Cytoplasmic expression of recombinant asparaginase, can generate higher yields if the bacterial host cell cytoplasmic environment presents few penalties in regards to solubility, degradation and mis-folding of the asparaginase monomer.

SUMMARY OF THE INVENTION

Provided herein are methods for producing a recombinant type II asparaginase. In some embodiments, the method comprises: culturing a Pseudomonadales host cell in a culture medium and expressing the recombinant asparaginase in the periplasm of the Pseudomonadales host cell from an expression construct comprising a nucleic acid encoding the recombinant asparaginase; wherein the recombinant asparaginase is produced in the periplasm at a yield of about 31% to about 60% TCP soluble asparaginase. In some embodiments, the soluble recombinant asparaginase is produced in the periplasm at a yield of about 10 g/L to about 38 g/L. In some embodiments, the method further comprises measuring the activity of an amount of the recombinant type II asparaginase produced, using an activity assay. In some embodiments, the nucleic acid encoding the recombinant asparaginase is optimized for expression in the host cell. In some embodiments, the asparaginase is an *Escherichia coli* L-asparaginase type II. In some embodiments, the nucleic acid encoding the recombinant asparaginase comprises a sequence at least 85% homologous to SEQ ID NO: 1 or 3. In some embodiments, the recombinant asparaginase has an amino acid sequence at least 85% homologous to SEQ ID NO: 2. In some embodiments, expression of the recombinant asparaginase is induced with addition of IPTG to the culture media. In some embodiments, the IPTG is at a concentration in the culture media of about 0.14 mM to about 0.3 mM. In some embodiments, expression of the recombinant asparaginase is induced when the Pseudomonad host cell has grown to a wet cell weight of about 0.05 g/g to about 0.4 g/g. In some embodiments, the Pseudomonadales host cell is cultured at a pH of about 5.0 to about 8.0. In some embodiments, the Pseudomonadales host cell is cultured at a temperature of about 22° C. to about 33° C. In some embodiments, the Pseudomonadales host cell is cultured in a media comprising about 3 g/L to about 8 g/L mannitol. In some embodiments, the Pseudomonadales host cell is cultured in a media comprising no mannitol. In some embodiments, the Pseudomonadales host cell is cultured in a media comprising about 0.1 mM to about 1 mM $CaCl_2$. In some embodiments, the Pseudomonadales host cell is a *Pseudomonas fluorescens* cell. In some embodiments, the Pseudomonadales host cell is deficient in the expression of one or more asparaginases. In some embodiments, the Pseudomonadales host cell is deficient in the expression of one or more native asparaginases. In some embodiments, the deficiently expressed native asparaginase is a type I asparaginase. In some embodiments, the deficiently expressed native asparaginase is a type II asparaginase. In some embodiments, the Pseudomonadales host cell is deficient in the expression of one or more proteases. In some embodiments, the Pseudomonadales host cell overexpresses one or more folding modulators. In some embodiments, the Pseudomonadales host cell is selected from at least one of: a host cell that overexpresses LepB; a host cell that overexpresses Tig; a host cell that overexpresses DsbA, DsbC, and Skp (DsbAC-Skp); a host cell that is deficient in Lon, HslUV, DegP1, DegP2, Prc, AprA, DegP2 S219A, Prc1, or AprA; a host cell that is deficient in AspG1; a host cell that is deficient in AspG2; a host cell that does not overexpress a folding modulator, and is not deficient in a protease; a host cell that does not overexpress a folding modulator, is not deficient in a protease; and is not deficient in AspG1; a host cell that does not overexpress a folding modulator, is not deficient in a protease; and is not deficient in AspG2; and a host cell that does not overexpress a folding modulator, is not deficient in a protease; and is not deficient in AspG1 or AspG2. In some embodiments, the Pseudomonadales host cell is selected from: a host cell that is deficient in Lon and HslUV; a host cell that is deficient in Lon, DegP1, DegP2, Prc, and AprA; a host cell that is deficient in Lon, DegP1, DegP2 S219A, Prc1, and AprA, and overexpresses DsbAC-Skp; a host cell that is deficient in AspG1 and/or AspG2; a host cell that is deficient in AspG1 and/or AspG2, and overexpresses Tig; a host cell that is deficient in AspG1 and/or AspG2, and overexpresses LepB; a host cell that is deficient in AspG1 and/or AspG2, and deficient in Lon and HslUV; a host cell that is deficient in AspG1 and/or AspG2, and deficient in Lon, DegP1, DegP2, Prc, and AprA; and a host cell that is deficient in AspG1 and/or AspG2, Lon, DegP1, DegP2, Prc1, and AprA, and overexpresses DsbAC-Skp. In some embodiments, the expression construct comprises a secretion leader. In some embodiments, the secretion leader is selected from the group comprising the Pseudmonadales secretion leaders AnsB, 8484, IBP-S31A, pbp, 8584, LAO, Azu, PbpA20V, CupC2, and the *Escherichia coli* K-12 AnsB secretion leader. In some embodiments, the secretion leader directs transfer of the recombinant asparaginase produced to the periplasm of the Pseudomonadales host cell. In some embodiments, the method further comprises comparing the measured activity of the recombinant type II asparaginase produced with an activity measured in the same amount of a control type II asparaginase using the same activity assay. In some embodiments, the control type II asparaginase comprises an *E. coli* type II asparaginase that has been commercially approved for use in patients. In some embodiments, the recombinant type II asparaginase produced is selected for use in patients when it has about 80% to about 120% of the activity of the control type II asparaginase. In some embodiments, the recombinant type II asparaginase produced is modified to increase half-life in patients. In some embodiments, the recombinant type II asparaginase expressed from the expression construct is a recombinant *E. coli* type II asparaginase, wherein the nucleic acid encodes the recombinant *E. coli* type II asparaginase operably linked to the *P. fluorescens* AnsB secretion leader, and wherein the recombinant *E. coli* type II asparaginase is produced in the periplasm at a yield that is about 20% to about 100% greater than that of a recombinant *P. fluorescens* type II asparaginase produced in the periplasm by the same method, wherein the *P. fluorescens* type II asparaginase is expressed from a second expression construct comprising a nucleic acid encoding the recombinant *P. fluorescens* type II asparaginase operably linked to the *P. fluorescens* AnsB secretion leader. In some embodiments, the second expression construct comprises a nucleic acid encoding the amino acid sequence set forth as SEQ ID NO: 55.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

Overview

Figure 1:
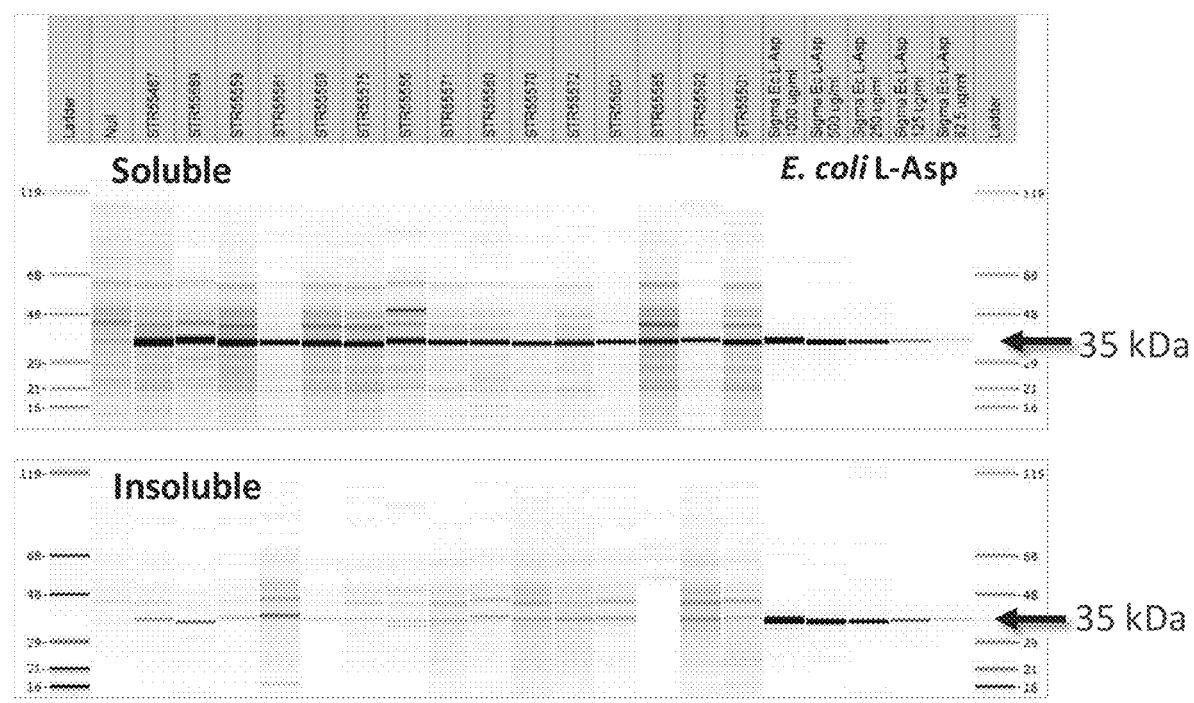
FIG. 1. SDS-CGE Gel-like Images—Tier 1 Expression Plasmid Screen. Asparaginase small scale (0.5 ml) growth whole broth sonicate soluble (upper panel) and insoluble (lower panel) were analyzed by reduced SDS-CGE. The lane at the far left shows molecular weight marker ladder (upper panel MW ladder 119 kDa, 68 KDa, 48 kDa, 29 kDa, 21 kDa, 16 kDa; lower panel MW ladder 119 kDa, 68 KDa, 48 kDa, 29 kDa, 21 kDa, 16 kDa) and the lane at the far right shows the same ladders. From left to right beginning immediately to the right of ladder 1 are lanes showing the expression patterns observed in Null, STR55467, STR55689, STR55559, STR55561, STR55569, STR55575, STR55555, STR55571, STR55560, STR55570, STR55572, STR55601, STR55585, STR55592, STR55501, and controls: Sigma *E. coli* L-Asparaginase 1000 µg/ml, Sigma *E. coli* L-Asparaginase 500 µg/ml, Sigma *E. coli* L-Asparaginase 250 µg/ml, Sigma *E. coli* L-Asparaginase 125 µg/ml, and Sigma *E. coli* L-Asparaginase 62.5 µg/ml. Arrows to the right of the gel images indicate migration of the asparaginase target protein (35 kDa).

Disclosed herein are methods for producing soluble recombinant asparaginase in a *Pseudomonas* host cell. High levels of asparaginase production as a percentage of total cell protein are described herein, for example up to 60% TCP asparaginase, e.g., asparaginase monomer, with no detectable degradation, capable of forming active tetramer. High titers of asparaginase production are obtained using the methods of the invention, for example, up to 20 grams per liter of asparaginase, e.g., asparaginase monomer, with no detectable degradation, capable of forming active tetramer. Host cells for producing asparaginase include but are not limited to *Pseudomonas*, for example *Pseudomonas fluorescens*. The asparaginase expression construct can be codon-optimized according to the selected host strain.

Nucleic acid constructs useful in the methods of the invention can encode an asparaginase gene operably linked to a nucleic acid sequence encoding a secretion signal (secretion leader), e.g., a periplasmic secretion leader native to *P. fluorescens*, resulting in expression of a secretion leader-asparaginase fusion protein. In embodiments, the host cell has a mutation in one or more protease-encoding genes, resulting in the inactivation of the protease. It is understood that a mutation resulting in inactivation of a protease or any other gene product, can be any type of mutation known in the art to cause protein inactivation or prevent protein expression including but not limited to a substitution, insertion, or deletion mutation in either the coding sequence or a regulatory sequence of the gene. It is understood that overexpression of a folding modulator can be achieved using any method known in the art, e.g., by plasmid expression or chromosomal integration of the folding modulator gene. In embodiments, the host cell has at least one protease inactivation and overexpresses at least one folding modulator.

In embodiments, the secretion leader transports soluble asparaginase to the periplasm of the host cell. In other embodiments, the asparaginase is retained in the cytoplasm. In embodiments, the asparaginase purification process does not require asparaginase solubilization and subsequent refolding. In embodiments, at least a portion of asparaginase is not expressed in inclusion bodies. In embodiments, recombinant asparaginase is expressed devoid of any peptide tag for purification and does not require additional processing upon purification. In embodiments wherein a secretion leader is fused to the asparaginase protein, the secretion leader is efficiently processed from the solubly expressed asparaginase. In other embodiments, an expression plasmid for periplasmic production of asparaginase does not utilize an antibiotic resistance marker gene for selection and maintenance, thus eliminating complicated processes for subsequent removal of plasmid DNA required for production of biopharmaceuticals. In other embodiments, fermentation conditions are scalable for large-volume production. The methods provided herein yield high levels of soluble, active asparaginase.

As known to those of skill in the art, an amino acid sequence can be encoded by different nucleotide sequences due to the redundancy in the genetic code. The present invention thus includes the use of peptides or proteins that have the same amino acid sequences but are encoded by different nucleotide sequences.

Asparaginases

Asparaginases, including type II L-asparaginases, are enzymes that catalyze the hydrolysis of L-asparagine to L-aspartate and ammonia (L-asparagine+$H_2O$=L-aspartate+$NH_3$). Type II L-asparaginases are used as part of a multi-agent chemotherapeutic regimen to treat ALL and other cancers. Certain cancer cells are unable to synthesize asparagine due to lack of asparagine synthetase, while normal cells can synthesize asparagine. Therefore, administration of the asparaginase to a patient results in hydrolysis of soluble asparagine and reduction in circulating asparagine. This can lead to death of the cancer cells with a lesser effect on normal cells. Asparaginases are described in, e.g., Pritsa and Kyriakidis, 2002, "L-Asparaginase: Structure, Properties, and Anti-Tumor Activity," in "Drug Discovery and Design: Medical Aspects," IOS Press, Matsoukas, J., and Mavromoustakos, T., eds., incorporated herein by reference.

Elspar® (Biologic License Application 101063) is an *E. coli* L-asparaginase type II product, commercially approved in the United States for treatment of ALL in patients. Its active ingredient is *E. coli* L-asparaginase type II (see Elspar® package insert, incorporated herein by reference). The active ingredient in Oncaspar® (Biologic License Application 103411) is *E. coli* L-asparaginase type II covalently conjugated to monomethoxypolyethylene glycol (mPEG) (see Oncaspar® package insert, incorporated herein by reference). Oncaspar is approved in the United States for treatment of first line ALL, as well as ALL and hypersensitivity to native *E. coli* asparaginase.

*E. coli* produces two asparaginases, L-asparaginase type I and L-asparaginase type II. L-asparaginase type I, which has a low affinity for asparagine, is located in the cytoplasm. L-asparaginase type II is a tetrameric periplasmic enzyme with a high affinity for asparagine that is produced with a cleavable secretion leader sequence. U.S. Pat. Appl. No. US 2016/0060613, "Pegylated L-asparaginase" incorporated by reference in its entirety, describes common structural features of known L-asparaginases from bacterial sources. According to US 2016/0060613, all are homotetramers with four active sites between the N- and C-terminal domains of two adjacent monomers, all have a high degree of similarity in their tertiary and quaternary structures, and the sequences of the catalytic sites of L-asparaginases are highly conserved between *Erwinia chrysanthemi, Erwinia carotovora*, and *E. coli* L-asparaginase II.

In embodiments, the *E. coli* A-1-3 L-asparaginase type II (amino acid sequence set forth in SEQ ID NO: 1 herein; SEQ ID NOS: 6-13 include secretion leader sequences) is produced using the methods of the invention. This asparaginase is described, e.g., in U.S. Pat. No. 7,807,436, "Recombinant host for producing L-asparaginase II," incorporated by reference herein in its entirety, wherein the sequence is set forth as SEQ ID NO: 1. The *E. coli* A-1-3 L-asparaginase type II also is described by Nakamura, N., et al., 1972, "On the Productivity and Properties of L-Asparaginase from *Escherichia coli* A-1-3," Agricultural and Biological Chemistry, 36:12, 2251-2253, incorporated by reference herein. *E. coli* A-1-3 is derived from the *E. coli* HAP strain, which produces high levels of asparaginse, described in Roberts, J., et al., 1968, "New Procedures for Purification of L-Asparaginase with High Yield from *Escherichia coli*," Journal of Bacteriology, 95:6, 2117-2123, incorporated by reference herein.

In embodiments, an L-asparaginase type II protein produced using the methods of the invention is the *E. coli* K-12 L-asparaginase type II enzyme, which has an amino acid sequence encoded by the ansB gene described by Jennings et al., 1990, J. Bacteriol. 172: 1491-1498 (GenBank No. M34277), both incorporated by reference herein (amino acid sequence set forth as SEQ ID NO: 3, including the native secretion leader sequence, and SEQ ID NO: 5, not including a secretion leader sequence).

U.S. Pat. No. 7,807,436 reports that, relative to the L-asparaginase type II enzyme from Merck & Co., Inc. (Elspar®) and L-asparaginase type II enzyme from Kyowa Hakko Kogyo Co., Ltd., the *E. coli* K12 enzyme subunit has $Val_{27}$ in place of $Ala_{27}$, $Asn_{64}$ in place of $Asp_{64}$, $Ser_{252}$ in place of $Thr_{252}$ and $Thr_{263}$ in place of $Asn_{263}$.

In embodiments, an L-asparaginase type II produced using the methods of the invention has an amino acid sequence set forth by Maita, T., et al, December 1974, "Amino acid sequence of L-asparaginase from *Escherichia coli*," J. Biochem. 76(6):1351-4, incorporated by reference herein.

In embodiments, an L-asparaginase type II produced using the methods of the invention is a variant of the *E. coli* A-1-3 L-asparaginase type II or the *E. coli* K-12 L-asparaginase type II enzyme, wherein the variant has about 80% to about 120%, or greater, about 85% to about 120%, about 90% to about 120%, about 95% to about 120%, about 98% to about 120%, about 100% to about 120%, about 80% to about 100%, about 80% to about 90%, about 85% to about 115%, about 90% to about 110%, about 95% to about 155%, at least about 80%, at least about 85%, at least about 90%, at least about 95%, at least about 98%, or at least about 100%, of the L-asparaginase type II activity of the *E. coli* A-1-3 L-asparaginase type II or the *E. coli* K-12 L-asparaginase type II enzyme.

In embodiments, the *E. coli* L-asparaginase type II is encoded by a nucleic acid having a sequence wherein the codons are optimized for expression in the host cell as desired.

In embodiments, a recombinant asparaginase produced using the methods of the invention is encoded by a nucleic acid sequence that is at least about 70% identical to a wild-type *E. coli* asparaginase gene. In embodiments, the recombinant asparaginase has an amino acid sequence that is at least about 70% identical to a wild type *E. coli* asparaginase. In some embodiments, a recombinant asparaginase has a nucleic acid sequence that is at least about 70%, 75%, 80%, 85%, 90%, 95%, 96%, 97%, 98%, or 99% identical to a wild type *E. coli* asparaginase nucleic acid sequence. In some embodiments, a recombinant asparaginase has an amino acid sequence that is at least about 70%, 75%, 80%, 85%, 90%, 95%, 96%, 97%, 98%, or 99% identical to a wild type *E. coli* asparaginase. "Identity" or "homology" expressed as a percentage herein describes a measure of similarity between two sequences. The extent of identity between two sequences, in some embodiments, is ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., J. Mol. Biol. 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981)).

Recombinant type II asparaginase from *E. coli* is also known by the names Colaspase®, Elspar®, Kidrolase®, Leunase®, and Spectrila®. Pegaspargase® is the name for a pegylated version of *E. coli* asparaginase. Asparaginase is administered to patients with acute lymphoblastic leukemia, acute myeloid leukemia, and non-Hodgkin's lymphoma via intravenous, intramuscular, or subcutaneous injection.

Asparaginase type II products commercially approved for patient use can be identified by accessing product information for asparaginase products available from respective countries' drug approval agencies. For example, product information and approval records are publicly available in the United States for, e.g., Elspar (*E. coli* L-asparagine amidohydrolase, type EC-2; BLA #101063) and Erwinaze® (asparaginase *Erwinia chrysanthemi*, BLA #125359) from the U.S. Food and Drug Administration and are incorporated herein by reference (10903 New Hampshire Avenue, Silver Spring, Md. 20993, and online at the FDA website). Product information in Europe is available from the European Medicines Agency (30 Churchill Place, Canary Wharf, London E14 5EU, United Kingdom, and online at the EMA website) (see, e.g., Oncaspar: EPAR product information, first published 19 Jan. 2016, relating to pegylated *E. coli* L-asparaginase; Spectrila: EPAR product information, first published 28 Jan. 2016; and List of nationally authorised medicinal products, 27 Apr. 2016, European Medicines Agency, each incorporated herein by reference).

In some embodiments, modified versions of asparaginase are generated. In general, with respect to an amino acid sequence, the term "modification" includes substitutions, insertions, elongations, deletions, and derivatizations alone or in combination. In certain embodiments, modified versions of asparaginase have enhanced properties, such as increased half-life when administered to a patient. In some embodiments, modified versions of asparaginase with increased half-life are pegylated. In some embodiments, the peptides may include one or more modifications of a "nonessential" amino acid residue. In this context, a "nonessential" amino acid residue is a residue that can be altered, e.g., deleted, substituted, or derivatized, in the novel amino acid sequence without abolishing or substantially reducing the activity (e.g., the agonist activity) of the peptide (e.g., the analog peptide). In some embodiments, the peptides may include one or more modifications of an "essential" amino acid residue. In this context, an "essential" amino acid residue is a residue that when altered, e.g., deleted, substituted, or derivatized, in the novel amino acid sequence the activity of the reference peptide is substantially reduced or abolished. In such embodiments where an essential amino acid residue is altered, the modified peptide may possess an activity of asparaginase of interest in the methods provided. The substitutions, insertions and deletions may be at the N-terminal or C-terminal end, or may be at internal portions of the protein. By way of example, the protein may include 1, 2, 3, 4, 5, 6, 7, 8, 9, 10, or more substitutions, both in a consecutive manner or spaced throughout the peptide molecule. Alone or in combination with the substitutions, the peptide may include 1, 2, 3, 4, 5, 6, 7, 8, 9, 10, or more insertions, again either in consecutive manner or spaced throughout the peptide molecule. The peptide, alone or in combination with the substitutions and/or insertions, may also include 1, 2, 3, 4, 5, 6, 7, 8, 9, 10, or more deletions, again either in consecutive manner or spaced throughout the peptide molecule. The peptide, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or unnatural. Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

Expression Systems

Methods herein, in some cases, comprise expressing recombinant asparaginase from an expression construct in a *Pseudomonas* host cell. The expression construct, in some cases, is a plasmid. In some embodiments, a plasmid encoding asparaginase sequence comprises a selection marker, and host cells maintaining the plasmid are grown under selective conditions. In some embodiments, the plasmid does not comprise a selection marker. In some embodiments, the expression construct is integrated into the host cell genome. In some embodiments, the expression construct encodes asparaginase fused to a secretion signal that directs asparaginase to the periplasm. In some embodiments, the secretion signal is cleaved in the host cell. In some embodiments, the expression construct encodes asparaginase without a secretion signal that directs the asparaginase to the cytoplasm.

Methods for expressing heterologous proteins, including regulatory sequences (e.g., promoters, secretion leaders, and ribosome binding sites) useful in the methods of the invention in host strains, including *Pseudomonas* host strains, are described, e.g., in U.S. Pat. No. 7,618,799, "Bacterial leader sequences for increased expression," in U.S. Pat. No. 7,985,564, "Expression systems with Sec-system secretion," in U.S. Pat. Nos. 9,394,571 and 9,580,719, both titled "Method for Rapidly Screening Microbial Hosts to Identify Certain Strains with Improved Yield and/or Quality in the Expression of Heterologous Proteins," U.S. Pat. No. 9,453,251, "Expression of Mammalian Proteins in *Pseudomonas fluorescens*," U.S. Pat. No. 8,603,824, "Process for Improved Protein Expression by Strain Engineering," and U.S. Pat. No. 8,530,171, "High Level Expression of Recombinant Toxin Proteins," each incorporated herein by reference in its entirety. In embodiments, a secretion leader used in the context of the present invention is a secretion leader as disclosed in any of U.S. Pat. Nos. 7,618,799, 7,985,564, 9,394,571, 9,580,719, 9,453,251, 8,603,824, and 8,530,171. These patents also describe bacterial host strains useful in practicing the methods herein, that have been engineered to overexpress folding modulators or wherein protease mutations have been introduced, in order to increase heterologous protein expression.

In embodiments, an expression strain used in the methods of the invention is any expression strain described in Example 3, as listed in Table 11. In embodiments, an expression strain used in the methods of the invention is a microbial expression strain having a background phenotype of an expression strain described in Example 3, as listed in Table 11. In embodiments, an expression strain used in the methods of the invention is a microbial expression strain having a background phenotype of an expression strain described in Example 3, as listed in Table 11, and wherein the strain expresses the recombinant asparaginase in a fusion with the respective secretion leader as listed in Table 11. In embodiments, an expression strain used in the methods of the invention is a microbial expression strain having a background phenotype of expression strain STR57864, STR57865, STR57866, STR57860, STR57861, STR57862, STR57863 described in Example 3, as listed in Table 11, except that the expression strain is not a folding modulator overexpressor. In embodiments, an expression strain used in the methods of the invention is a microbial expression strain having a background phenotype of expression strain STR57864, STR57865, STR57866, STR57860, STR57861, STR57862, STR57863 described in Example 3, as listed in Table 11, cultured without mannitol.

Promoters

The promoters used in accordance with the methods herein may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences are used to regulate expression of asparaginase in accordance with the methods herein.

In embodiments, inducible promoters useful in the methods herein include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism. In some embodiments, a lac promoter is used to regulate expression of asparaginase from a plasmid. In the case of the lac promoter derivatives or family members, e.g., the tac promoter, an inducer is IPTG (isopropyl-β-D-1-thiogalactopyranoside, also called "isopropylthiogalactoside"). In certain embodiments, IPTG is added to culture to induce expression of asparaginase from a lac promoter in a *Pseudomonas* host cell.

Common examples of non-lac-type promoters useful in expression systems according to the methods herein include, e.g., those listed in Table 1.

TABLE 1

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |
| $P_{BAD}$ | arabinose |

See, e.g.: J. Sanchez-Romero & V. De Lorenzo, 1999, Manual of Industrial Microbiology and Biotechnology (A. Demain & J. Davies, eds.) pp. 460-74 (ASM Press, Washington, D.C.); H. Schweizer, 2001, Current Opinion in Biotechnology, 12:439-445; R. Slater & R. Williams 2000, Molecular Biology and Biotechnology (J. Walker & R. Rapley, eds.) pp. 125-54 (The Royal Society of Chemistry, Cambridge, UK); and L.-M. Guzman, et al., 1995, J. Bacteriol. 177(14): 4121-4130, all incorporated by reference herein. A promoter having the nucleotide sequence of a promoter native to the selected bacterial host cell also may be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to methods herein. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although, in some cases, an effector compound is used throughout the cell culture or fermentation, in one embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lacI gene is sometimes present in the system. The lacI gene, which is normally a constitutively expressed gene, encodes the Lac repressor protein LacI protein, which binds to the lac operator of lac family promoters. Thus, where a lac family promoter is utilized, the lacI gene is sometimes also included and expressed in the expression system.

Promoter systems useful in *Pseudomonas* are described in the literature, e.g., in U.S. Pat. App. Pub. No. 2008/0269070, also referenced above.

Other Regulatory Elements

In embodiments, soluble recombinant asparaginase is present in either the cytoplasm or periplasm of the cell during production. Secretion leaders useful for targeting proteins, e.g., asparaginase, are described elsewhere herein, and in U.S. Pat. App. Pub. No. 2008/0193974, U.S. Pat. App. Pub. No. 2006/0008877, and in U.S. patent application Ser. No. 12/610,207, referenced above. In some embodiments, expression constructs are provided that encode asparaginase fused to a secretion leader that transport asparaginase to the periplasm of a *Pseudomonas* cell. In some embodiments, the secretion leader the secretion leader is cleaved from the asparaginase protein. In some embodiments, the secretion leader facilitates production of soluble asparaginase.

An expression construct useful in practicing the methods herein include, in addition to the protein coding sequence, the following regulatory elements operably linked thereto: a promoter, a ribosome binding site (RBS), a transcription terminator, and translational start and stop signals.

In embodiments, the expression vector contains an optimal ribosome binding sequence. Modulating translation strength by altering the translation initiation region of a protein of interest can be used to improve the production of heterologous cytoplasmic proteins that accumulate mainly as inclusion bodies due to a translation rate that is too rapid. Secretion of heterologous proteins into the periplasmic space of bacterial cells can also be enhanced by optimizing rather than maximizing protein translation levels such that the translation rate is in sync with the protein secretion rate.

The translation initiation region has been defined as the sequence extending immediately upstream of the ribosomal binding site (RBS) to approximately 20 nucleotides downstream of the initiation codon (McCarthy et al. (1990) Trends in Genetics 6:78-85, herein incorporated by reference in its entirety). In prokaryotes, alternative RBS sequences can be utilized to optimize translation levels of heterologous proteins by providing translation rates that are decreased with respect to the translation levels using the canonical, or consensus, RBS sequence (AGGAGG; SEQ ID NO: 45) described by Shine and Dalgarno (Proc. Natl. Acad. Sci. USA 71:1342-1346, 1974). By "translation rate" or "translation efficiency" is intended the rate of mRNA translation into proteins within cells. In most prokaryotes, the Shine-Dalgarno sequence assists with the binding and positioning of the 30S ribosome component relative to the start codon on the mRNA through interaction with a pyrimidine-rich region of the 16S ribosomal RNA. The RBS (also referred to herein as the Shine-Dalgarno sequence) is located on the mRNA downstream from the start of transcription and upstream from the start of translation, typically from 4 to 14 nucleotides upstream of the start codon, and more typically from 8 to 10 nucleotides upstream of the start codon. Because of the role of the RBS sequence in translation, there is a direct relationship between the efficiency of translation and the efficiency (or strength) of the RBS sequence.

In some embodiments, modification of the RBS sequence results in a decrease in the translation rate of the heterologous protein. This decrease in translation rate may correspond to an increase in the level of properly processed protein or polypeptide per gram of protein produced, or per gram of host protein. The decreased translation rate can also correlate with an increased level of recoverable protein or polypeptide produced per gram of recombinant or per gram of host cell protein. The decreased translation rate can also correspond to any combination of an increased expression, increased activity, increased solubility, or increased translocation (e.g., to a periplasmic compartment or secreted into the extracellular space). In this embodiment, the term "increased" is relative to the level of protein or polypeptide that is produced, properly processed, soluble, and/or recoverable when the protein or polypeptide of interest is expressed under the same conditions, or substantially the same conditions, and wherein the nucleotide sequence encoding the polypeptide comprises the canonical RBS sequence. Similarly, the term "decreased" is relative to the translation rate of the protein or polypeptide of interest wherein the gene encoding the protein or polypeptide comprises the canonical RBS sequence. The translation rate can be decreased by at least about 5%, at least about 10%, at least about 15%, at least about 20%, about 25%, about 30%, about 35%, about 40%, about 45%, about 50%, about 55%, about 60%, about 65%, about 70, at least about 75% or more, or at least about 2-fold, about 3-fold, about 4-fold, about 5-fold, about 6-fold, about 7-fold, or greater.

In some embodiments, the RBS sequence variants described herein can be classified as resulting in high, medium, or low translation efficiency. In one embodiment, the sequences are ranked according to the level of translational activity compared to translational activity of the canonical RBS sequence. A high RBS sequence has about 60% to about 100% of the activity of the canonical sequence. A medium RBS sequence has about 40% to about 60% of the activity of the canonical sequence. A low RBS sequence has less than about 40% of the activity of the canonical sequence.

Examples of RBS sequences are shown in Table 2. The sequences were screened for translational strength using COP-GFP as a reporter gene and ranked according to percentage of consensus RBS fluorescence. Each RBS variant was placed into one of three general fluorescence ranks: High ("Hi"—100% Consensus RBS fluorescence), Medium ("Med"—46-51% of Consensus RBS fluorescence), and Low ("Lo"—16-29% Consensus RBS fluorescence).

TABLE 2

RBS Sequences

| RBS | Sequence | Strength | SEQ ID NO: |
|---|---|---|---|
| Consensus | AGGAGG | High | 45 |
| RBS2 | GGAGCG | Med | 46 |
| RBS34 | GGAGCG | Med | 47 |
| RBS41 | AGGAGT | Med | 48 |
| RBS43 | GGAGTG | Med | 49 |
| RBS48 | GAGTAA | Low | 50 |
| RBS1 | AGAGAG | Low | 51 |
| RBS35 | AAGGCA | Low | 52 |
| RBS49 | CCGAAC | Low | 53 |

Useful RBSs are obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181 (3):563-70 (1989). Further examples of methods, vectors, and translation and transcription elements, and other elements useful in the methods herein are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Host Strains

Bacterial hosts, including Pseudomonads, and closely related bacterial organisms are contemplated for use in practicing the methods herein. In certain embodiments, the Pseudomonad host cell is *Pseudomonas fluorescens*. In some cases, the host cell is an *E. coli* cell.

Host cells and constructs useful in practicing the methods herein are identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lacI gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U. S. Pat. App. Pub. No. 2009/0325230, "Protein Expression Systems," and in Schneider, et al., 2005, "Auxotrophic markers pyrF and proC, in some cases, replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB101. The pyrF gene was cloned from strain MB214 (ATCC deposit PTA-7840) to generate a plasmid that complements the pyrF deletion to restore prototrophy. In particular embodiments, a pyrF proC dual auxotrophic selection marker system in a *P. fluorescens* host cell is used. A pyrF deleted production host strain as described is often used as the background for introducing other desired genomic changes, including those described herein as useful in practicing the methods herein.

In embodiments, a host cell useful in the methods of the present invention is deficient in the expression of at least one protease, overexpresses at least one folding modulator, or both. In embodiments, the host cell is not deficient in the expression of a protease and does not overexpress a folding modulator, and therefore is wild-type with respect to protease and folding modulator expression. In any of these embodiments, the host cell is additionally deficient in a native L-asparaginase. In embodiments, the deficiency in the native L-asparaginase is generated by deleting or otherwise inactivating the native L-asparaginase gene using any suitable method known in the art. In embodiments, the host cell is deficient in a native Type I L-asparaginase, a native Type II L-asparaginase, or both. In embodiments, the host cell is wild-type with respect to protease and folding modulator expression, and deficient in a native Type I L-asparaginase and a Type II L-asparaginase. For example, a host cell useful in the methods of the invention can be generated by one of skill in the art from MB101, using known methods. In embodiments, the host cell is generated by deleting or otherwise inactivating the Type I L-asparaginase gene, the Type II L-asparaginase gene, or both, in MB101.

It would be understood by one of skill in the art that a production host strain useful in the methods of the present invention can be generated using a publicly available host cell, for example, *P. fluorescens* MB101, e.g., by inactivating the pyrF gene, and/or the Type I L-asparaginase gene, and/or the Type II L-asparaginase gene, using any of many appropriate methods known in the art and described in the literature. It is also understood that a prototrophy restoring plasmid can be transformed into the strain, e.g., a plasmid carrying the pyrF gene from strain MB214 using any of many appropriate methods known in the art and described in the literature. Additionally, in such strains, proteases can be inactivated and folding modulator overexpression constructs introduced, using methods well known in the art.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*. Host cells of the order Pseudomonadales, of the family Pseudomonadaceae, or of the genus *Pseudomonas* are identifiable by one of skill in the art and are described in the literature (e.g., Bergey's Manual of Systematics of Archaea and Bacteria (online publication, 2015).

Other *Pseudomonas* organisms may also be useful. Pseudomonads and closely related species include Gram-negative Proteobacteria Subgroup 1, which include the group of Proteobacteria belonging to the families and/or genera described in Bergey's Manual of Systematics of Archaea and Bacteria (online publication, 2015). Table 3 presents these families and genera of organisms.

TABLE 3

Families and Genera Listed in the Part, "Gram-Negative Aerobic Rods and Cocci" (in Bergey's Manual of Systematics of Archaea and Bacteria (online publication, 2015))

| | |
|---|---|
| Family I. Pseudomonaceae | *Gluconobacter* |
| | *Pseudomonas* |
| | *Xanthomonas* |
| | *Zoogloea* |
| Family II. Azotobacteraceae | *Azomonas* |
| | *Azotobacter* |
| | *Beijerinckia* |
| | *Derxia* |
| Family III. Rhizobiaceae | *Agrobacterium* |
| | *Rhizobium* |
| Family IV. Methylomonadaceae | *Methylococcus* |
| | *Methylomonas* |
| Family V. Halobacteriaceae | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

*Pseudomonas* and closely related bacteria are generally part of the group defined as "Gram(−) Proteobacteria Subgroup 1" or "Gram-Negative Aerobic Rods and Cocci" (Bergey's Manual of Systematics of Archaea and Bacteria (online publication, 2015)). *Pseudomonas* host strains are described in the literature, e.g., in U.S. Pat. App. Pub. No. 2006/0040352, cited above.

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey's Manual of Systematics of Archaea and Bacteria (online publication, 2015). In addition hosts include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosterone* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus Liberibacter*"), and *Sinorhizobium;* and 4) Methylococcaceae family bacteria of the genera *Methylobacter, Methylocaldum, Methylomicrobium, Methylosarcina*, and *Methylosphaera*.

The host cell, in some cases, is selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas akaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoakaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphihla; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas*

*cichorii* (ATCC 10857); *Pseudomonas ficuserectae* (ATCC 35104); *Pseudomonas fuscovaginae*; *Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans*; *Pseudomonas thivervalensis*; *Pseudomonas vancouverensis* (ATCC 700688); *Pseudomonas wisconsinensis*; and *Pseudomonas xiamenensis*. In one embodiment, the host cell for expression of asparaginase is *Pseudomonas fluorescens*.

The host cell, in some cases, is selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans*; *Pseudomonas brenneri*; *Pseudomonas cedrella*; *Pseudomonas cedrina*; *Pseudomonas corrugata*; *Pseudomonas extremorientalis*; *Pseudomonas fluorescens*; *Pseudomonas gessardii*; *Pseudomonas libanensis*; *Pseudomonas mandelii*; *Pseudomonas marginalis*; *Pseudomonas migulae*; *Pseudomonas mucidolens*; *Pseudomonas orientalis*; *Pseudomonas rhodesiae*; *Pseudomonas synxantha*; *Pseudomonas tolaasii*; and *Pseudomonas veronii*.

Proteases

In one embodiment, the methods provided herein comprise using a *Pseudomonas* host cell, comprising one or more mutations (e.g., a partial or complete deletion) in one or more protease genes, to produce recombinant asparaginase protein. In some embodiments, a mutation in a protease gene facilitates generation of recombinant asparaginase protein.

Exemplary target protease genes include those proteases classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component c1r55, complement component c1s55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor c, limulus clotting factor, limulus clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrier-pepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases have both protease and chaperone-like activity. When these proteases are negatively affecting protein yield and/or quality it is often useful to specifically delete their protease activity, and they are overexpressed when their chaperone activity may positively affect protein yield and/or quality. These proteases include, but are not limited to: Hsp100(Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

In embodiments a host strain useful for expressing an asparaginase, e.g., an *E. coli* asparaginase type II, in the methods of the invention is a *Pseudomonas* host strain, e.g., *P. fluorescens*, having a protease deficiency or inactivation (resulting from, e.g., a deletion, partial deletion, or knockout) and/or overexpressing a folding modulator, e.g., from a plasmid or the bacterial chromosome. In embodiments, the host strain is deficient in at least one protease selected from Lon, HslUV, DegP1, DegP2, Prc, AprA, DegP2 S219A, Prc1, and AprA. In embodiments, the host strain overexpresses a folding modulator selected from LepB, Tig, and DsbAC-Skp (i.e., the combination of DsbA, DsbC and Skp; Skp is OmpH RXF4702.1, set forth as SEQ ID NO: 56 herein, with an example of a coding sequence set forth as SEQ ID NO: 57). In a DsbAC-Skp overexpressor host, folding modulators DsbA, DsbC and Skp (SEQ ID NOS: 25 and 26 of U.S. Pat. No. 9,394,571 and SEQ ID NO: 57 herein, respectively) can be expressed from an operon. In embodiments, the host strain is deficient in at least one protease selected from Lon, HslUV, DegP1, DegP2, Prc, AprA, DegP2 S219A, Prc1, and AprA, and overexpresses a folding modulator selected from LepB, Tig, and DsbAC-Skp. In any of the above embodiments, the host strain expresses the auxotrophic markers pyrF and proC, and has a protease deficiency and/or overexpresses a folding modulator. In embodiments, the host strain expresses any other suitable selection marker known in the art. In any of the above embodiments, an asparaginase, e.g., a native Type I and/or Type II asparaginase, is inactivated in the host strain. In embodiments, the host strain is a Pseudomonadales host cell is: deficient in Lon and HslUV; deficient in Lon, DegP1, DegP2, Prc, and AprA; deficient in Lon, DegP1, DegP2 S219A, Prc1, and AprA, and overexpresses DsbAC-Skp; deficient in AspG1 and/or AspG2; deficient in AspG1 and/or AspG2, and overexpresses Tig; deficient in AspG1 and/or AspG2, and overexpresses LepB; deficient in AspG1 and/or AspG2, and deficient in Lon and HslUV; a host cell that is deficient in AspG1 and/or AspG2, and deficient in Lon, DegP1, DegP2, Prc, and AprA; or a host cell that is deficient in AspG1 and/or AspG2, Lon, DegP1, DegP2, Prc1, and AprA, and overexpresses DsbAC-Skp. In a DsbAC-Skp overexpressor host, folding modulators DsbA, DsbC and Skp (SEQ ID NOS: 56 and 57 herein) can be expressed from an operon. HslUV (also referred to as HslVU) is a complex of HslV protease and HslU ATPase. HslU and V function and structure are described in the literature, e.g., by Bochtler et al., 1997, PNAS 94:6070-6074; Ramachandran et al., 2002, PNAS 99(11): 7396-7401; and Wang et al., 2001, Structure 9:177-184, each incorporated herein by reference in its entirety.

These and other proteases and folding modulators are known in the art and described in the literature, e.g., in U.S. Pat. No. 8,603,824. For example, Table D of the patent describes Tig (tig, Trigger factor, FKBP type ppiase (ec 5.2.1.8) RXF04655, UniProtKB—P0A850 (TIG_ECOLI)). WO 2008/134461, titled "Method for Rapidly Screening Microbial Hosts to Identify Certain Strains with Improved Yield and/or Quality in the Expression of Heterologous Proteins," and incorporated by reference in its entirety herein, describes Tig (RXF04655.2, SEQ ID NO: 34 therein), LepB (RXF01181.1, SEQ ID NO: 56 therein), DegP1 (RXF01250, SEQ ID NO: 57 therein), AprA (RXF04304.1, SEQ ID NO: 86 therein), Prc1 (RXF06586.1, SEQ ID NO: 120 therein), DegP2, (RXF07210.1, SEQ ID NO: 124 therein), Lon (RXF04653, SEQ ID NO: 92 therein); DsbA (RXF01002.1, SEQ ID NO: 25 therein), and DsbC (RXF03307.1, SEQ ID NO: 26 therein). These sequences and those for other proteases and folding modulators also are set forth in U.S. Pat. No. 9,580,719 (Table of SEQ ID NOS in columns 93-98 therein). For example, U.S. Pat. No. 9,580,719 provides the sequence encoding HslU (RXF01957.2) and HslV (RXF01961.2) as SEQ ID NOS 18 and 19, respectively.

Codon Optimization

In one embodiment, the methods herein comprise expression of recombinant asparaginase from a construct that has been optimized for codon usage in a strain of interest. In embodiments, the strain is a *Pseudomonas* host cell, e.g., *Pseudomonas fluorescens*. Methods for optimizing codons to improve expression in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. Methods for optimizing the nucleic acid sequence of to improve expression of a heterologous protein in a bacterial host are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Optimization addresses any of a number of sequence features of the heterologous gene. As a specific example, a rare codon-induced translational pause often results in reduced heterologous protein expression. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which sometimes results in rare host codons being removed from the synthetic polynucleotide sequence.

Alternate translational initiation also sometimes results in reduced heterologous protein expression. Alternate translational initiation includes a synthetic polynucleotide sequence inadvertently containing motifs capable of functioning as a ribosome binding site (RBS). These sites, in some cases, result in initiating translation of a truncated protein from a gene-internal site. One method of reducing the possibility of producing a truncated protein, which are often difficult to remove during purification, includes eliminating putative internal RBS sequences from an optimized polynucleotide sequence.

Repeat-induced polymerase slippage often results in reduced heterologous protein expression. Repeat-induced polymerase slippage involves nucleotide sequence repeats that have been shown to cause slippage or stuttering of DNA polymerase which sometimes results in frameshift mutations. Such repeats also often cause slippage of RNA polymerase. In an organism with a high G+C content bias, there is sometimes a higher degree of repeats composed of G or C nucleotide repeats. Therefore, one method of reducing the possibility of inducing RNA polymerase slippage, includes altering extended repeats of G or C nucleotides.

Interfering secondary structures also sometimes result in reduced heterologous protein expression. Secondary structures often sequester the RBS sequence or initiation codon and have been correlated to a reduction in protein expression. Stem loop structures are also often involved in transcriptional pausing and attenuation. An optimized polynucleotide sequence usually contains minimal secondary structures in the RBS and gene coding regions of the nucleotide sequence to allow for improved transcription and translation.

Another feature that sometimes effect heterologous protein expression is the presence of restriction sites. By removing restriction sites that could interfere with subsequent sub-cloning of transcription units into host expression vectors a polynucleotide sequence is optimized.

For example, the optimization process often begins by identifying the desired amino acid sequence to be heterologously expressed by the host. From the amino acid sequence, a candidate polynucleotide or DNA is designed. During the design of the synthetic DNA sequence, the frequency of codon usage is often compared to the codon usage of the host expression organism and rare host codons are removed from the synthetic sequence. Additionally, the synthetic candidate DNA sequence is sometimes modified in order to remove undesirable enzyme restriction sites and add or remove any desired signal sequences, linkers or untranslated regions. The synthetic DNA sequence is often analyzed for the presence of secondary structure that may interfere with the translation process, such as G/C repeats and stem-loop structures. Before the candidate DNA sequence is synthesized, the optimized sequence design is often checked to verify that the sequence correctly encodes the desired amino acid sequence. Finally, the candidate DNA sequence is synthesized using DNA synthesis techniques, such as those known in the art.

In another embodiment herein, the general codon usage in a host organism, such as *P. fluorescens*, is often utilized to optimize the expression of the heterologous polynucleotide sequence. The percentage and distribution of codons that rarely would be considered as preferred for a particular amino acid in the host expression system is evaluated. Values of 5% and 10% usage is often used as cutoff values for the determination of rare codons. For example, the codons listed in Table 4 have a calculated occurrence of less than 5% in the *P. fluorescens* MB214 genome and would be generally avoided in an optimized gene expressed in a *P. fluorescens* host.

TABLE 4

| Codons occurring at less than 5% in *P. fluorescens* MB214 | | |
|---|---|---|
| Amino Acid(s) | Codon(s) Used | % Occurrence |
| G Gly | GGA | 3.26 |
| I Ile | ATA | 3.05 |
| L Leu | CTA | 1.78 |
|  | CTT | 4.57 |
|  | TTA | 1.89 |
| R Arg | AGA | 1.39 |
|  | AGG | 2.72 |
|  | CGA | 4.99 |
| S Ser | TCT | 4.28 |

The present disclosure contemplates the use of any asparaginase coding sequence, including any sequence that has been optimized for expression in the *Pseudomonas* host cell being used. Sequences contemplated for use are often optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods provided herein is encoded by any appropriate nucleic acid sequence. Codon optimization for expression in *E. coli* is described, e.g., by Welch, et al., 2009, PLoS One, "Design Parameters to Control Synthetic Gene Expression in *Escherichia coli*," 4(9): e7002, Ghane, et al., 2008, Krishna R. et al., (2008) Mol Biotechnology "Optimization of the AT-content of Codons Immediately Downstream of the Initiation Codon and Evaluation of Culture Conditions for High-level Expression of Recombinant Human G-CSF in *Escherichia coli*," 38:221-232.

High Throughput Screens

In some embodiments, a high throughput screen is often conducted to determine optimal conditions for expressing soluble recombinant asparaginase. The conditions that be varied in the screen include, for example, the host cell, genetic background of the host cell (e.g., deletions of different proteases), type of promoter in an expression construct, type of secretion leader fused to encoded asparaginase, temperature of growth, OD of induction when an inducible promoter is used, amount of inducer added (e.g. amount of IPTG used for induction when a lacZ promoter or derivative thereof is used), duration of protein induction, temperature of growth following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" is often identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, whether the protein is sequestered or secreted, protein folding, and the like. For example, the optimal host strain or optimal expression system produces a yield, characterized by the amount of soluble heterologous protein, the amount of recoverable heterologous protein, the amount of properly processed heterologous protein, the amount of properly folded heterologous protein, the amount of active heterologous protein, and/or the total amount of heterologous protein, of a certain absolute level or a certain level relative to that produced by an indicator strain, i.e., a strain used for comparison.

Methods of screening microbial hosts to identify strains with improved yield and/or quality in the expression of heterologous proteins are described, for example, in U.S. Patent Application Publication No. 20080269070.

Bacterial Growth Conditions

Growth conditions useful in the methods herein often comprise a temperature of about 4° C. to about 42° C. and a pH of about 5.7 to about 8.8. When an expression construct with a lacZ promoter or derivative thereof is used, expression is often induced by adding IPTG to a culture at a final concentration of about 0.01 mM to about 1.0 mM.

The pH of the culture is sometimes maintained using pH buffers and methods known to those of skill in the art. Control of pH during culturing also is often achieved using aqueous ammonia. In embodiments, the pH of the culture is about 5.7 to about 8.8. In certain embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8 In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8. In yet other embodiments, the pH is about 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25.

In embodiments, the growth temperature is maintained at about 4° C. to about 42° C. In certain embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 30° C. to about 33° C., or about 32° C. to about 33° C. In other embodiments, the temperature is changed during culturing. In certain embodiments, the temperature is maintained at about 30° C. to about 32° C. before an agent to induce expression from the construct encoding the polypeptide or protein of interest is added to the culture, and the temperature is dropped to about 25° C. to about 27° C. after adding an agent to induce expression, e.g., IPTG is added to the culture. In one embodiment, the temperature is maintained at about 30° C. before an agent to induce expression from the construct encoding the polypeptide or protein of interest is added to the culture, and the temperature is dropped to about 25° C. after adding an agent to induce expression is added to the culture.

Induction

As described elsewhere herein, inducible promoters are often used in the expression construct to control expression of the recombinant asparaginase, e.g., a lac promoter. In the case of the lac promoter derivatives or family members, e.g., the tac promoter, the effector compound is an inducer, such as a gratuitous inducer like IPTG (isopropyl-β-D-1-thiogalactopyranoside, also called "isopropylthiogalactoside"). In embodiments, a lac promoter derivative is used, and asparaginase expression is induced by the addition of IPTG to a final concentration of about 0.01 mM to about 1.0 mM, when the cell density has reached a level identified by an OD575 of about 25 to about 160. In embodiments, the OD575 at the time of culture induction for asparaginase is about 25, about 50, about 55, about 60, about 65, about 70, about 80, about 90, about 100, about 110, about 120, about 130, about 140, about 150, about 160, about 170 about 180. In other embodiments, the OD575 is about 80 to about 100, about 100 to about 120, about 120 to about 140, about 140 to about 160. In other embodiments, the OD575 is about 80 to about 120, about 100 to about 140, or about 120 to about 160. In other embodiments, the OD575 is about 80 to about 140, or about 100 to 160. The cell density is often measured by other methods and expressed in other units, e.g., in cells per unit volume. For example, an OD575 of about 25 to about 160 of a *Pseudomonas fluorescens* culture is equivalent to approximately $4 \times 10^{10}$ to about $1.6 \times 10^{11}$ colony forming units per mL or 11 to 70 g/L dry cell weight. In embodiments, asparaginase expression is induced by the addition of IPTG to a final concentration of about 0.01 mM to about 1.0 mM, when the cell density has reached a wet cell weight of about 0.05 g/g to about 0.4 g/g. In embodiments the wet cell weight is about 0.05 g/g, about 0.1 g/g, about 0.15 g/g, about 0.2 g/g, about 0.25 g/g, about 0.30 g/g, about 0.35 g/g, about 0.40 g/g, about 0.05 g/g to about 0.1 g/g, about 0.05 g/g to about 0.15 g/g, about 0.05 g/g to about 0.20 g/g, about 0.05 g/g to about 0.25 g/g, about 0.05 g/g to about 0.30 g/g, about 0.05 g/g to about 0.35 g/g, about 0.1 g/g to about 0.40 g/g, about 0.15 g/g to about 0.40 g/g, about 0.20 g/g to about 0.40 g/g, about 0.25 g/g to about 0.40 g/g, about 0.30 g/g to about 0.40 g/g, or about 0.35 g/g to about 0.40 g/g. In embodiments, the cell density at the time of culture induction is equivalent to the cell density as specified herein by the absorbance at OD575, regardless of the method used for determining cell density or the units of measurement. One of skill in the art will know how to make the appropriate conversion for any cell culture.

In embodiments, the final IPTG concentration of the culture is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, or about 1 mM. In other embodiments, the final IPTG concentration of the culture is about 0.08 mM to about 0.1 mM, about 0.1 mM to about 0.2 mM, about 0.2 mM to about 0.3 mM, about 0.3 mM to about 0.4 mM, about 0.2 mM to about 0.4 mM, about 0.08 to about 0.2 mM, or about 0.1 to 1 mM.

In embodiments wherein a non-lac type promoter is used, as described herein and in the literature, other inducers or effectors are often used. In one embodiment, the promoter is a constitutive promoter.

After adding and inducing agent, cultures are often grown for a period of time, for example about 24 hours, during which time the recombinant asparaginase is expressed. After adding an inducing agent, a culture is often grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture is grown for about 1 to 48 hrs, about 1 to 24 hrs, about 10 to 24 hrs, about 15 to 24 hrs, or about 20 to 24 hrs. Cell cultures are often concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Microfluidizer, Constant Cell Disruptor, Niro-Soavi homogenizer or APV-Gaulin homogenizer). Cells expressing asparaginase are often disrupted, for example, using sonication. Any appropriate method known in the art for lysing cells are often used to release the soluble fraction. For example, in embodiments, chemical and/or enzymatic cell lysis reagents, such as cell-wall lytic enzyme and EDTA, are often used. Use of frozen or previously stored cultures is also contemplated in the methods herein. Cultures are sometimes OD-normalized prior to lysis. For example, cells are often normalized to an OD600 of about 10, about 11, about 12, about 13, about 14, about 15, about 16, about 17, about 18, about 19, or about 20.

Centrifugation is performed using any appropriate equipment and method. Centrifugation of cell culture or lysate for the purposes of separating a soluble fraction from an insoluble fraction is well-known in the art. For example, lysed cells are sometimes centrifuged at 20,800×g for 20 minutes (at 4° C.), and the supernatants removed using manual or automated liquid handling. The pellet (insoluble) fraction is resuspended in a buffered solution, e.g., phosphate buffered saline (PBS), pH 7.4. Resuspension is often carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures.

Fermentation Format

In one embodiment, fermentation is used in the methods of producing recombinant asparaginase. The expression system according to the present disclosure is cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media often contains mineral salts and a carbon source, but is often supplemented with, e.g., low levels of amino acids, vitamins, peptones, or other ingredients, though these are added at very minimal levels. Media is often prepared using the methods described in the art, e.g., in U.S. Pat. App. Pub. No. 2006/0040352, referenced and incorporated by reference above. Details of cultivation procedures and mineral salts media useful in the methods herein are described by Riesenberg, D et al., 1991, "High cell density cultivation of *Escherichia coli* at controlled specific growth rate," J. Biotechnol. 20 (1):17-27.

Fermentation may be performed at any scale. The expression systems according to the present disclosure are useful for recombinant protein expression at any scale. Thus, e.g., microliter-scale, milliliter scale, centiliter scale, and deciliter scale fermentation volumes may be used, and 1 Liter scale and larger fermentation volumes are often used.

In embodiments, the fermentation volume is at or above about 1 Liter. In embodiments, the fermentation volume is about 0.5 liters to about 100 liters. In embodiments, the fermentation volume is about 1 liter, about 2 liters, about 3 liters, about 4 liters, about 5 liters, about 6 liters, about 7 liters, about 8 liters, about 9 liters, or about 10 liters. In embodiments, the fermentation volume is about 0.5 liters to about 2 liters, about 0.5 liters to about 5 liters, about 0.5 liters to about 10 liters, about 0.5 liters to about 25 liters, about 0.5 liters to about 50 liters, about 0.5 liters to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

Protein Analysis

In embodiments, recombinant asparaginase protein produced by the methods of the provided herein is analyzed. Recombinant asparaginase is sometimes analyzed, for example, by biolayer interferometry, SDS-PAGE, Western blot, Far Western blot, ELISA, absorbance, or mass spectrometry (e.g., tandem mass spectrometry).

In some embodiments, the concentration and/or amounts of recombinant asparaginase protein generated are determined, for example, by Bradford assay, absorbance, Coomassie staining, mass spectrometry, etc.

Protein yield in the insoluble and soluble fractions as described herein are often determined by methods known to those of skill in the art, for example, by capillary gel electrophoresis (CGE), and Western blot analysis. Soluble fractions are often evaluated, for example, using biolayer interferometry.

The asparaginase monomer is capable of forming active tetramer, e.g., in cell lysate, cell sonicate, and upon further purification. Following expression of the recombinant asparaginase in a bacterial expression system, e.g., in a E. coli or Pseudomonas host strain, the recombinant protein can be purified using any suitable method known in the art, e.g., to remove host cell proteins. Purification methods can include, e.g., cation exchange chromatography, anion exchange chromatography, size exclusion chromatography, high performance liquid chromatography (HPLC), or a combination of these and/or other known methods. Asparaginase protein purification is described in the literature, e.g., in U.S. Pat. No. 5,310,670, "Method for the purification of Erwinia L-asparaginase," and U.S. Pat. No. 8,323,948, "Asparaginases and uses thereof," each incorporated by reference herein in its entirety. Based on our expression experiments, a type II asparaginase expressed in P. fluorescens is present as active, tetrameric asparaginase enzyme in sonicates.

In embodiments, a measurable characteristic (e.g., activity, size, length, or other characteristic indicative of active and/or intact protein) of an amount of an unpurified or purified asparaginase sample is compared with the same measurable characteristic of the same amount of an asparaginase standard sample (e.g., a commercially obtained asparaginase). It is understood that the amount of asparaginase protein in a sample can be determined by any suitable assay known in the art for protein measurement, and the activity by any suitable assay, e.g., as described herein.

Useful measures of protein yield include, e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of active protein (e.g., amount of active protein/amount protein used in the assay), percent or fraction of total cell protein (tcp), amount of protein/cell, and percent dry biomass.

In embodiments, the methods herein are used to obtain a yield of soluble recombinant asparaginase protein, e.g., a monomeric or tetrameric type II asparaginase, of about 20% to about 90% total cell protein. In certain embodiments, the yield of soluble recombinant asparaginase is about 20% total cell protein, about 25% total cell protein, about 30% total cell protein, about 31% total cell protein, about 32% total cell protein, about 33% total cell protein, about 34% total cell protein, about 35% total cell protein, about 36% total cell protein, about 37% total cell protein, about 38% total cell protein, about 39% total cell protein, about 40% total cell protein, about 41% total cell protein, about 42% total cell protein, about 43% total cell protein, about 44% total cell protein, about 45% total cell protein, about 46% total cell protein, about 47% total cell protein, about 48% total cell protein, about 49% total cell protein, about 50% total cell protein, about 51% total cell protein, about 52% total cell protein, about 53% total cell protein, about 54% total cell protein, about 55% total cell protein, about 56% total cell protein, about 57% total cell protein, about 58% total cell protein, about 59% total cell protein, about 60% total cell protein, about 65% total cell protein, about 70% total cell protein, about 75% total cell protein, about 80% total cell protein, about 85% total cell protein, or about 90% total cell protein. In some embodiments, the yield of soluble recombinant asparaginase is about 20% to about 25% total cell protein, about 20% to about 30% total cell protein, about 20% to about 35% total cell protein, about 20% to about 40% total cell protein, about 20% to about 45% total cell protein, about 20% to about 50% total cell protein, about 20% to about 55% total cell protein, about 20% to about 60% total cell protein, about 20% to about 65% total cell protein, about 20% to about 70% total cell protein, about 20% to about 75% total cell protein, about 20% to about 80% total cell protein, about 20% to about 85% total cell protein, about 20% to about 90% total cell protein, about 25% to about 90% total cell protein, about 30% to about 90% total cell protein, about 35% to about 90% total cell protein, about 40% to about 90% total cell protein, about 45% to about 90% total cell protein, about 50% to about 90% total cell protein, about 55% to about 90% total cell protein, about 60% to about 90% total cell protein, about 65% to about 90% total cell protein, about 70% to about 90% total cell protein, about 75% to about 90% total cell protein, about 80% to about 90% total cell protein, about 85% to about 90% total cell protein, about 31% to about 60% total cell protein, about 35% to about 60% total cell protein, about 40% to about 60% total cell protein, about 45% to about 60% total cell protein, about 50% to about 60% total cell protein, about 55% to about 60% total cell protein, about 31% to about 55% total cell protein, about 31% to about 50% total cell protein, about 31% to about 45% total cell protein, about 31% to about 40% total cell protein, about 31% to about 35% total cell protein, about 35% to about 55% total cell protein, or about 40% to about 50% total cell protein.

In embodiments, the methods herein are used to obtain a yield of soluble recombinant asparaginase protein, e.g., a monomeric or tetrameric type II asparaginase, of about 1 gram per liter to about 50 grams per liter. In certain embodiments, the yield of soluble recombinant asparaginase is about 1 grams per liter, about 2 grams per liter, about 3 grams per liter, about 4 grams per liter, about 5 grams per liter, about 6 grams per liter, about 7 grams per liter, about 8 grams per liter, about 9 grams per liter, about 10 gram per liter, about 11 grams per liter, about 12 grams per liter, about 13 grams per liter, about 14 grams per liter, about 15 grams per liter, about 16 grams per liter, about 17 grams per liter, about 18 grams per liter, about 19 grams per liter, about 20 grams per liter, about 21 grams per liter, about 22 grams per liter, about 23 grams per liter about 24 grams per liter, about 25 grams per liter, about 26 grams per liter, about 27 grams per liter, about 28 grams per liter, about 30 grams per liter, about 35 grams per liter, about 40 grams per liter, about 45 grams per liter, about 50 grams per liter, about 1 grams per liter to about 5 grams per liter, about 1 grams to about 10 grams per liter, about 10 gram per liter to about 12 grams per liter, about 10 grams per liter to about 13 grams per liter, about 10 grams per liter to about 14 grams per liter, about 10 grams per liter to about 15 grams per liter, about 10 grams per liter to about 16 grams per liter, about 10 grams per liter to about 17 grams per liter, about 10 grams per liter to about 18 grams per liter, about 10 grams per liter to about 19 grams per liter, about 10 grams per liter to about 20 grams per liter, about 10 grams per liter to about 21 grams per liter, about 10 grams per liter to about 22 grams per liter, about 10 grams per liter to about 23 grams per liter, about 10 grams per liter to about 24 grams per liter, about 10 grams per liter to about 25 grams per liter, about 10 grams per liter to about 30 grams per liter, about 10 grams per liter to about 40 grams per liter, about 10 grams per liter to about 50 grams per liter, about 10 gram per liter to about 12 grams per liter, about 12 grams per liter to about 14 grams per liter, about 14 grams per liter to about 16 grams per liter, about 16 grams per liter to about 18 grams per liter, about 18 grams per liter to about 20 grams per liter, about 20 grams per liter to about 22 grams per liter, about 22 grams per liter to about 24 grams per liter, about 23 grams per liter to about 25 grams per liter, about 10 grams per liter to about 25 grams per liter, about 11 grams per liter to about 25 grams per liter, about 12 grams per liter to about 25 grams per liter, about 13 grams per liter to about 25 grams per liter, about 14 grams per liter to about 25 grams per liter, about 15 grams per liter to about 25 grams per liter, about 16 grams per liter to about 25 grams per liter, about 17 grams per liter to about 25 grams per liter, about 18 grams per liter to about 25 grams per liter, about 19 grams per liter to about 25 grams per liter, about 20 grams per liter to about 25 grams per liter, about 21 grams per liter to about 25 grams per liter, about 22 grams per liter to about 25 grams per liter, about 23 grams per liter to about 25 grams per liter, or about 24 grams per liter to about 25 grams per liter. In embodiments, the soluble recombinant protein yield is about 10 gram per liter to about 13 grams per liter, about 12 grams per liter to about 14 grams per liter, about 13 grams per liter to about 15 grams per liter, about 14 grams per liter to about 16 grams per liter, about 15 grams per liter to about 17 grams per liter, about 16 grams per liter to about 18 grams per liter, about 17 grams per liter to about 19 grams per liter, about 18 grams per liter to about 20 grams per liter, about 20 grams per liter to about 22 grams per liter, about 22 grams per liter to about 24 grams per liter, or about 23 grams per liter to about 25 grams per liter. In embodiments, the soluble recombinant protein yield is about 10 grams per liter to about 25 grams per liter, about 12 gram per liter to about 24 grams per liter, about 14 grams per liter to about 22 grams per liter, about 16 grams per liter to about 20 grams per liter, or about 18 grams per liter to about 20 grams per liter. In embodiments, the extracted protein yield is about 5 grams per liter to about 15 grams per liter, about 5 gram per liter to about 25 grams per liter, about 10 grams per liter to about 15 grams per liter, about 10 grams per liter to about 25 grams per liter, about 15 grams per liter to about 20 grams per liter, about 15 grams per liter to about 25 grams per liter, or about 18 grams per liter to about 25 grams per liter.

In embodiments, the amount of recombinant asparaginase, e.g., a monomeric or tetrameric type II asparaginase, detected in the soluble fraction is about 10% to about 100% of the amount of the total recombinant asparaginase produced. In embodiments, this amount is about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%, or about 100% of the amount of the total recombinant asparaginase produced. In embodiments, this amount is about 10% to about 20%, 20% to about 50%, about 25% to about 50%, about 25% to about 50%, about 25% to about 95%, about 30% to about 50%, about 30% to about 40%, about 30% to about 60%, about 30% to about 70%, about 35% to about 50%, about 35% to about 70%, about 35% to about 75%, about 35% to about 95%, about 40% to about 50%, about 40% to about 95%, about 50% to about 75%, about 50% to about 95%, about 70% to about 95%, or about 80 to about 100% of the amount of the total recombinant asparaginase produced.

In some embodiments, the amount of soluble recombinant asparaginase, e.g., a monomeric or tetrameric type II asparaginase, is expressed as a percentage of the total soluble protein produced in a culture. Data expressed in terms of recombinant asparaginase protein weight/volume of cell culture at a given cell density can be converted to data expressed as percent recombinant protein of total cell protein. It is within the capabilities of a skilled artisan to convert volumetric protein yield to % total cell protein, for example, knowing the amount of total cell protein per volume of cell culture at the given cell density. This number can be determined if one knows 1) the cell weight/volume of culture at the given cell density, and 2) the percent of cell weight comprised by total protein. For example, at an OD550 of 1.0, the dry cell weight of *E. coli* is reported to be 0.5 grams/liter ("Production of Heterologous Proteins from Recombinant DNA *Escherichia coli* in Bench Fermentors," Lin, N. S., and Swartz, J. R., 1992, METHODS: A Companion to Methods in Enzymology 4: 159-168). A bacterial cell is comprised of polysaccharides, lipids, and nucleic acids, as well as proteins. An *E. coli* cell is reported to be about 52.4 to 55% protein by references including, but not limited to, Da Silva, N. A., et al., 1986, "Theoretical Growth Yield Estimates for Recombinant Cells," Biotechnology and Bioengineering, Vol. XXVIII: 741-746, estimating protein to make up 52.4% by weight of *E. coli* cells, and "*Escherichia coli* and *Salmonella typhimurium* Cellular and Molecular Biology," 1987, Ed. in Chief Frederick C. Neidhardt, Vol. 1, pp. 3-6, reporting protein content in *E. coli* as 55% dry cell weight. Using the measurements above (i.e., a dry cell weight of 0.5 grams/liter, and protein as 55% cell weight), the amount of total cell protein per volume of cell culture at an A550 of 1.0 for *E. coli* is calculated as 275 µg total cell protein/ml/A550. A calculation of total cell protein per volume of cell culture based on wet cell weight can use, e.g., the determination by Glazyrina, et al. (Microbial Cell Factories 2010, 9:42, incorporated herein by reference) that an A600 of 1.0 for *E. coli* resulted in a wet cell weight of 1.7 grams/liter and a dry cell weight of 0.39 grams/liter. For example, using this wet cell weight to dry cell weight comparison, and protein as 55% dry cell weight as described above, the amount of total cell protein per volume of cell culture at an A600 of 1.0 for *E. coli* can be calculated as 215 µg total cell protein/ml/A600. For *Pseudomonas fluorescens*, the amount of total cell protein per volume of cell culture at a given cell density is similar to that found for *E. coli*. *P. fluorescens*, like *E. coli*, is a gram-negative, rod-shaped bacterium. The dry cell weight of *P. fluorescens* ATCC 11150 as reported by Edwards, et al., 1972, "Continuous Culture of *Pseudomonas fluorescens* with Sodium Maleate as a Carbon Source," Biotechnology and Bioengineering, Vol. XIV, pages 123-147, is 0.5 grams/liter/A500. This is the same weight reported by Lin, et al., for *E. coli* at an A550 of 1.0. Light scattering measurements made at 500 nm and at 550 nm are expected to be very similar. The percent of cell weight comprised by total cell protein for *P. fluorescens* HK44 is described as 55% by, e.g., Yarwood, et al., July 2002, "Noninvasive Quantitative Measurement of Bacterial Growth in Porous Media under Unsaturated-Flow Conditions," Applied and Environmental Microbiology 68(7): 3597-3605. This percentage is similar to or the same as those given for *E. coli* by the references described above.

In embodiments, the amount of soluble recombinant asparaginase, e.g., a monomeric or tetrameric type II asparaginase, produced is about 0.1% to about 95% of the total soluble protein produced in a culture. In embodiments, this amount is more than about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total soluble protein produced in a culture. In embodiments, this amount is about 0.1%, 0.5%, 1%, 5%, 10%, 15%, 20%, 25%, 30%, 40%, 45%, 50%, 55%, 60%, 65%, 70%, 75%, 80%, 85%, 90%, or 95% of the total soluble protein produced in a culture. In embodiments, this amount is about 5% to about 95%, about 10% to about 85%, about 20% to about 75%, about 30% to about 65%, about 40% to about 55%, about 1% to about 95%, about 5% to about 30%, about 1% to about 10%, about 10% to about 20%, about 20% to about 30%, about 30% to about 40%, about 40% to about 50%, about 50 to about 60%, about 60% to about 70%, or about 80% to about 90% of the total soluble protein produced in a culture.

In embodiments, the amount of soluble recombinant asparaginase, e.g., a monomeric or tetrameric type II asparaginase, produced is about 0.1% to about 50% of the dry cell weight (DCW). In embodiments, this amount is more than about 0.1%, 0.5%, 1%, 5%, 10%, 15%, 20%, 25%, 30%, 40%, 45%, or 50% of DCW. In embodiments, this amount is about 0.1%, 0.5%, 1%, 5%, 10%, 15%, 20%, 25%, 30%, 40%, 45%, or 50% of DCW. In embodiments, this amount is about 5% to about 50%, about 10% to about 40%, about 20% to about 30%, about 1% to about 20%, about 5% to about 25%, about 1% to about 10%, about 10% to about 20%, about 20% to about 30%, about 30% to about 40%, or about 40% to about 50% of the total soluble protein produced in a culture.

Solubility and Activity

The "solubility" and "activity" of a protein, though related qualities, are generally determined by different means. Solubility of a protein, particularly a hydrophobic protein, indicates that hydrophobic amino acid residues are improperly located on the outside of the folded protein. Protein activity, which is often evaluated using different methods, e.g., as described below, is another indicator of proper protein conformation. "Soluble, active, or both" as used herein, refers to protein that is determined to be soluble, active, or both soluble and active, by methods known to those of skill in the art.

Activity Assay

Assays for evaluating asparaginase activity are known in the art and include but are not limited to fluorometric, colorometric, chemiluminescent, spectrophotometric, and other enzyme assays available to one of skill in the art. These assays can be used to compare activity or potency of an asparaginase preparation to a commercial or other asparaginase preparation.

In embodiments, activity or potency is represented by the percent active protein in the extract supernatant as compared with the total amount assayed. This is based on the amount of protein determined to be active by the assay relative to the total amount of protein used in assay. In other embodiments, activity or potency is represented by the % activity or potency level of the protein compared to a standard or control protein. This is based on the amount of active protein in supernatant extract sample relative to the amount of active protein in a standard sample (where the same amount of protein from each sample is used in assay).

In embodiments, the standard or control protein used in the activity or potency assay for comparison to a produced recombinant type II asparaginase is the active ingredient in Elspar®, or the active ingredient in any recombinant type II asparaginase product approved for clinical use and known in the art. In embodiments, the measured activity or potency of the recombinant type II asparaginase produced is compared with an activity or potency measured in the same amount of the standard or control type II asparaginase using the same method for measuring type II asparaginase activity. In embodiments, the measured activity or potency of the recombinant type II asparaginse produced is compared with an activity or potency measured in the same amount of a control type II asparaginase that has been commercially approved for use in patients.

In embodiments, about 40% to about 100% of the recombinant asparaginase protein, is determined to be active, soluble, or both. In embodiments, about 40%, about 50%, about 60%, about 70%, about 80%, about 90%, or about 100% of the recombinant asparaginase protein is determined to be active. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the recombinant asparaginase protein is determined to be active, soluble, or both.

In other embodiments, about 75% to about 100% of the recombinant asparaginase is determined to be active, soluble, or both. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the recombinant asparaginase is determined to be active, soluble, or both.

In embodiments, a method of producing or expressing a recombinant type II asparaginase as described herein further comprises measuring the activity or potency of the recombinant type II asparaginase produced and comparing the measured activity or potency of the recombinant type II asparaginase produced with an activity or potency measured in the same amount of a control type II asparaginase using the same assay, wherein the measured activity or potency of the recombinant type II asparaginase produced is comparable to the activity or potency of the control type II asparaginase. In embodiments, comparable activity or potency is defined as 100% (which also can be expressed as 1.0), that is, when the activity or potency of the recombinant type II asparaginase produced and the control type II asparaginase are equal. In embodiments, the activity or potency of the recombinant type II asparaginase produced compared to the control type II asparaginase is about 80% to about 120%. In embodiments, the activity or potency is about 85% to about 115%. In embodiments, the activity or potency is about 90% to about 110%. In embodiments, the activity or potency is about 70% to about 130%. In embodiments, the activity or potency is about 65% to about 135%. In embodiments, the activity or potency of the recombinant type II asparaginase produced compared to the control type II asparaginase is about or at least about 65%, about or at least about 66%, about or at least about 67%, about or at least about 68%, about or at least about 69%, about or at least about 70%, about or at least about 71%, about or at least about 72%, about or at least about 73%, about or at least about 74%, about or at least about 75%, about or at least about 75%, about or at least about 76%, about or at least about 77%, about or at least about 78%, about or at least about 79%, about or at least about 80%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98%, about or at least about 99%, about or at least about 100%, about or at least about 101%, about or at least about 102%, about or at least about 103%, about or at least about 104%, about or at least about 105%, about or at least about 106%, about or at least about 107%, about or at least about 108%, about or at least about 109%, about or at least about 110%, about or at least about 111%, about or at least about 112%, about or at least about 113%, about or at least about 114%, about or at least about 115%, about or at least about 116%, about or at least about 117%, about or at least about 118%, about or at least about 119%, about or at least about 120%, about or at least about 121%, about or at least about 122%, about or at least about 123%, about or at least about 124%, about or at least about 125%, about or at least about 126%, about or at least about 127%, about or at least about 128%, about or at least about 129%, about or at least about 130%, about or at least about 131%, about or at least about 132%, about or at least about 133%, about or at least about 134%, or about or at least about 135%. In embodiments, the activity or potency of the recombinant type II asparaginase produced compared to the control type II asparaginase is about 68% to about 132%, about 70% to about 130%, about 72% to about 128%, about 75% to about 125%, about 80% to about 120%, about 85% to about 115%, about 65% to about 110%, about 68% to about 110%, about 70% to about 110%, about 72% to about 110%, about 78% to about 110%, about 80% to about 110%, about 90% to about 110%, about 95% to about 105%, about 85% to about 110%, about 90% to about 110%, about 95% to about 110%, about 96% to about 110%, about 97% to about 110%, about 98% to about 110%, about 99% to about 110%, about 100% to about 110%, about 65% to about 105%, about 68% to about 105%, about 70% to about 105%, about 72% to about 105%, about 80% to about 105%, about 85% to about 105%, about 90% to about 105%, about 95% to about 105%, about 96% to about 105%, about 97% to about 105%, about 98% to about 105%, about 99% to about 105%, about 100% to about 105%, about 65% to about 100%, about 68% to about 100%, about 70% to about 100%, about 72% to about 100%, about 75% to about 100%, about 78% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, about 95% to about 99%, about 96% to about 99%, about 97% to about 99%, about 70% to about 135%, about 75% to about 135%, about 80% to about 135%, about 85% to about 135%, about 90% to about 135%, about 75% to about 130%, about 80% to about 130%, about 85% to about 130%, about 90% to about 130%, about 80% to about 125%, about 85% to about 125%, about 90% to about 125%, about 85% to about 120%, about 90% to about 120%, or about 95% to about 120%.

EXAMPLES

The following examples are given for the purpose of illustrating various embodiments of the disclosure and are not meant to limit the present disclosure in any fashion. The present examples, along with the methods described herein are presently representative embodiments, are exemplary, and are not intended as limitations on the scope. Changes therein and other uses which are encompassed within the spirit of the disclosure as defined by the scope of the claims will occur to those skilled in the art.

Example 1: Preparation of Asparaginase Expression Constructs

The *E. coli* A-1-3 L-asparaginase II gene was optimized for expression in *P. fluorescens* and cloned into a set of expression vectors for cytoplasmic and periplasmic expression. The amino acid sequence used is disclosed herein as SEQ ID NO: 1. The nucleic acid sequence used is disclosed herein as SEQ ID NO: 2.

Expression was evaluated using a series of the secretion leader sequences, some with a high RBS sequence and some with a medium RBS sequence. In addition, cytoplasmic expression was evaluated, using no leader.

Each construct was transformed into *P. fluorescens* host strains DC454 (pyrF deficient, no PD or FMO) and DC441 (pyrF, Lon, and HslUV deficient), and the resulting expression strains were evaluated for *E. coli* A-1-3 L-asparaginase II production in 0.5 mL cultures. The whole broth was sonicated, centrifuged, and the soluble fractions analyzed by CGE.

Growth and Expression in 96 Well Format

For the expression plasmid screening, ligation mixtures for each of the *E. coli* A-1-3 L-asparaginase II expression plasmids were transformed into *P. fluorescens* host strains DC454 and DC441 cells as follows. Twenty-five microliters of competent cells were thawed and transferred into a 96-multiwell Nucleovette® plate (Lonza VHNP-1001), and ligation mixture was added to each well. Cells were electroporated using the Nucleofector™ 96-well Shuttle™ system (Lonza AG). Cells were then transferred to 96-well deep well plates with 400 µl M9 salts 1% glucose medium and trace elements. The 96-well plates (seed plates) were incubated at 30° C. with shaking for 48 hours. Ten microliters of seed culture were transferred in duplicate into 96-well deep well plates, each well containing 500 µl of HTP medium, supplemented with trace elements and 5% glycerol, and incubated as before, for 24 hours. Isopropyl-β-D-1-thiogalactopyranoside (IPTG) was added at the 24-hour time point to each well for a final concentration of 0.3 mM, to induce the expression of target proteins Mannitol (Sigma, M1902) was added to each well for a final concentration of 1% to induce the expression of folding modulators in folding modulator overexpressing strains. Cell density was measured by optical density at 600 nm (OD600) at 24 hours after induction to monitor growth. Twenty-four hours after induction, cells were harvested, diluted 1:3 in 1×PBS for a final volume of 400 µl, then frozen. Samples were prepared and analyzed as described below.

The expression results for the top expression plasmids are shown in Tables 5 and 6.

TABLE 5

Expression Plasmid Screening in DC454

| Sample_Name | Leader | Result (mg/L) |
|---|---|---|
| STR55304-2 | Lao | 2052 |
| STR55312-2 | Pbp | 2016 |
| STR55305-2 | Ibp-S31A | 1413 |
| STR55334-2 | 8484 | 1322 |
| STR55333-2 | Leader R | 1073 |
| STR55313-2 | PbpA20V | 1068 |
| STR55302-2 | Azu | 884 |

TABLE 5-continued

Expression Plasmid Screening in DC454

| Sample_Name | Leader | Result (mg/L) |
|---|---|---|
| STR55317-2 | Leader D | 819 |
| STR55315-2 | Leader B | 764 |
| STR55310-2 | CupC2 | 751 |

TABLE 6

Expression Plasmid Screening in DC441 Host

| Sample_Name | Leader | Result-Bkg (I0) ug/mL |
|---|---|---|
| STR55382-2 | Azu | 993 |
| STR55384-2 | Lao | 1422 |
| STR55385-2 | Ibp-S31A | 1048 |
| STR55392-2 | Pbp | 1305 |
| STR55393-2 | PbpA20V | 997 |
| STR55397-2 | Leader D | 698 |
| STR55413-2 | Leader R | 1005 |
| STR55414-2 | 8484 | 1199 |

For the host strain screening, expression plasmids selected based on the expression plasmid screening results each were transformed into each of 24 P. fluorescens host strains in an array, including the wild-type (WT) or parent DC454 strain, protease deletion (PD) strains, folding modulator overexpressing (FMO) strains and protease deletion plus folding modulator overexpressor (PD/FMO) strains. E. coli asparaginase fused to the P. fluorescens aparaginase secretion leader (AnsB) was included in the array (amino acid sequence set forth as SEQ ID NO: 14; coding sequence set forth as SEQ ID NO: 15). Folding modulators, when present, were encoded on a second plasmid and expression was driven by a P. fluorescens-native mannitol inducible promoter. The host strain screen transformations were performed as follows: twenty-five microliters of P. fluorescens host strain competent cells were thawed and transferred into a 96-multi-well Nucleovette® plate, and 10 µl plasmid DNA (10 ng) was added to each well. The cells were electroporated, cultured, induced in HTP format and harvested as described for the plasmid expression screening above. Samples were prepared and analyzed as described below.

Preparation of Samples for Analysis

Soluble fractions were prepared by sonication followed by centrifugation. Culture broth samples (400 µL) were sonicated with the Cell Lysis Automated Sonication System (CLASS, Scinomix) with a 24 probe tip horn under the following settings: 20 pulses per well at 10 seconds per pulse, and 60% power with 10 seconds between each pulse (Sonics Ultra-Cell). The lysates were centrifuged at 5,500×g for 15 minutes (4° C.) and the supernatants collected (soluble fraction).

SDS-CGE Analysis

Protein samples were analyzed by microchip SDS capillary gel electrophoresis using a LabChip GXII instrument (PerkinElmer) with a HT Protein Express chip and corresponding reagents (part numbers 760528 and CLS760675, respectively, PerkinElmer). Samples were prepared following the manufacturer's protocol (Protein User Guide Document No. 450589, Rev. 3). Briefly, in a 96-well polypropylene conical well PCR plate, 4 µL of sample were mixed with 14 µL of sample buffer, with 70 mM DTT reducing agent, heated at Whole broth sampled 24 hours post induction was processed as described above and soluble fractions were analyzed by SDS-CGE.

A commercially available L-asparaginase activity assay kit (Sigma) detected significant L-asparaginase activity in HTP culture lysate samples from top yielding strain STR55382 (Lao leader) when compared to a Null sample.

The plasmids and corresponding secretion leaders screened in the array included:
p742-006 (Azu)
p742-008 (LAO)
p742-009 (Ibp-S31A)
p742-016 (Pbp)
p742-017 (PbpA20V)
p742-021 (Leader D)
p742-037 (Leader R)
p742-038 (8484)
p742-041 (P. fluorescens AnsB).

The expression strains were cultured and induced as described above. The SDS-CGE analysis of the soluble and insoluble fractions showed high level expression of asparaginase (FIG. 1). High titers were observed in the expression strains including those set forth in Table 7.

TABLE 7

Host Strain Screening

| Expression Strain ID | Plasmid (Leader) | Host Strain | Soluble I24 (ug/ml) | Insoluble I24 (ug/ml) | Whole Cell I24 (ug/ml) |
|---|---|---|---|---|---|
| STR55467 | p742-041 (AnsB) | DC454 (pyrF, no PD, no FMO) | 3603 | 268 | 3871 |
| STR55689 | p742-009 (Ibp-S31A) | DC542 (pyrF proC, FMO lepB (RXF01181.1) | 2503 | 152 | 2655 |
| STR55559 | p742-009 (Ibp-S31A) | PF1201 (pyrF proC, deficient in proteases Lon (RXF04653.1), DegP1(RXF01250.2) DegP2 S219A (RXF07210.1 with S219A substitution), Prc1(RXF06586.1), and AprA (RXF04304.1)) | 2491 | 174 | 2665 |
| STR55561 | p742-016 (Pbp) | PF1201 | 2070 | 484 | 2554 |
| STR55555 | p742-038 (8484) | DC549 (pyrF proC, FMO tig-RXF04655) | 1772 | 94 | 1865 |

Figure 2:
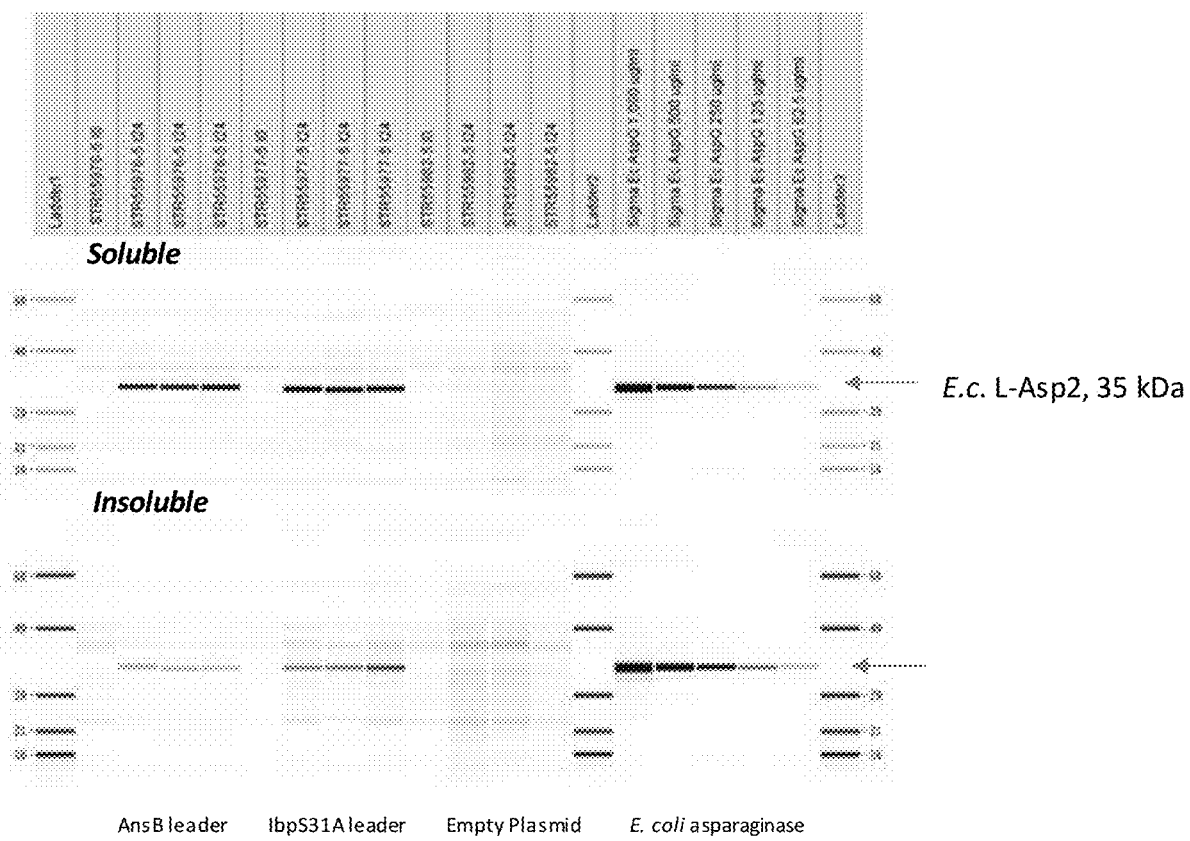
FIG. 2. SDS-CGE Gel-like Images Shake Flask Expression Analysis. Asparaginase shake flask expression sonicate soluble (upper panel) and insoluble (lower panel) were analyzed by reduced SDS-CGE. The late at the far left shows molecular weight marker ladder (upper panel MW ladder 68 kDa, 48 kDa, 29 kDa, 21 kDa, 16 kDa; lower panel MW ladder 68 kDa, 58 kDa, 29 kDa, 21 kKa, 16 kDa), the 14$^{th}$ lane and the far right lane show the same ladders. From left to right beginning immediately to the right of ladder 1 are lanes showing expression patterns observed in the soluble fractions of strain STR55976 at I0, STR55976 at 124, STR55976 at 124, STR55976 at 124, STR55977 at I0, STR55977 at 124, STR55977 at 124, STR55977 at 124, STR55982 at I0, STR55982 at 124, STR55982 at 124, STR55982 at 124 where J0 samples are taken at the time of induction and 124 samples are taken 24 hours post induction. From left to right beginning immediately to the right of ladder 2 are Sigma *E. coli* L-Asparaginase 1000 µg/ml, Sigma *E. coli* L-Asparaginase 500 µg/ml, Sigma *E. coli* L-Asparaginase 250 µg/ml, Sigma *E. coli* L-Asparaginase 125 µg/ml, and Sigma *E. coli* L-Asparaginase 62.5 µg/ml. Arrows to the right of the gel images indicate migration of the asparaginase target protein (35 kDa). Sigma *E. coli* asparaginase was run as a control standard curve.

Example 2: Shake Flask Expression Analysis of L-Asp1 and L-Asp2 Deficient Host Strains A *P. fluorescens* host strain deficient in L-Asp1 and L-Asp 2, PF1433, was generated based on wild-type host strain DC454. Expression analysis of the *E. coli* A-1-3 asparaginase type II in 200 mL shake flask cultures was carried out (Table 8). The values shown are an average obtained from 10 different sonicate soluble fraction repetitions. SDS-CGE quantification was done using Sigma *E. coli* L-Asp2 standard curve. Production of greater than 1 g/L soluble monomer was observed. An exemplary SDS-CGE image of 5× diluted samples is provided in FIG. 2.

The last row of Table 8 shows the expression results for a strain expressing the native *P. fluorescens* AnsB, with the *P. fluorescens* AnsB secretion leader, assayed in the same experiment. The *P. fluorescens* leader-*E. coli* asparaginase construct expressed substantially more protein than did the construct comprising the *P. fluorescens* leader-*P. fluorescens* asparaginase.

TABLE 8

Shake Flask Expression Analysis of L-Asp1 and L-Asp2 Deficient Host Strains

| Expression Strain ID | Plasmid (Leader) | Host Strain | Avg Sol Reduced (µg/ml) | % CV | Avg Insol Reduced (µg/ml) | % CV |
|---|---|---|---|---|---|---|
| STR55976 (*E. coli* A-1-3 asparaginase type II) | p742-041 (AnsB) | PF1433 (PyrF, AspG1, AspG2 deficient) | 1011 | 5 | 129 | 41 |
| STR55977 (*E. coli* A-1-3 asparaginase type II) | p742-009 (Ibp-S31A) | PF1433 | 1514 | 9 | 253 | 56 |
| STR55981 (*P. fluorescens* AnsB) | p744-001 (AnsB) | PF1433 | 677 | 12 | 200 | 49 |

Activity analysis of shake flask expression was also determined (Table 9). Soluble sonicate samples generated from each of the shake flask expression strains were analyzed for asparaginase activity using a commercial kit purchased from Sigma (Asparaginase Activity Assay Kit) according to the manufacturer's instructions. This kit measures activity using a coupled enzyme reaction which produces a colorimetric end product proportional to the aspartate generated. *E. coli* asparaginase type II from Sigma (A3809) was spiked into STR55982 null lysate as a positive control (last row). Activity was calculated from two assay replicates of a single soluble sonicate sample. No activity was detected in either null sonicate at 1:25,000 dilution of the lysate. 742 (*E. coli*) and Sigma L-Asp (*E. coli*) standard spike-in lysates at 1:25,000 dilution showed comparable activity.

TABLE 9

Shake Flask Expression Activity Analysis

| Sample Description | Sample ID | Soluble Sonicate Titer (SDS-CGE reduced µg/ml) | Sample Dilution Factor | Δ A570 (TF-T0) 20 min | Aspartate Generated (nmol) |
|---|---|---|---|---|---|
| AnsB leader | STR55976-5 | 202 | 25,000 | 0.03 | 0.36 |
| Ibp-S31A leader | STR55977-5 | 303 | 25,000 | 0.04 | 0.74 |
| AspG– null | STR55982-5 | 0 | 25,000 | 0.00 | 0.00 |
| AspG+ null | DC432-657 | 0 | 25,000 | 0.00 | 0.00 |
| Null spike to 250 µg/ml | AspG2 Sigma | 250 | 25,000 | 0.03 | 0.03 |

Figure 3:
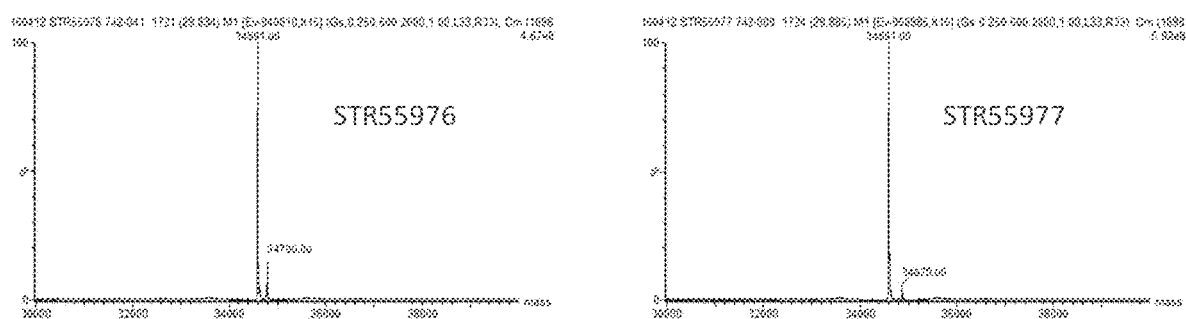
FIG. 3. Mass Spectrometry Data-Shake Flask Expression Analysis. The left panel shows LC-MS data for STR55976, and the right panel shows data for STR55977.

LC-MS analysis of shake flask expression also was performed (Table 10). Intact mass was observed as expected for 742 proteins examined. Exemplary mass spectrometry data is provided in FIG. 3. No significant difference between predicted and observed molecular weights was detected.

TABLE 10

Shake Flask Expression LC-MS Analysis

| Sample ID | Theor. MW (Da) -signal | Observed MW (Da) | Observed Theor. MW (Da) |
|---|---|---|---|
| STR55976 742-041 | 34591.96 | 34591 | −0.96 |
| STR55977 742-009 | | 34591 | −0.96 |
| 742 Sigma AspG2 | 34591.96 | 34591 | −0.96 |

The identified tetrameric (active) protein form present was further evaluated by size exclusion chromatography. Soluble sonicated samples were desalted by ion exchange spin column prior to analysis. Size exclusion chromatography showed a peak correlating to the expected MW of tetramer observed in soluble sonicates, consistent with an E. coli L-Asp2 standard (Sigma).

Example 3: Construction of P. fluorescens Asparaginase Deficient Host Strains

Construction of P. fluorescens Asparaginase Gene Knock-Out Plasmids

A BLAST search of the P. fluorescens MB214 genome sequence using the asparaginase protein amino acid sequence as input resulted in output of two protein encoding genes (pegs) showing significant alignment: peg. 3886 (L-asparaginase EC 3.5.1.1 type II, SEQ ID NO: 54) and peg. 5048 (L-asparaginase EC 3.5.1.1, SEQ ID NO: 55). A cloned deletion construct for each native L-asparaginase gene was initiated by synthesizing DNA sequence fragments that contain a fusion of upstream and downstream flanking regions for each gene leaving only the start and stop codons of the gene targeted for deletion. These fragments were subsequently blunt-end ligated into the SrfI site of vector pDOW1261-24 to produce deletion plasmids pFNX3970 and pFNX3969, respectively.

The ligation reaction was subsequently transformed into E. coli DH5alpha cells (Thermo Scientific) to isolate colonies and purify successfully cloned deletion plasmid DNA.

Construction of Native L-Asparaginase-Deficient Host Strains

Chromosomal deletion of each gene was performed sequentially in the selected host strains using the following method: the deletion plasmid was electroporated into a P. fluorescens host strain which contains a chromosomal deletion in the pyrF gene involved in uracil (pyrimidine) biosynthesis. The deletion plasmid contains the PyrF coding sequence but is unable to replicate in P. fluorescens cells. The electroporated cells were plated onto M9 salts agar plates supplemented with 1% glucose and 250 ug/mL proline (if the host strain is a proline auxotroph). The resulting clones are able to synthesize uracil due to an integration event that recombines the entire deletion plasmid into the chromosome at one of the two homologous regions within the genome. To select for cells that have carried out a second homologous recombination between the integrated plasmid and the chromosome and thereby leave a deletion, plasmid integrant strains were grown to stationary phase in 3 mL LB medium supplemented with 250 ug/mL uracil and 250 ug/mL proline (if the host strain is a proline auxotroph). Cells were then plated on to LB uracil (250 ug/mL) plus 250 ug/mL proline (if the host strain is a proline auxotroph) agar plates that also contained 500 ug/mL 5-fluoroorotic acid (5-FOA) (Zymo Research). Cells that lose the integrated plasmid by recombination also lose the pyrF gene and are therefore expected to be resistant to 5-FOA, which would otherwise be converted into a toxic compound preventing cell growth. Single colonies exhibiting good growth in the presence of 5-FOA (500 ug/mL) were then picked and grown in 3 mL liquid M9 minimal medium containing 1% glucose supplemented with 250 µg/mL uracil and 250 µg/mL proline (if the host strain is a proline auxotroph) to generate culture for storage as glycerol stocks and as template for diagnostic PCR and sequencing reactions.

Confirmation of the Chromosomal Deletion of Native L-Asparaginase Genes

Diagnostic PCR reactions were used to screen for the desired native L-asparaginase gene chromosomal deletion utilizing primers annealing to chromosomal regions outside the synthesized gene deletion sequence cloned into the knock-out plasmid. DNA sequencing of the PCR product generated was used to determine that the desired native L-asparaginase gene deletion had occurred as expected without undesired mutations or DNA rearrangements.

The following P. fluorescens asparaginase KO host strains were generated.

PF1433 (PyrF, AspG1, and AspG2 deficient), was constructed by sequential deletion of the aspG2 and aspG1 genes in the host strain DC454 (PyrF deficient).

PF1434 (PyrF, ProC, AspG1, and AspG2 deficient), was constructed by sequential deletion of the aspG1 and aspG2 genes in the host strain DC455 (pyrF proC). Strain DC455 is the parent strain of both DC542 and DC549.

PF1442 (PyrF, ProC, AspG1, AspG2, Lon, DegP1, DegP2 S219A, Prc1, and AprA deficient), was constructed by sequential deletion of aspG2 and aspG1 in the host strain PF1201 (PyrF, ProC, proteases Lon, DegP1, DegP2 S219A, Prc1, and AprA deficient).

PF1443 (PyrF, ProC, AspG1, and AspG2 deficient; FMO LepB in pDOW3700), was constructed by transformation of the lepB encoding FMO plasmid pDOW3700 into PF1434.

PF1444 (PyrF, ProC, AspG1, and AspG2 deficient; FMO Tig in pDOW3707), was constructed by transformation of the Tig encoding FMO plasmid pDOW3703 into PF1434.

PF1445 (PyrF, ProC, AspG1, AspG2, Lon, DegP1, DegP2, S219A, Prc1, and AprA deficient; FMO DsbAC-Skp in pFNX4142), was constructed by the transformation of PF1442 with the DsbAC-Skp encoding plasmid pFNX4142.

Strains used are described in Table 11.

TABLE 11

Host Backgrounds of Asparaginase Deficient Expression Strains

| Expression Strain ID | Host Strain | Expression Plasmid | Background Phenotype* | Secretion Leader |
|---|---|---|---|---|
| STR57867 | PF1433 | p742-041 | Wild-type | AnsB |
| STR57864 | PF1445 | p742-009 | PD/FMO | Ibp-S31A |
| STR57865 | PF1445 | p742-016 | PD/FMO | Pbp |
| STR57866 | PF1445 | p742-041 | PD/FMO | AnsB |
| STR57860 | PF1443 | p742-041 | FMO | AnsB |
| STR57861 | PF1444 | p742-041 | FMO | AnsB |
| STR57862 | PF1443 | p742-009 | FMO | Ibp-S31A |
| STR57863 | PF1444 | p742-038 | FMO | 8484 |

* with regard to protease deficiency/deletion and folding modulator overexpression.

Example 4: 2 L Fermentation and Calculation of Soluble % TCP of Selected Expression Strains Strains STR57863 and STR57860 described in Example 3 were scaled to 2 L fermentation and each screened under up to eight different fermentation conditions. The 2 L scale fermentations (approximately 1 L final fermentation volume) were generated by inoculating a shake flask containing 600 mL of a chemically defined medium supplemented with yeast extract and glycerol with a frozen culture stock of the selected strain. After 16 to 24 h incubation with shaking at 30° C., equal portions of each shake flask culture were then aseptically transferred to each of the 8-unit multiplex fermentation system containing a chemically defined medium designed to support a high biomass. In the 2 L fermentors, cultures were operated under controlled conditions for pH, temperature, and dissolved oxygen in a glycerol fed-batch mode. The fed-batch high cell density fermentation process consisted of a growth phase followed by an induction phase, initiated by the addition of IPTG and 5 g/L mannitol once the culture reached the target biomass (wet cell weight). The conditions during the induction phase were varied according to the experimental design. The induction phase of the fermentation was allowed to proceed for approximately 24 hours. Analytical samples were withdrawn from the fermentor to determine cell density (optical density at 575 nm) and were then frozen for subsequent analyses to determine the level of target gene expression. At the final time point of 24 hours post-induction, the whole fermentation broth of each vessel was harvested by centrifugation at 15,900×g for 60 to 90 minutes. The cell paste and supernatant were separated and the paste retained and frozen at −80° C.

Table 12 shows expression results with strains STR57863 and STR57860 under several fermentation conditions. As shown, several of the initial strain/fermentation condition combinations resulted in >30% TCP asparaginase expression. Total cell protein was calculated as follows:

0.55 DCW total cell protein×500 µg/mL DCW at A550=275 µg total cell protein/ml (or mg/L) at A550=1

TCP at the final timepoint (I24)=OD575*275 mg/L TCP

Soluble % TCP=100*(soluble titer/TCP)

TABLE 12

2 L Fermentation Expression Results

| Strain Name | Induction Setpoints | | | Final OD575 | TCP at I24 (mg/L) | Soluble Titer (mg/L) | Insol. Titer (mg/L) | Total Titer (mg/L) | % soluble Titer | % soluble TCP |
| --- | --- | --- | --- | --- | --- | --- | --- | --- | --- | --- |
| | wcw g/g | pH | IPTG (mM) | | | | | | | |
| STR57863 | 0.4 | 6.5 | 0.2 | 197 | 54175 | 4652 | 745 | 5397 | 86.2 | 8.59 |
| | 0.4 | 7.2 | 0.08 | 218 | 59950 | 3879 | 756 | 4635 | 83.7 | 6.47 |
| | 0.2 | 7.2 | 0.2 | 217 | 59675 | 8518 | 1565 | 10083 | 84.5 | 14.27 |
| | 0.2 | 6.5 | 0.2 | 189 | 51975 | 24658 | 2329 | 26987 | 91.4 | 47.44 |
| | 0.2 | 6.5 | 0.08 | 221 | 60775 | 2863 | 837 | 3700 | 77.4 | 4.71 |
| | 0.4 | 7.2 | 0.2 | 221 | 60775 | 14245 | 1206 | 15451 | 92.2 | 23.44 |
| | 0.4 | 6.5 | 0.08 | 201 | 55275 | 8226 | 1137 | 9363 | 87.9 | 14.88 |
| STR57860 | 0.4 | 6.5 | 0.2 | 233 | 64075 | 18508 | 2166 | 20674 | 89.5 | 28.88 |
| | 0.4 | 7.2 | 0.08 | 218 | 59950 | 15241 | 1404 | 16645 | 91.6 | 25.42 |
| | 0.2 | 7.2 | 0.2 | 245 | 67375 | 21445 | 4700 | 26145 | 82.0 | 31.83 |
| | 0.2 | 6.5 | 0.08 | 168 | 46200 | 15478 | 3357 | 18835 | 82.2 | 33.50 |
| | 0.4 | 7.2 | 0.2 | 206 | 56650 | 34283 | 2226 | 36509 | 93.9 | 60.52 |
| | 0.2 | 7.2 | 0.08 | 228 | 62700 | 35301 | 2387 | 37688 | 93.7 | 56.30 |
| | 0.4 | 6.5 | 0.08 | 198 | 54450 | 30284 | 1903 | 32187 | 94.1 | 55.62 |

Example 5: 2 L Fermentation and Calculation of Soluble % TCP of Additional Expression Strains Additional strains constructed as described herein, e.g., additional strains described in Example 3, are scaled to 2 L fermentation and each screened under different fermentation conditions in a manner similar to that described in Example 4.

TABLE 13

Table of Sequences Listed

| Protein or Nucleic Acid | Sequence | SEQ ID NO: |
| --- | --- | --- |
| Mature E. coli A-1-3 L-Asparaginase Type II amino acid sequence (without secretion leader sequence) | LPNITILATGGTIAGGGDSATKSNYTAGKVGVENLVNAVPQLKDIANVKGEQVVN IGSQDMNDDVWLTLAKKINTDCDKTDGFVITHGTDTMEETAYFLDLTVKCDKPVV MVGAMRPSTSMSADGPFNLYNAVVTAADKASANRGVLVVMNDTVLDGRDVTKTNT TDVATFKSVNYGPLGYIHNGKIDYQRTPARKHTSDTPFDVSKLNELPKVGIVYNY ANASDLPAKALVDAGYDGIVSAGVGNGNLYKTVFDTLATAAKNGTAVVRSSRVPT GATTQDAEVDDAKYGFVASGTLNPQKARVLLQLALTQTKDPQQIQQIFNQY | 1 |

TABLE 13-continued

Table of Sequences Listed

| Protein or Nucleic Acid | Sequence | SEQ ID NO: |
|---|---|---|
| Optimized nucleic acid sequence encoding mature E. coli A-1-3 L-Asparaginase Type II amino acid sequence of SEQ ID NO: 1 | CTCCCTAACATTACTATTCTGGCCACTGGCGGTACGATTGCAGGCGGCGGTGACT CAGCCACCAAGTCGAATTACACCGCCGGTAAGGTCGGTGTCGAAAACCTCGTCAA CGCCGTGCCGCAGCTGAAAGATATCGCCAACGTCAAGGGCGAGCAAGTGGTGAAC ATCGGCTCCCAAGATATGAACGATGACGTGTGGCTGACGCTGGCCAAGAAAATCA ACACCGATTGCGACAAGACGGACGGGTTTGTCATCACCCACGGCACCGACACTAT GGAAGAGACTGCCTACTTCCTCGACCTCACGGTGAAGTGCGATAAACCGGTAGTG ATGGTGGGCGCCATGCGCCCGAGCACCTCGATGAGCGCGGACGGCCCGTTCAATC TGTACAACGCCGTGGTAACCGCAGCGGACAAGGCGTCCGCGAACCGCGGTGTATT GGTAGTGATGAACGATACGGTGCTCGATGGGCGCGATGTGACCAAGACCAATACC ACTGATGTGGCCACCTTCAAGAGCGTGAACTATGGCCCGCTGGGCTACATCCATA ACGGCAAGATCGATTACCAGCGTACTCCCGCCCGGAAGCACCTCGGACACCCC CTTCGACGTGTCGAAACTGAACGAACTGCCCAAGGTCGGCATCGTCTACAACTAC GCCAATGCGAGCGATCTGCCCGCGAAGGCCCTGGTGGACGCCGGCTACGACGGGA TCGTATCGGCGGGTGTGGGCAATGGTAACCTGTACAAGACCGTGTTTGACACCCT GGCGACGGCGGCGAAGAACGGCACCGCCGTGGTCCGCAGCAGCCGCGTGCCCACT GGGGCGACCACCCAAGACGCCGAGGTCGACGACGCGAAGTACGGCTTCGTAGCCA GCGGCACCCTGAACCCGCAAAAGGCCCGGGTCCTGCTGCAGCTGGCGCTCACGCA GACGAAGGACCCGCAGCAAATCCAACAGATCTTCAACCAGTAC | 2 |
| E. coli K-12 L-Asparaginase Type II amino acid sequence (includes native secretion leader, underlined) (GenBank M34277) | <u>MEFFKKTALAALVMGFSGAALA</u>LPNITILATGGTIAGGGDSATKSNYTVGKVGVE NLVNAVPQLKDIANVKGEQVVNIGSQDMNDNVWLTLAKKINTDCDKTDGFVITHG TDTMEETAYFLDLTVKCDKPVVMVGAMRPSTSMSADGPFNLYNAVVTAADKASAN RGVLVVMNDTVLDGRDVTKTNTTDVATFKSVNYGPLGYIHNGKIDYQRTPARKHT SDTPFDVSKLNELPKVGIVYNYANASDLPAKALVDAGYDGIVSAGVGNGNLYKSV FDTLATAAKTGTAVVRSSRVPTGATTQDAEVDDAKYGFVASGTLNPQKARVLLQL ALTQTKDPQQIQQIFNQY | 3 |
| E. coli K-12 Asparaginase Type II nucleic acid sequence (encoding SEQ ID NO: 3; including native secretion leader encoding sequence) | ATGGAGTTTTTCAAAAAGACGGCACTTGCCGCACTGGTTATGGGTTTTAGTGGTG CAGCATTGGCATTACCCAATATCACCATTTTAGCAACCGGCGGGACCATTGCCGG TGGTGGTGACTCCGCAACCAAATCTAACTACACAGTGGGTAAAGTTGGCGTAGAA AATCTGGTTAATGCGGTGCCGCAACTAAAAGACATTGCGAACGTTAAAGGCGAGC AGGTAGTGAATATCGGCTCCCAGGACATGAACGATAATGTCTGGCTGACACTGGC GAAAAAAATTAACACCGACTGCGATAAGACCGACGGCTTCGTCATTACCCACGGT ACCGACACGATGGAAGAAACTGCTTACTTCCTCGACCTGACGGTGAAATGCGACA AACCGGTGGTGATGGTCGGCGCAATGCGTCCGTCCACGTCTATGAGCGCAGACGG TCCATTCAACCTGTATAACGCGGTAGTGACCGCAGCTGATAAAGCCTCCGCCAAC CGTGGCGTGCTGGTAGTGATGAATGACACCGTGCTTGATGGCCGTGACGTCACCA AAACCAACACCACCGACGTAGCGACCTTCAAGTCTGTTAACTACGGTCCTCTGGG TTACATTCACAACGGTAAGATTGACTACCAGCGTACCCCGGCACGTAAGCATACC AGCGACACGCCATTCGATGTCTCTAAGCTGAATGAACTGCCCAAAGTCGGCATTG TTTATAACTACGCTAACGCATCCGATCTTCCGGCTAAAGCACTGGTAGATGCGGG CTATGATGGCATCGTTAGCGCTGGTGTGGGTAACGGCAACCTGTATAAATCTGTG TTCGACACGCTGGCGACCGCCGCGAAAACCGGTACTGCAGTCGTGCGTTCTTCCC GCGTACCGACGGGCGCTACCACTCAGGATGCCGAAGTGGATGATGCGAAATACGG CTTCGTCGCCTCTGGCACGCTGAACCCGCAAAAAGCGCGCGTTCTGCTGCAACTG GCTCTGACGCAAACCAAAGATCCGCAGCAGATCCAGCAGATCTTCAATCAGTACT AA | 4 |
| E. coli K-12 Asparaginase Type II amino acid sequence (excluding secretion leader) | LPNITILATGGTIAGGGDSATKSNYTVGKVGVENLVNAVPQLKDIANVKGEQVVN IGSQDMNDNVWLTLAKKINTDCDKTDGFVITHGTDTMEETAYFLDLTVKCDKPVV MVGAMRPSTSMSADGPFNLYNAVVTAADKASANRGVLVVMNDTVLDGRDVTKTNT TDVATFKSVNYGPLGYIHNGKIDYQRTPARKHTSDTPFDVSKLNELPKVGIVYNY ANASDLPAKALVDAGYDGIVSAGVGNGNLYKSVFDTLATAAKTGTAVVRSSRVPT GATTQDAEVDDAKYGFVASGTLNPQKARVLLQLALTQTKDPQQIQQIFNQY | 5 |
| E. coli A-1-3 Asparaginase Type II amino acid sequence (includes P. fluorescens AnsB secretion leader sequence, underlined) | <u>MKSALKNVIPGALALLLLFPVAAQA</u>LPNITILATGGTIAGGGDSATKSNYTAGKV GVENLVNAVPQLKDIANVKGEQVVNIGSQDMNDDVWLTLAKKINTDCDKTDGFVI THGTDTMEETAYFLDLTVKCDKPVVMVGAMRPSTSMSADGPFNLYNAVVTAADKA SANRGVLVVMNDTVLDGRDVTKTNTTDVATFKSVNYGPLGYIHNGKIDYQRTPAR KHTSDTPFDVSKLNELPKVGIVYNYANASDLPAKALVDAGYDGIVSAGVGNGNLY KTVFDTLATAAKNGTAVVRSSRVPTGATTQDAEVDDAKYGFVASGTLNPQKARVL LQLALTQTKDPQQIQQIFNQY | 6 |
| E. coli A-1-3 Asparaginase Type II amino | <u>MRQLFFCLMLMVSLTAHAL</u>PNITILATGGTIAGGGDSATKSNYTAGKVGVENLVN AVPQLKDIANVKGEQVVNIGSQDMNDDVWLTLAKKINTDCDKTDGFVITHGTDTM EETAYFLDLTVKCDKPVVMVGAMRPSTSMSADGPFNLYNAVVTAADKASANRGVL | 7 |

TABLE 13-continued

Table of Sequences Listed

| Protein or Nucleic Acid | Sequence | SEQ ID NO: |
|---|---|---|
| acid sequence (includes 8484 secretion leader sequence, underlined) | VVMNDTVLDGRDVTKTNTTDVATFKSVNYGPLGYIHNGKIDYQRTPARKHTSDTP FDVSKLNELPKVGIVYNYANASDLPAKALVDAGYDGIVSAGVGNGNLYKTVFDTL ATAAKNGTAVVRSSRVPTGATTQDAEVDDAKYGFVASGTLNPQKARVLLQLALTQ TKDPQQIQQIFNQY | |
| E. coli A-1-3 Asparaginase Type II amino acid sequence (includes Ibp-S31A secretion leader sequence, underlined) | <u>MIRDNRLKTSLLRGLTLTLLSLTLLSPAAHAL</u>PNITILATGGTIAGGGDSATKSN YTAGKVGVENLVNAVPQLKDIANVKGEQVVNIGSQDMNDDVWLTLAKKINTDCDK TDGFVITHGTDTMEETAYFLDLTVKCDKPVVMVGAMRPSTSMSADGPFNLYNAVV TAADKASANRGVLVVMNDTVLDGRDVTKTNTTDVATFKSVNYGPLGYIHNGKIDY QRTPARKHTSDTPFDVSKLNELPKVGIVYNYANASDLPAKALVDAGYDGIVSAGV GNGNLYKTVFDTLATAAKNGTAVVRSSRVPTGATTQDAEVDDAKYGFVASGTLNP QKARVLLQLALTQTKDPQQIQQIFNQY | 8 |
| E. coli A-1-3 Asparaginase Type II amino acid sequence (includes pbp secretion leader sequence, underlined) | <u>MKLKRLMAAMTFVAAGVATANAVAL</u>PNITILATGGTIAGGGDSATKSNYTAGKVG VENLVNAVPQLKDIANVKGEQVVNIGSQDMNDDVWLTLAKKINTDCDKTDGFVIT HGTDTMEETAYFLDLTVKCDKPVVMVGAMRPSTSMSADGPFNLYNAVVTAADKAS ANRGVLVVMNDTVLDGRDVTKTNTTDVATFKSVNYGPLGYIHNGKIDYQRTPARK HTSDTPFDVSKLNELPKVGIVYNYANASDLPAKALVDAGYDGIVSAGVGNGNLYK TVFDTLATAAKNGTAVVRSSRVPTGATTQDAEVDDAKYGFVASGTLNPQKARVLL QLALTQTKDPQQIQQIFNQY | 9 |
| E. coli A-1-3 Asparaginase Type II amino acid sequence (includes LAO secretion leader sequence, underlined) | <u>MQNYKKFLLAAAVSMAFSATAMAL</u>PNITILATGGTIAGGGDSATKSNYTAGKVGV ENLVNAVPQLKDIANVKGEQVVNIGSQDMNDDVWLTLAKKINTDCDKTDGFVITH GTDTMEETAYFLDLTVKCDKPVVMVGAMRPSTSMSADGPFNLYNAVVTAADKASA NRGVLVVMNDTVLDGRDVTKTNTTDVATFKSVNYGPLGYIHNGKIDYQRTPARKH TSDTPFDVSKLNELPKVGIVYNYANASDLPAKALVDAGYDGIVSAGVGNGNLYKT VFDTLATAAKNGTAVVRSSRVPTGATTQDAEVDDAKYGFVASGTLNPQKARVLLQ LALTQTKDPQQIQQIFNQY | 10 |
| E. coli A-1-3 Asparaginase Type II amino acid sequence (includes Azurin secretion leader sequence, underlined) | <u>MFAKLVAVSLLTLASGQLLAL</u>PNITILATGGTIAGGGDSATKSNYTAGKVGVENL VNAVPQLKDIANVKGEQVVNIGSQDMNDDVWLTLAKKINTDCDKTDGFVITHGTD TMEETAYFLDLTVKCDKPVVMVGAMRPSTSMSADGPFNLYNAVVTAADKASANRG VLVVMNDTVLDGRDVTKTNTTDVATFKSVNYGPLGYIHNGKIDYQRTPARKHTSD TPFDVSKLNELPKVGIVYNYANASDLPAKALVDAGYDGIVSAGVGNGNLYKTVFD TLATAAKNGTAVVRSSRVPTGATTQDAEVDDAKYGFVASGTLNPQKARVLLQLAL TQTKDPQQIQQIFNQY | 11 |
| E. coli A-1-3 Asparaginase Type II amino acid sequence (includes PbpA20V secretion leader sequence, underlined) | <u>MKLKRLMAAMTFVAAGVATVNAVAL</u>PNITILATGGTIAGGGDSATKSNYTAGKVG VENLVNAVPQLKDIANVKGEQVVNIGSQDMNDDVWLTLAKKINTDCDKTDGFVIT HGTDTMEETAYFLDLTVKCDKPVVMVGAMRPSTSMSADGPFNLYNAVVTAADKAS ANRGVLVVMNDTVLDGRDVTKTNTTDVATFKSVNYGPLGYIHNGKIDYQRTPARK HTSDTPFDVSKLNELPKVGIVYNYANASDLPAKALVDAGYDGIVSAGVGNGNLYK TVFDTLATAAKNGTAVVRSSRVPTGATTQDAEVDDAKYGFVASGTLNPQKARVLL QLALTQTKDPQQIQQIFNQY | 12 |
| E. coli A-1-3 Asparaginase Type II amino acid sequence (includes CupC2 secretion leader sequence, underlined) | <u>MPPRSIAACLGLLGLLMATQAAAL</u>PNITILATGGTIAGGGDSATKSNYTAGKVGV ENLVNAVPQLKDIANVKGEQVVNIGSQDMNDDVWLTLAKKINTDCDKTDGFVITH GTDTMEETAYFLDLTVKCDKPVVMVGAMRPSTSMSADGPFNLYNAVVTAADKASA NRGVLVVMNDTVLDGRDVTKTNTTDVATFKSVNYGPLGYIHNGKIDYQRTPARKH TSDTPFDVSKLNELPKVGIVYNYANASDLPAKALVDAGYDGIVSAGVGNGNLYKT VFDTLATAAKNGTAVVRSSRVPTGATTQDAEVDDAKYGFVASGTLNPQKARVLLQ LALTQTKDPQQIQQIFNQY | 13 |

TABLE 13-continued

Table of Sequences Listed

| Protein or Nucleic Acid | Sequence | SEQ ID NO: |
|---|---|---|
| AnsB secretion leader amino acid sequence (*P. fluorescens* Asparaginase Type II native secretion leader) | MKSALKNVIPGALALLLLFPVAAQA | 14 |
| AnsB secretion leader nucleic acid sequence (*P. fluorescens* Asparaginase Type II native secretion leader) | ATGAAATCTGCATTGAAGAACGTTATTCCGGGCGCCCTGGCCCTTCTGCTGCTAT TCCCCGTCGCCGCCCAGGCA | 15 |
| 8484 secretion leader amino acid sequence (*P. fluorescens*) | MRQLFFCLMLMVSLTAHA | 16 |
| 8484 secretion leader nucleic acid sequence (*P. fluorescens*) | ATGCGACAACTATTTTTCTGTTTGATGCTGATGGTGTCGCTCACGGCGCACGCC | 17 |
| Ibp-S31A secretion leader amino acid sequence (*P. fluorescens*) | MIRDNRLKTSLLRGLTLTLLSLTLLSPAAHA | 18 |
| Ibp-S31A secretion leader nucleic acid sequence (*P. fluorescens*) | ATGATCCGTGACAACCGACTCAAGACATCCCTTCTGCGCGGCCTGACCCTCACCC TACTCAGCCTGACCCTGCTCTCGCCCGCGGCCCATGCC | 19 |
| Pbp secretion leader amino acid sequence (*P. fluorescens*) | MKLKRLMAAMTFVAAGVATANAVA | 20 |
| Pbp secretion leader nucleic acid sequence (*P. fluorescens*) | ATGAAACTGAAACGTTTGATGGCGGCAATGACTTTTGTCGCTGCTGGCGTTGCGA CCGCCAACGCGGTGGCC | 21 |
| LAO secretion leader amino acid sequence (*P. fluorescens*) | MQNYKKFLLAAAVSMAFSATAMA | 22 |
| LAO secretion leader nucleic acid sequence (*P. fluorescens*) | ATGCAGAACTATAAAAAATTCCTTCTGGCCGCGGCCGTCTCGATGGCGTTCAGCG CCACGGCCATGGCA | 23 |
| Azurin secretion leader amino acid sequence (*P. fluorescens*) | MFAKLVAVSLLTLASGQLLA | 24 |

TABLE 13-continued

Table of Sequences Listed

| Protein or Nucleic Acid | Sequence | SEQ ID NO: |
|---|---|---|
| Azurin secretion leader nucleic acid sequence (*P. fluorescens*) | ATGTTTGCCAAACTCGTTGCTGTTTCCCTGCTGACTCTGGCGAGCGGCCAGTTGCTTGCT | 25 |
| PbpA20V secretion leader amino acid sequence (*P. fluorescens*) | MKLKRLMAAMTFVAAGVATVNAVA | 26 |
| PbpA20V secretion leader nucleic acid sequence (*P. fluorescens*) | ATGAAACTGAAACGTTTGATGGCGGCAATGACTTTTGTCGCTGCTGGCGTTGCGACCGTCAACGCGGTGGCC | 27 |
| CupC2 secretion leader amino acid sequence (*P. fluorescens*) | MPPRSIAACLGLLGLLMATQAAA | 28 |
| CupC2 secretion leader nucleic acid sequence (*P. fluorescens*) | ATGCCGCCTCGTTCTATCGCCGCATGTCTGGGGCTGCTGGGCTTGCTCATGGCTACCCAGGCCGCCGCC | 29 |
| *E. coli* K-12 AnsB secretion leader amino acid sequence | MEFFKKTALAALVMGFSGAALA | 30 |
| Ttg2C secretion leader amino acid sequence (*P. fluorescens*) | MQNRTVEIGVGLFLLAGILALLLLALRVSGLSA | 31 |
| Ttg2C secretion leader nucleic acid sequence (*P. fluorescens*) | ATGCAAAACCGCACTGTGGAAATCGGTGTCGGCCTTTTCTTGCTGGCTGGCATCCTGGCTTTACTGTTGTTGGCCCTGCGAGTCAGCGGCCTTTCGGCC | 32 |
| Tpr secretion leader amino acid sequence (*P. fluorescens*) | MNRSSALLLAFVFLSGCQAMA | 33 |
| Tpr secretion leader nucleic acid sequence (*P. fluorescens*) | ATGAATAGATCTTCCGCGTTGCTCCTCGCTTTTGTCTTCCTCAGCGGCTGCCAGGCCATGGCC | 34 |
| DsbC secretion leader amino acid sequence (*P. fluorescens*) | MRLTQIIAAAAIALVSTFALA | 35 |

TABLE 13-continued

Table of Sequences Listed

| Protein or Nucleic Acid | Sequence | SEQ ID NO: |
|---|---|---|
| DsbC secretion leader nucleic acid sequence (*P. fluorescens*) | ATGCGCTTGACCCAGATTATTGCCGCCGCAGCCATTGCGTTGGTTTCCACCTTTGCGCTCGCC | 36 |
| 5193 secretion leader amino acid sequence (*P. fluorescens*) | MQSLPFSALRLLGVLAVMVCVLLTTPARA | 37 |
| 5193 secretion leader nucleic acid sequence (*P. fluorescens*) | ATGCAAAGCCTGCCGTTCTCTGCGTTACGCCTGCTCGGTGTGCTGGCAGTCATGGTCTGCGTGCTGTTGACGACGCCAGCCCGTGCC | 38 |
| DsbA secretion leader amino acid sequence (*P. fluorescens*) | MRNLILSAALVTASLFGMTAQA | 39 |
| DsbA secretion leader nucleic acid sequence (*P. fluorescens*) | ATGCGTAATCTGATCCTCAGCGCCGCTCTCGTCACTGCCAGCCTCTTCGGCATGACCGCACAAGCT | 40 |
| TolB secretion leader amino acid sequence (*P. fluorescens*) | MRNLLRGMLVVICCMAGIAAA | 41 |
| TolB secretion leader nucleic acid sequence (*P. fluorescens*) | ATGAGAAACCTTCTTCGAGGAATGCTTGTCGTTATTTGCTGTATGGCAGGGATAGCGGCGGCG | 42 |
| CupB2 secretion leader amino acid sequence (*P. fluorescens*) | MLFRTLLASLTFAVIAGLPSTAHA | 43 |
| CupB2 secretion leader nucleic acid sequence (*P. fluorescens*) | ATGCTTTTTCGCACATTACTGGCGAGCCTTACCTTTGCTGTCATCGCCGGCTTACCGTCCACGGCCCACGCG | 44 |
| Consensus RBS (high binding strength) | AGGAGG | 45 |
| RBS2 | GGAGCG | 46 |
| RBS34 | GGAGCG | 47 |
| RBS41 | AGGAGT | 48 |
| RBS43 | GGAGTG | 49 |
| RBS48 | GAGTAA | 50 |
| RBS1 | AGAGAG | 51 |

TABLE 13-continued

Table of Sequences Listed

| Protein or Nucleic Acid | Sequence | SEQ ID NO: |
|---|---|---|
| RBS35 | AAGGCA | 52 |
| RBS49 | CCGAAC | 53 |
| AspG1 Amino Acid Sequence (*P. fluorescens*; RXF08567; peg5048) | MQSANNVMVLYTGGTIGMQASANGLAPASGFEVRMREQFAGADLPAWRFQEMSPL IDSANMNPAYWQRLRSAVVEAVDAGCDAVLILHGTDTLAYSAAAMSFQLLGLPAP VVFTGSMLPAGVPDSDAWENVSGALTALGEGLKPGVHLYFHGALMAPTRCAKIRS FGRNPFAALQRNGGVALADKLPAALAYRNDKAPANVGVLPLVPGIAAAQLDALID SGIQALVLECFGSGTGPSDNPAFLASLKRAQDQEVVVVAITQCHEGGVELDVYEA GSRLRSVGVLSGGGMTREAAFGKLNALIGAGLDSAEIRRLVELDLCGELS | 54 |
| AspG2 Amino Acid Sequence (*P. fluorescens*; (RXF05674; peg3886) (sequence includes *P. fluorescens* AnsB secretion leader sequence, underlined) | <u>MKSALKNVIPGALALLLLFPVAAQA</u>KEVESKTKLSNVVILATGGTIAGAGASAAN SATYQAAKVGIEQLIAGVPELSQIANVRGEQVMQIASESINNENLLQLGRRVAEL ADNKDVDGIVITHGTDTLEETAYFLNLVEKTDKPIVVVGSMRPGTAMSADGMLNL YNAVAVAGSKEARGKGVLVTMNDEIQSGRDVSKMINIKTEAFKSPWGPMGMVVEG KSYWFRLPAKRHTMDSEFDIKTIKSLPDVEIAYGYGNVSDTAYKALAQAGAKAII HAGTGNGSVSSKVVPALVELRKQGVQIIRSSHVNAGGMVLRNAEQPDDKYDWVAA LDLNPQKARILAMVALTKTQDSKELQRIFWEY | 55 |
| Skp (ompH) RXF04702.1 Amino Acid Sequence (*P. fluorescens*) | VRKLTQLVLLATVLVTTPAFAEMKIAVLNYQMALLESDAAKRYAVDAEKKFGPQL TKLKTLESSAKGIQDRLVAGGDKMQQGERERLELEFKQKARDYQFQSKELNEAKA VADREMLKQLKPKLDSAVEEVIKKGAFDLVFERGAVIDVKPQYDITRQVIERMNQ LK | 56 |
| Skp (ompH) RXF04702.1 Nucleic acid sequence (*P. fluorescens*) | GTGCGTAAGTTGACTCAATTGGTCTTGCTGGCCACTGTGCTGGTCACCACCCCGG CCTTCGCCGAAATGAAAATCGCCGTTCTGAACTATCAGATGGCCCTGCTGGAATC CGATGCGGCCAAGCGATACGCCGTGGATGCCGAGAAGAAGTTCGGTCCGCAACTG ACCAAGCTCAAGACACTGGAAAGCAGCGCCAAAGGCATCCAGGACCGCCTGGTAG CCGGTGGCGACAAGATGCAGCAAGGCGAGCGCGAGCGTCTGGAGCTTGAATTCAA GCAAAAGGCCCGTGACTACCAGTTCCAATCCAAGGAGCTGAACGAAGCCAAGGCT GTGGCCGACCGCGAAATGCTCAAGCAGCTCAAGCCTAAATTGGACAGCGCTGTGG AAGAAGTCATCAAGAAGGGTGCCTTTGACCTGGTGTTCGAGCGTGGCGCCGTGAT CGACGTCAAGCCTCAATACGACATCACCCGCCAGGTGATCGAGCGCATGAACCAG CTGAAGTGA | 57 |

While preferred embodiments of the present disclosure have been shown and described herein, such embodiments are provided by way of example only. Numerous variations, changes, and substitutions will now occur to those skilled in the art without departing from the disclosure. It should be understood that various alternatives to the embodiments of the disclosure described herein may be employed in practicing the methods herein. It is intended that the following claims define the scope of the invention and that methods and structures within the scope of these claims and their equivalents be covered thereby.

What is claimed is:

1. A method for producing a recombinant type II asparaginase, the method comprising:
culturing a Pseudomonadales host cell in a culture medium and expressing the recombinant type II asparaginase in the periplasm of the Pseudomonadales host cell from an expression construct comprising a nucleic acid encoding the recombinant type II asparaginase; wherein the recombinant type II asparaginase encoded by the nucleic acid comprises an amino acid sequence at least 85% homologous to SEQ ID NO: 1, and wherein the recombinant type II asparaginase is produced in the periplasm at a yield of about 33% to about 60% total cell protein (TCP) in soluble form.

2. The method of claim 1, wherein the soluble recombinant type II asparaginase is produced in the periplasm at a yield of about 10 g/L to about 38 g/L.

3. The method of claim 1, further comprising measuring the activity of an amount of the recombinant type II asparaginase produced, using an activity assay.

4. The method of claim 1, wherein the nucleic acid encoding the recombinant type II asparaginase is optimized for expression in the host cell.

5. The method of claim 1, wherein the recombinant type II asparaginase is an *Escherichia coli* L-asparaginase type II.

6. The method of claim 1, wherein the nucleic acid encoding the recombinant type II asparaginase comprises a sequence at least 85% homologous to SEQ ID NO: 2 or SEQ ID NO: 4.

7. The method of claim 1, wherein the recombinant type II asparaginase encoded by the nucleic acid comprises an amino acid sequence as set forth in SEQ ID NO: 1.

8. The method of claim 1, wherein the Pseudomonadales host cell is a *Pseudomonas fluorescens* cell.

9. The method of claim 1, wherein the host cell is deficient in the expression of one or more native asparaginases.

10. The method of claim 9, wherein the one or more deficiently expressed native asparaginase is selected from: a type I asparaginase; a type II asparaginase; and a combination thereof.

11. The method of claim 1, wherein the host cell is deficient in the expression of one or more proteases.

12. The method of claim 1, wherein the host cell overexpresses one or more folding modulators.

13. The method of claim 1, wherein the host cell is selected from:
   a) a host cell that overexpresses LepB;
   b) a host cell that overexpresses Tig;
   c) a host cell that overexpresses DsbAC-Skp;
   d) a host cell that is deficient in Lon, HslUV, DegP1, DegP2, DegP2 S219A, Prc1, or AprA;
   e) a host cell that is deficient in AspG1;
   f) a host cell that is deficient in AspG2;
   g) a host cell that does not overexpress a folding modulator, and is not deficient in a protease;
   h) a host cell that does not overexpress a folding modulator, is not deficient in a protease; and is not deficient in AspG1;
   i) a host cell that does not overexpress a folding modulator, is not deficient in a protease; and is not deficient in AspG2; and
   j) a host cell that does not overexpress a folding modulator, is not deficient in a protease; and is not deficient in AspG1 or AspG2.

14. The method of claim 1, wherein the host cell is selected from:
   a) a host cell that is deficient in Lon and HslUV;
   b) a host cell that is deficient in Lon, DegP1, DegP2, Prc1, and AprA;
   c) a host cell that is deficient in Lon, DegP1, DegP2 S219A, Prc1, and AprA, and overexpresses DsbAC-Skp;
   d) a host cell that is deficient in AspG1 and/or AspG2;
   e) a host cell that is deficient in AspG1 and/or AspG2, and overexpresses Tig;
   f) a host cell that is deficient in AspG1 and/or AspG2, and overexpresses LepB;
   g) a host cell that is deficient in AspG1 and/or AspG2, and deficient in Lon and HslUV
   h) a host cell that is deficient in AspG1 and/or AspG2, and deficient in Lon, DegP1, DegP2, Prc1, and AprA; and
   i) a host cell that is deficient in AspG1 and/or AspG2, Lon, DegP1, DegP2, Prc1, and AprA, and overexpresses DsbAC-Skp.

15. The method of claim 1, wherein the expression construct comprises a secretion leader.

16. The method of claim 15, wherein the secretion leader directs transfer of the recombinant type II asparaginase produced to the periplasm of the host cell.

17. The method of claim 15, wherein the secretion leader is selected from the following group of secretion leaders: *P. fluorescens* AnsB, 8484, IBP-S31A, pbp, 8584, LAO, Azu, PbpA20V, CupC2, and *Escherichia coli* K-12 AnsB.

18. The method of claim 3, further comprising comparing the measured activity of the recombinant type II asparaginase produced with an activity measured in the same amount of a control type II asparaginase using the same activity assay, wherein the measured activity of the recombinant type II asparaginase produced is comparable to the activity of the control type II asparaginase.

19. The method of claim 1, wherein the recombinant type II asparaginase produced is modified to increase half-life in patients.

20. The method of claim 17, wherein the nucleic acid encodes the recombinant type II asparaginase operably linked to the *P. fluorescens* AnsB secretion leader, and wherein the recombinant type II asparaginase is produced in the periplasm at a yield that is about 20% to about 100% greater than that of a recombinant *P. fluorescens* type II asparaginase produced in the periplasm by the same method, wherein the *P. fluorescens* type II asparaginase is expressed from a second expression construct comprising a nucleic acid encoding the recombinant *P. fluorescens* type II asparaginase operably linked to the *P. fluorescens* AnsB secretion leader.

21. The method of claim 20, wherein the second expression construct comprises a nucleic acid encoding the amino acid sequence set forth as SEQ ID NO: 55.

22. The method of claim 1, wherein the nucleic acid encoding the recombinant type II asparaginase comprises a sequence as set forth in SEQ ID NO: 2 or SEQ ID NO: 4.

23. The method of claim 1, wherein the recombinant type II asparaginase encoded by the nucleic acid comprises an amino acid sequence as set forth in SEQ ID NO: 5.

24. The method of claim 23, wherein the recombinant type II asparaginase encoded by the nucleic acid comprises an amino acid sequence as set forth in SEQ ID NO: 6.

* * * * *

SEQUENCE LISTING

```
<160> NUMBER OF SEQ ID NOS: 57

<210> SEQ ID NO 1
<211> LENGTH: 326
<212> TYPE: PRT
<213> ORGANISM: Escherichia coli

<400> SEQUENCE: 1

Leu Pro Asn Ile Thr Ile Leu Ala Thr Gly Gly Thr Ile Ala Gly Gly
1               5                   10                  15

Gly Asp Ser Ala Thr Lys Ser Asn Tyr Thr Ala Gly Lys Val Gly Val
                20                  25                  30

Glu Asn Leu Val Asn Ala Val Pro Gln Leu Lys Asp Ile Ala Asn Val
            35                  40                  45
```

Lys Gly Glu Gln Val Val Asn Ile Gly Ser Gln Asp Met Asn Asp Asp
        50                  55                  60

Val Trp Leu Thr Leu Ala Lys Lys Ile Asn Thr Asp Cys Asp Lys Thr
 65                  70                  75                  80

Asp Gly Phe Val Ile Thr His Gly Thr Asp Thr Met Glu Glu Thr Ala
                85                  90                  95

Tyr Phe Leu Asp Leu Thr Val Lys Cys Asp Lys Pro Val Val Met Val
            100                 105                 110

Gly Ala Met Arg Pro Ser Thr Ser Met Ser Ala Asp Gly Pro Phe Asn
        115                 120                 125

Leu Tyr Asn Ala Val Val Thr Ala Ala Asp Lys Ala Ser Ala Asn Arg
    130                 135                 140

Gly Val Leu Val Val Met Asn Asp Thr Val Leu Asp Gly Arg Asp Val
145                 150                 155                 160

Thr Lys Thr Asn Thr Thr Asp Val Ala Thr Phe Lys Ser Val Asn Tyr
                165                 170                 175

Gly Pro Leu Gly Tyr Ile His Asn Gly Lys Ile Asp Tyr Gln Arg Thr
            180                 185                 190

Pro Ala Arg Lys His Thr Ser Asp Thr Pro Phe Asp Val Ser Lys Leu
        195                 200                 205

Asn Glu Leu Pro Lys Val Gly Ile Val Tyr Asn Tyr Ala Asn Ala Ser
    210                 215                 220

Asp Leu Pro Ala Lys Ala Leu Val Asp Ala Gly Tyr Asp Gly Ile Val
225                 230                 235                 240

Ser Ala Gly Val Gly Asn Gly Asn Leu Tyr Lys Thr Val Phe Asp Thr
                245                 250                 255

Leu Ala Thr Ala Ala Lys Asn Gly Thr Ala Val Val Arg Ser Ser Arg
            260                 265                 270

Val Pro Thr Gly Ala Thr Thr Gln Asp Ala Glu Val Asp Asp Ala Lys
        275                 280                 285

Tyr Gly Phe Val Ala Ser Gly Thr Leu Asn Pro Gln Lys Ala Arg Val
    290                 295                 300

Leu Leu Gln Leu Ala Leu Thr Gln Thr Lys Asp Pro Gln Gln Ile Gln
305                 310                 315                 320

Gln Ile Phe Asn Gln Tyr
                325

<210> SEQ ID NO 2
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctccctaaca ttactattct ggccactggc ggtacgattg caggcggcgg tgactcagcc     60
accaagtcga attacaccgc cggtaaggtc ggtgtcgaaa acctcgtcaa cgccgtgccg    120
cagctgaaag atatcgccaa cgtcaagggc gagcaagtgg tgaacatcgg ctcccaagat    180
atgaacgatg acgtgtggct gacgctggcc aagaaaatca caccgattgc gacaagacg     240 gacgggtttg tcatcaccca cggcaccgac actatggaag agactgccta cttcctcgac    300
ctcacggtga agtgcgataa accggtagtg atggtgggcg ccatgcgccc gagcacctcg    360
atgagcgcgg acggcccgtt caatctgtac aacgccgtgg taaccgcagc ggacaaggcg    420

```
tccgcgaacc gcggtgtatt ggtagtgatg aacgatacgg tgctcgatgg gcgcgatgtg    480
accaagacca ataccactga tgtggccacc ttcaagagcg tgaactatgg cccgctgggc    540
tacatccata acggcaagat cgattaccag cgtactcccg cccggaagca cacctcggac    600
acccccttcg acgtgtcgaa actgaacgaa ctgcccaagg tcggcatcgt ctacaactac    660
gccaatgcga gcgatctgcc cgcgaaggcc ctggtggacg ccggctacga cgggatcgta    720
tcggcgggtg tgggcaatgg taacctgtac aagaccgtgt tgacaccct ggcgacggcg    780 gcgaagaacg gcaccgccgt ggtccgcagc agccgcgtgc ccactggggc gaccacccaa    840
gacgccgagg tcgacgacgc gaagtacggc ttcgtagcca gcggcaccct gaacccgcaa    900
aaggcccggg tcctgctgca gctggcgctc acgcagacga aggacccgca gcaaatccaa    960
cagatcttca accagtac                                                  978

<210> SEQ ID NO 3
<211> LENGTH: 348
<212> TYPE: PRT
<213> ORGANISM: Escherichia coli

<400> SEQUENCE: 3

Met Glu Phe Phe Lys Lys Thr Ala Leu Ala Ala Leu Val Met Gly Phe
1               5                   10                  15

Ser Gly Ala Ala Leu Ala Leu Pro Asn Ile Thr Ile Leu Ala Thr Gly
                20                  25                  30

Gly Thr Ile Ala Gly Gly Gly Asp Ser Ala Thr Lys Ser Asn Tyr Thr
            35                  40                  45

Val Gly Lys Val Gly Val Glu Asn Leu Val Asn Ala Val Pro Gln Leu
        50                  55                  60

Lys Asp Ile Ala Asn Val Lys Gly Glu Gln Val Val Asn Ile Gly Ser
65                  70                  75                  80

Gln Asp Met Asn Asp Asn Val Trp Leu Thr Leu Ala Lys Lys Ile Asn
                85                  90                  95

Thr Asp Cys Asp Lys Thr Asp Gly Phe Val Ile Thr His Gly Thr Asp
            100                 105                 110

Thr Met Glu Glu Thr Ala Tyr Phe Leu Asp Leu Thr Val Lys Cys Asp
        115                 120                 125

Lys Pro Val Val Met Val Gly Ala Met Arg Pro Ser Thr Ser Met Ser
    130                 135                 140

Ala Asp Gly Pro Phe Asn Leu Tyr Asn Ala Val Val Thr Ala Ala Asp
145                 150                 155                 160

Lys Ala Ser Ala Asn Arg Gly Val Leu Val Val Met Asn Asp Thr Val
                165                 170                 175

Leu Asp Gly Arg Asp Val Thr Lys Thr Asn Thr Thr Asp Val Ala Thr
            180                 185                 190

Phe Lys Ser Val Asn Tyr Gly Pro Leu Gly Tyr Ile His Asn Gly Lys
        195                 200                 205

Ile Asp Tyr Gln Arg Thr Pro Ala Arg Lys His Thr Ser Asp Thr Pro
    210                 215                 220

Phe Asp Val Ser Lys Leu Asn Glu Leu Pro Lys Val Gly Ile Val Tyr
225                 230                 235                 240

Asn Tyr Ala Asn Ala Ser Asp Leu Pro Ala Lys Ala Leu Val Asp Ala
                245                 250                 255

Gly Tyr Asp Gly Ile Val Ser Ala Gly Val Gly Asn Gly Asn Leu Tyr
            260                 265                 270
```

-continued

```
Lys Ser Val Phe Asp Thr Leu Ala Thr Ala Ala Lys Thr Gly Thr Ala
        275                 280                 285

Val Val Arg Ser Ser Arg Val Pro Thr Gly Ala Thr Thr Gln Asp Ala
    290                 295                 300

Glu Val Asp Asp Ala Lys Tyr Gly Phe Val Ala Ser Gly Thr Leu Asn
305                 310                 315                 320

Pro Gln Lys Ala Arg Val Leu Leu Gln Leu Ala Leu Thr Gln Thr Lys
                325                 330                 335

Asp Pro Gln Gln Ile Gln Gln Ile Phe Asn Gln Tyr
            340                 345

<210> SEQ ID NO 4
<211> LENGTH: 1047
<212> TYPE: DNA
<213> ORGANISM: Escherichia coli

<400> SEQUENCE: 4
atggagtttt tcaaaaagac ggcacttgcc gcactggtta tgggttttag tggtgcagca     60
ttggcattac ccaatatcac cattttagca accggcggga ccattgccgg tggtggtgac    120
tccgcaacca aatctaacta cacagtgggt aaagttggcg tagaaaatct ggttaatgcg    180
gtgccgcaac taaaagacat tgcgaacgtt aaaggcgagc aggtagtgaa tatcggctcc    240
caggacatga acgataatgt ctggctgaca ctggcgaaaa aaattaacac cgactgcgat    300
aagaccgacg gcttcgtcat tacccacggt accgacacga tggaagaaac tgcttacttc    360
ctcgacctga cggtgaaatg cgacaaaccg gtggtgatgg tcggcgcaat gcgtccgtcc    420
acgtctatga gcgcagacgg tccattcaac ctgtataacg cggtagtgac cgcagctgat    480
aaagcctccg ccaaccgtgg cgtgctggta gtgatgaatg acaccgtgct tgatggccgt    540
gacgtcacca aaaccaacac caccgacgta gcgaccttca agtctgttaa ctacggtcct    600
ctgggttaca ttcacaacgg taagattgac taccagcgta ccccggcacg taagcatacc    660
agcgacacgc cattcgatgt ctctaagctg aatgaactgc cgaaagtcgg cattgtttat    720
aactacgcta acgcatccga tcttccggct aaagcactgg tagatgcggg ctatgatggc    780
atcgttagcg ctggtgtggg taacggcaac ctgtataaat ctgtgttcga cacgctggcg    840
accgccgcga aaaccggtac tgcagtcgtg cgttcttccc gcgtaccgac gggcgctacc    900
actcaggatg ccgaagtgga tgatgcgaaa tacggcttcg tcgcctctgg cacgctgaac    960
ccgcaaaaag cgcgcgttct gctgcaactg gctctgacgc aaaccaaaga tccgcagcag   1020
atccagcaga tcttcaatca gtactaa                                       1047

<210> SEQ ID NO 5
<211> LENGTH: 326
<212> TYPE: PRT
<213> ORGANISM: Escherichia coli

<400> SEQUENCE: 5

Leu Pro Asn Ile Thr Ile Leu Ala Thr Gly Gly Thr Ile Ala Gly Gly
1               5                   10                  15

Gly Asp Ser Ala Thr Lys Ser Asn Tyr Thr Val Gly Lys Val Gly Val
            20                  25                  30

Glu Asn Leu Val Asn Ala Val Pro Gln Leu Lys Asp Ile Ala Asn Val
        35                  40                  45

Lys Gly Glu Gln Val Val Asn Ile Gly Ser Gln Asp Met Asn Asp Asn
    50                  55                  60
```

Val Trp Leu Thr Leu Ala Lys Lys Ile Asn Thr Asp Cys Asp Lys Thr
65                  70                  75                  80

Asp Gly Phe Val Ile Thr His Gly Thr Asp Thr Met Glu Glu Thr Ala
                85                  90                  95

Tyr Phe Leu Asp Leu Thr Val Lys Cys Asp Lys Pro Val Met Val
            100                 105                 110

Gly Ala Met Arg Pro Ser Thr Ser Met Ser Ala Asp Gly Pro Phe Asn
            115                 120                 125

Leu Tyr Asn Ala Val Val Thr Ala Ala Asp Lys Ala Ser Ala Asn Arg
130                 135                 140

Gly Val Leu Val Val Met Asn Asp Thr Val Leu Asp Gly Arg Asp Val
145                 150                 155                 160

Thr Lys Thr Asn Thr Thr Asp Val Ala Thr Phe Lys Ser Val Asn Tyr
                165                 170                 175

Gly Pro Leu Gly Tyr Ile His Asn Gly Lys Ile Asp Tyr Gln Arg Thr
            180                 185                 190

Pro Ala Arg Lys His Thr Ser Asp Thr Pro Phe Asp Val Ser Lys Leu
            195                 200                 205

Asn Glu Leu Pro Lys Val Gly Ile Val Tyr Asn Tyr Ala Asn Ala Ser
210                 215                 220

Asp Leu Pro Ala Lys Ala Leu Val Asp Ala Gly Tyr Asp Gly Ile Val
225                 230                 235                 240

Ser Ala Gly Val Gly Asn Gly Asn Leu Tyr Lys Ser Val Phe Asp Thr
            245                 250                 255

Leu Ala Thr Ala Ala Lys Thr Gly Thr Ala Val Val Arg Ser Ser Arg
            260                 265                 270

Val Pro Thr Gly Ala Thr Thr Gln Asp Ala Glu Val Asp Asp Ala Lys
            275                 280                 285

Tyr Gly Phe Val Ala Ser Gly Thr Leu Asn Pro Gln Lys Ala Arg Val
            290                 295                 300

Leu Leu Gln Leu Ala Leu Thr Gln Thr Lys Asp Pro Gln Gln Ile Gln
305                 310                 315                 320

Gln Ile Phe Asn Gln Tyr
                325

<210> SEQ ID NO 6
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Ser Ala Leu Lys Asn Val Ile Pro Gly Ala Leu Ala Leu Leu
1               5                   10                  15

Leu Leu Phe Pro Val Ala Ala Gln Ala Leu Pro Asn Ile Thr Ile Leu
                20                  25                  30

Ala Thr Gly Gly Thr Ile Ala Gly Gly Gly Asp Ser Ala Thr Lys Ser
            35                  40                  45

Asn Tyr Thr Ala Gly Lys Val Gly Val Glu Asn Leu Val Asn Ala Val
50                  55                  60

Pro Gln Leu Lys Asp Ile Ala Asn Val Lys Gly Glu Gln Val Val Asn
65                  70                  75                  80

Ile Gly Ser Gln Asp Met Asn Asp Asp Val Trp Leu Thr Leu Ala Lys

```
            85                  90                  95
Lys Ile Asn Thr Asp Cys Asp Lys Thr Asp Gly Phe Val Ile Thr His
                100                 105                 110
Gly Thr Asp Thr Met Glu Glu Thr Ala Tyr Phe Leu Asp Leu Thr Val
            115                 120                 125
Lys Cys Asp Lys Pro Val Val Met Val Gly Ala Met Arg Pro Ser Thr
        130                 135                 140
Ser Met Ser Ala Asp Gly Pro Phe Asn Leu Tyr Asn Ala Val Val Thr
145                 150                 155                 160
Ala Ala Asp Lys Ala Ser Ala Asn Arg Gly Val Leu Val Met Asn
                165                 170                 175
Asp Thr Val Leu Asp Gly Arg Asp Val Thr Lys Thr Asn Thr Thr Asp
                180                 185                 190
Val Ala Thr Phe Lys Ser Val Asn Tyr Gly Pro Leu Gly Tyr Ile His
            195                 200                 205
Asn Gly Lys Ile Asp Tyr Gln Arg Thr Pro Ala Arg Lys His Thr Ser
        210                 215                 220
Asp Thr Pro Phe Asp Val Ser Lys Leu Asn Glu Leu Pro Lys Val Gly
225                 230                 235                 240
Ile Val Tyr Asn Tyr Ala Asn Ala Ser Asp Leu Pro Ala Lys Ala Leu
                245                 250                 255
Val Asp Ala Gly Tyr Asp Gly Ile Val Ser Ala Gly Val Gly Asn Gly
            260                 265                 270
Asn Leu Tyr Lys Thr Val Phe Asp Thr Leu Ala Thr Ala Ala Lys Asn
        275                 280                 285
Gly Thr Ala Val Val Arg Ser Ser Arg Val Pro Thr Gly Ala Thr Thr
    290                 295                 300
Gln Asp Ala Glu Val Asp Asp Ala Lys Tyr Gly Phe Val Ala Ser Gly
305                 310                 315                 320
Thr Leu Asn Pro Gln Lys Ala Arg Val Leu Leu Gln Leu Ala Leu Thr
                325                 330                 335
Gln Thr Lys Asp Pro Gln Gln Ile Gln Gln Ile Phe Asn Gln Tyr
            340                 345                 350

<210> SEQ ID NO 7
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Gln Leu Phe Phe Cys Leu Met Leu Met Val Ser Leu Thr Ala
1               5                   10                  15
His Ala Leu Pro Asn Ile Thr Ile Leu Ala Thr Gly Gly Thr Ile Ala
                20                  25                  30
Gly Gly Gly Asp Ser Ala Thr Lys Ser Asn Tyr Thr Ala Gly Lys Val
            35                  40                  45
Gly Val Glu Asn Leu Val Asn Ala Val Pro Gln Leu Lys Asp Ile Ala
        50                  55                  60
Asn Val Lys Gly Glu Gln Val Val Asn Ile Gly Ser Gln Asp Met Asn
65                  70                  75                  80
Asp Asp Val Trp Leu Thr Leu Ala Lys Lys Ile Asn Thr Asp Cys Asp
                85                  90                  95
```

Lys Thr Asp Gly Phe Val Ile Thr His Gly Thr Asp Thr Met Glu Glu
            100                 105                 110

Thr Ala Tyr Phe Leu Asp Leu Thr Val Lys Cys Asp Lys Pro Val Val
        115                 120                 125

Met Val Gly Ala Met Arg Pro Ser Thr Ser Met Ser Ala Asp Gly Pro
    130                 135                 140

Phe Asn Leu Tyr Asn Ala Val Val Thr Ala Ala Asp Lys Ala Ser Ala
145                 150                 155                 160

Asn Arg Gly Val Leu Val Val Met Asn Asp Thr Val Leu Asp Gly Arg
                165                 170                 175

Asp Val Thr Lys Thr Asn Thr Thr Asp Val Ala Thr Phe Lys Ser Val
            180                 185                 190

Asn Tyr Gly Pro Leu Gly Tyr Ile His Asn Gly Lys Ile Asp Tyr Gln
        195                 200                 205

Arg Thr Pro Ala Arg Lys His Thr Ser Asp Thr Pro Phe Asp Val Ser
    210                 215                 220

Lys Leu Asn Glu Leu Pro Lys Val Gly Ile Val Tyr Asn Tyr Ala Asn
225                 230                 235                 240

Ala Ser Asp Leu Pro Ala Lys Ala Leu Val Asp Ala Gly Tyr Asp Gly
                245                 250                 255

Ile Val Ser Ala Gly Val Gly Asn Gly Asn Leu Tyr Lys Thr Val Phe
            260                 265                 270

Asp Thr Leu Ala Thr Ala Ala Lys Asn Gly Thr Ala Val Val Arg Ser
        275                 280                 285

Ser Arg Val Pro Thr Gly Ala Thr Thr Gln Asp Ala Glu Val Asp Asp
    290                 295                 300

Ala Lys Tyr Gly Phe Val Ala Ser Gly Thr Leu Asn Pro Gln Lys Ala
305                 310                 315                 320

Arg Val Leu Leu Gln Leu Ala Leu Thr Gln Thr Lys Asp Pro Gln Gln
                325                 330                 335

Ile Gln Gln Ile Phe Asn Gln Tyr
            340

<210> SEQ ID NO 8
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ile Arg Asp Asn Arg Leu Lys Thr Ser Leu Leu Arg Gly Leu Thr
1               5                   10                  15

Leu Thr Leu Leu Ser Leu Thr Leu Ser Pro Ala Ala His Ala Leu
            20                  25                  30

Pro Asn Ile Thr Ile Leu Ala Thr Gly Gly Thr Ile Ala Gly Gly Gly
        35                  40                  45

Asp Ser Ala Thr Lys Ser Asn Tyr Thr Ala Gly Lys Val Gly Val Glu
    50                  55                  60

Asn Leu Val Asn Ala Val Pro Gln Leu Lys Asp Ile Ala Asn Val Lys
65                  70                  75                  80

Gly Glu Gln Val Val Asn Ile Gly Ser Gln Asp Met Asn Asp Asp Val
                85                  90                  95

Trp Leu Thr Leu Ala Lys Lys Ile Asn Thr Asp Cys Asp Lys Thr Asp
            100                 105                 110

```
Gly Phe Val Ile Thr His Gly Thr Asp Thr Met Glu Glu Thr Ala Tyr
            115                 120                 125

Phe Leu Asp Leu Thr Val Lys Cys Asp Lys Pro Val Met Val Gly
130                 135                 140

Ala Met Arg Pro Ser Thr Ser Met Ser Ala Asp Gly Pro Phe Asn Leu
145                 150                 155                 160

Tyr Asn Ala Val Val Thr Ala Ala Asp Lys Ala Ser Ala Asn Arg Gly
            165                 170                 175

Val Leu Val Val Met Asn Asp Thr Val Leu Asp Gly Arg Asp Val Thr
            180                 185                 190

Lys Thr Asn Thr Thr Asp Val Ala Thr Phe Lys Ser Val Asn Tyr Gly
            195                 200                 205

Pro Leu Gly Tyr Ile His Asn Gly Lys Ile Asp Tyr Gln Arg Thr Pro
            210                 215                 220

Ala Arg Lys His Thr Ser Asp Thr Pro Phe Asp Val Ser Lys Leu Asn
225                 230                 235                 240

Glu Leu Pro Lys Val Gly Ile Val Tyr Asn Tyr Ala Asn Ala Ser Asp
            245                 250                 255

Leu Pro Ala Lys Ala Leu Val Asp Ala Gly Tyr Asp Gly Ile Val Ser
            260                 265                 270

Ala Gly Val Gly Asn Gly Asn Leu Tyr Lys Thr Val Phe Asp Thr Leu
            275                 280                 285

Ala Thr Ala Ala Lys Asn Gly Thr Ala Val Val Arg Ser Ser Arg Val
            290                 295                 300

Pro Thr Gly Ala Thr Thr Gln Asp Ala Glu Val Asp Asp Ala Lys Tyr
305                 310                 315                 320

Gly Phe Val Ala Ser Gly Thr Leu Asn Pro Gln Lys Ala Arg Val Leu
            325                 330                 335

Leu Gln Leu Ala Leu Thr Gln Thr Lys Asp Pro Gln Gln Ile Gln Gln
            340                 345                 350

Ile Phe Asn Gln Tyr
            355

<210> SEQ ID NO 9
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Leu Lys Arg Leu Met Ala Ala Met Thr Phe Val Ala Ala Gly
1               5                   10                  15

Val Ala Thr Ala Asn Ala Val Ala Leu Pro Asn Ile Thr Ile Leu Ala
            20                  25                  30

Thr Gly Gly Thr Ile Ala Gly Gly Asp Ser Ala Thr Lys Ser Asn
            35                  40                  45

Tyr Thr Ala Gly Lys Val Gly Val Glu Asn Leu Val Asn Ala Val Pro
50                  55                  60

Gln Leu Lys Asp Ile Ala Asn Val Lys Gly Glu Gln Val Val Asn Ile
65                  70                  75                  80

Gly Ser Gln Asp Met Asn Asp Asp Val Trp Leu Thr Leu Ala Lys Lys
            85                  90                  95

Ile Asn Thr Asp Cys Asp Lys Thr Asp Gly Phe Val Ile Thr His Gly
```

```
                    100                 105                 110
Thr Asp Thr Met Glu Glu Thr Ala Tyr Phe Leu Asp Leu Thr Val Lys
            115                 120                 125

Cys Asp Lys Pro Val Val Met Val Gly Ala Met Arg Pro Ser Thr Ser
130                 135                 140

Met Ser Ala Asp Gly Pro Phe Asn Leu Tyr Asn Ala Val Val Thr Ala
145                 150                 155                 160

Ala Asp Lys Ala Ser Ala Asn Arg Gly Val Leu Val Val Met Asn Asp
            165                 170                 175

Thr Val Leu Asp Gly Arg Asp Val Thr Lys Thr Asn Thr Thr Asp Val
            180                 185                 190

Ala Thr Phe Lys Ser Val Asn Tyr Gly Pro Leu Gly Tyr Ile His Asn
            195                 200                 205

Gly Lys Ile Asp Tyr Gln Arg Thr Pro Ala Arg Lys His Thr Ser Asp
            210                 215                 220

Thr Pro Phe Asp Val Ser Lys Leu Asn Glu Leu Pro Lys Val Gly Ile
225                 230                 235                 240

Val Tyr Asn Tyr Ala Asn Ala Ser Asp Leu Pro Ala Lys Ala Leu Val
                    245                 250                 255

Asp Ala Gly Tyr Asp Gly Ile Val Ser Ala Gly Val Gly Asn Gly Asn
                    260                 265                 270

Leu Tyr Lys Thr Val Phe Asp Thr Leu Ala Thr Ala Ala Lys Asn Gly
            275                 280                 285

Thr Ala Val Val Arg Ser Ser Arg Val Pro Thr Gly Ala Thr Thr Gln
            290                 295                 300

Asp Ala Glu Val Asp Asp Ala Lys Tyr Gly Phe Val Ala Ser Gly Thr
305                 310                 315                 320

Leu Asn Pro Gln Lys Ala Arg Val Leu Leu Gln Leu Ala Leu Thr Gln
                    325                 330                 335

Thr Lys Asp Pro Gln Gln Ile Gln Gln Ile Phe Asn Gln Tyr
            340                 345                 350

<210> SEQ ID NO 10
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gln Asn Tyr Lys Lys Phe Leu Leu Ala Ala Ala Val Ser Met Ala
1               5                   10                  15

Phe Ser Ala Thr Ala Met Ala Leu Pro Asn Ile Thr Ile Leu Ala Thr
                    20                  25                  30

Gly Gly Thr Ile Ala Gly Gly Gly Asp Ser Ala Thr Lys Ser Asn Tyr
            35                  40                  45

Thr Ala Gly Lys Val Gly Val Glu Asn Leu Val Asn Ala Val Pro Gln
50                  55                  60

Leu Lys Asp Ile Ala Asn Val Lys Gly Glu Gln Val Val Asn Ile Gly
65                  70                  75                  80

Ser Gln Asp Met Asn Asp Asp Val Trp Leu Thr Leu Ala Lys Lys Ile
                    85                  90                  95

Asn Thr Asp Cys Asp Lys Thr Asp Gly Phe Val Ile Thr His Gly Thr
                    100                 105                 110
```

```
Asp Thr Met Glu Glu Thr Ala Tyr Phe Leu Asp Leu Thr Val Lys Cys
            115                 120                 125

Asp Lys Pro Val Val Met Val Gly Ala Met Arg Pro Ser Thr Ser Met
        130                 135                 140

Ser Ala Asp Gly Pro Phe Asn Leu Tyr Asn Ala Val Val Thr Ala Ala
145                 150                 155                 160

Asp Lys Ala Ser Ala Asn Arg Gly Val Leu Val Met Asn Asp Thr
            165                 170                 175

Val Leu Asp Gly Arg Asp Val Thr Lys Thr Asn Thr Asp Val Ala
        180                 185                 190

Thr Phe Lys Ser Val Asn Tyr Gly Pro Leu Gly Tyr Ile His Asn Gly
            195                 200                 205

Lys Ile Asp Tyr Gln Arg Thr Pro Ala Arg Lys His Thr Ser Asp Thr
        210                 215                 220

Pro Phe Asp Val Ser Lys Leu Asn Glu Leu Pro Lys Val Gly Ile Val
225                 230                 235                 240

Tyr Asn Tyr Ala Asn Ala Ser Asp Leu Pro Ala Lys Ala Leu Val Asp
            245                 250                 255

Ala Gly Tyr Asp Gly Ile Val Ser Ala Gly Val Gly Asn Gly Asn Leu
        260                 265                 270

Tyr Lys Thr Val Phe Asp Thr Leu Ala Thr Ala Lys Asn Gly Thr
            275                 280                 285

Ala Val Val Arg Ser Ser Arg Val Pro Thr Gly Ala Thr Thr Gln Asp
        290                 295                 300

Ala Glu Val Asp Asp Ala Lys Tyr Gly Phe Val Ala Ser Gly Thr Leu
305                 310                 315                 320

Asn Pro Gln Lys Ala Arg Val Leu Leu Gln Leu Ala Leu Thr Gln Thr
            325                 330                 335

Lys Asp Pro Gln Gln Ile Gln Gln Ile Phe Asn Gln Tyr
        340                 345
```

<210> SEQ ID NO 11
<211> LENGTH: 346
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Phe Ala Lys Leu Val Ala Val Ser Leu Leu Thr Leu Ala Ser Gly
1               5                   10                  15

Gln Leu Leu Ala Leu Pro Asn Ile Thr Ile Leu Ala Thr Gly Gly Thr
            20                  25                  30

Ile Ala Gly Gly Gly Asp Ser Ala Thr Lys Ser Asn Tyr Thr Ala Gly
        35                  40                  45

Lys Val Gly Val Glu Asn Leu Val Asn Ala Val Pro Gln Leu Lys Asp
    50                  55                  60

Ile Ala Asn Val Lys Gly Glu Gln Val Val Asn Ile Gly Ser Gln Asp
65                  70                  75                  80

Met Asn Asp Asp Val Trp Leu Thr Leu Ala Lys Lys Ile Asn Thr Asp
                85                  90                  95

Cys Asp Lys Thr Asp Gly Phe Val Ile Thr His Gly Thr Asp Thr Met
            100                 105                 110

Glu Glu Thr Ala Tyr Phe Leu Asp Leu Thr Val Lys Cys Asp Lys Pro
        115                 120                 125
```

Val Val Met Val Gly Ala Met Arg Pro Ser Thr Ser Met Ser Ala Asp
            130                 135                 140

Gly Pro Phe Asn Leu Tyr Asn Ala Val Thr Ala Ala Asp Lys Ala
145                 150                 155                 160

Ser Ala Asn Arg Gly Val Leu Val Val Met Asn Asp Thr Val Leu Asp
                165                 170                 175

Gly Arg Asp Val Thr Lys Thr Asn Thr Thr Asp Val Ala Thr Phe Lys
                180                 185                 190

Ser Val Asn Tyr Gly Pro Leu Gly Tyr Ile His Asn Gly Lys Ile Asp
                195                 200                 205

Tyr Gln Arg Thr Pro Ala Arg Lys His Thr Ser Asp Thr Pro Phe Asp
            210                 215                 220

Val Ser Lys Leu Asn Glu Leu Pro Lys Val Gly Ile Val Tyr Asn Tyr
225                 230                 235                 240

Ala Asn Ala Ser Asp Leu Pro Ala Lys Ala Leu Val Asp Ala Gly Tyr
                245                 250                 255

Asp Gly Ile Val Ser Ala Gly Val Gly Asn Gly Asn Leu Tyr Lys Thr
                260                 265                 270

Val Phe Asp Thr Leu Ala Thr Ala Ala Lys Asn Gly Thr Ala Val Val
                275                 280                 285

Arg Ser Ser Arg Val Pro Thr Gly Ala Thr Thr Gln Asp Ala Glu Val
            290                 295                 300

Asp Asp Ala Lys Tyr Gly Phe Val Ala Ser Gly Thr Leu Asn Pro Gln
305                 310                 315                 320

Lys Ala Arg Val Leu Leu Gln Leu Ala Leu Thr Gln Thr Lys Asp Pro
                325                 330                 335

Gln Gln Ile Gln Gln Ile Phe Asn Gln Tyr
                340                 345

<210> SEQ ID NO 12
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Leu Lys Arg Leu Met Ala Ala Met Thr Phe Val Ala Ala Gly
1               5                   10                  15

Val Ala Thr Val Asn Ala Val Ala Leu Pro Asn Ile Thr Ile Leu Ala
                20                  25                  30

Thr Gly Gly Thr Ile Ala Gly Gly Asp Ser Ala Thr Lys Ser Asn
            35                  40                  45

Tyr Thr Ala Gly Lys Val Gly Val Glu Asn Leu Val Asn Ala Val Pro
50                  55                  60

Gln Leu Lys Asp Ile Ala Asn Val Lys Gly Glu Gln Val Val Asn Ile
65                  70                  75                  80

Gly Ser Gln Asp Met Asn Asp Asp Val Trp Leu Thr Leu Ala Lys Lys
                85                  90                  95

Ile Asn Thr Asp Cys Asp Lys Thr Asp Gly Phe Val Ile Thr His Gly
                100                 105                 110

Thr Asp Thr Met Glu Glu Thr Ala Tyr Phe Leu Asp Leu Thr Val Lys
            115                 120                 125

Cys Asp Lys Pro Val Val Met Val Gly Ala Met Arg Pro Ser Thr Ser

```
                130                 135                 140
Met Ser Ala Asp Gly Pro Phe Asn Leu Tyr Asn Ala Val Val Thr Ala
145                 150                 155                 160

Ala Asp Lys Ala Ser Ala Asn Arg Gly Val Leu Val Val Met Asn Asp
                165                 170                 175

Thr Val Leu Asp Gly Arg Asp Val Thr Lys Thr Asn Thr Thr Asp Val
                180                 185                 190

Ala Thr Phe Lys Ser Val Asn Tyr Gly Pro Leu Gly Tyr Ile His Asn
                195                 200                 205

Gly Lys Ile Asp Tyr Gln Arg Thr Pro Ala Arg Lys His Thr Ser Asp
                210                 215                 220

Thr Pro Phe Asp Val Ser Lys Leu Asn Glu Leu Pro Lys Val Gly Ile
225                 230                 235                 240

Val Tyr Asn Tyr Ala Asn Ala Ser Asp Leu Pro Ala Lys Ala Leu Val
                245                 250                 255

Asp Ala Gly Tyr Asp Gly Ile Val Ser Ala Gly Val Gly Asn Gly Asn
                260                 265                 270

Leu Tyr Lys Thr Val Phe Asp Thr Leu Ala Thr Ala Ala Lys Asn Gly
                275                 280                 285

Thr Ala Val Val Arg Ser Ser Arg Val Pro Thr Gly Ala Thr Thr Gln
                290                 295                 300

Asp Ala Glu Val Asp Asp Ala Lys Tyr Gly Phe Val Ala Ser Gly Thr
305                 310                 315                 320

Leu Asn Pro Gln Lys Ala Arg Val Leu Leu Gln Leu Ala Leu Thr Gln
                325                 330                 335

Thr Lys Asp Pro Gln Gln Ile Gln Gln Ile Phe Asn Gln Tyr
                340                 345                 350

<210> SEQ ID NO 13
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Pro Pro Arg Ser Ile Ala Ala Cys Leu Gly Leu Leu Gly Leu Leu
1               5                   10                  15

Met Ala Thr Gln Ala Ala Leu Pro Asn Ile Thr Ile Leu Ala Thr
                20                  25                  30

Gly Gly Thr Ile Ala Gly Gly Asp Ser Ala Thr Lys Ser Asn Tyr
            35                  40                  45

Thr Ala Gly Lys Val Gly Val Glu Asn Leu Val Asn Ala Val Pro Gln
    50                  55                  60

Leu Lys Asp Ile Ala Asn Val Lys Gly Glu Gln Val Val Asn Ile Gly
65                  70                  75                  80

Ser Gln Asp Met Asn Asp Asp Val Trp Leu Thr Leu Ala Lys Lys Ile
                85                  90                  95

Asn Thr Asp Cys Asp Lys Thr Asp Gly Phe Val Ile Thr His Gly Thr
                100                 105                 110

Asp Thr Met Glu Glu Thr Ala Tyr Phe Leu Asp Leu Thr Val Lys Cys
            115                 120                 125

Asp Lys Pro Val Val Met Val Gly Ala Met Arg Pro Ser Thr Ser Met
    130                 135                 140
```

Ser Ala Asp Gly Pro Phe Asn Leu Tyr Asn Ala Val Val Thr Ala Ala
145                 150                 155                 160

Asp Lys Ala Ser Ala Asn Arg Gly Val Leu Val Val Met Asn Asp Thr
            165                 170                 175

Val Leu Asp Gly Arg Asp Val Thr Lys Thr Asn Thr Thr Asp Val Ala
            180                 185                 190

Thr Phe Lys Ser Val Asn Tyr Gly Pro Leu Gly Tyr Ile His Asn Gly
        195                 200                 205

Lys Ile Asp Tyr Gln Arg Thr Pro Ala Arg Lys His Thr Ser Asp Thr
    210                 215                 220

Pro Phe Asp Val Ser Lys Leu Asn Glu Leu Pro Lys Val Gly Ile Val
225                 230                 235                 240

Tyr Asn Tyr Ala Asn Ala Ser Asp Leu Pro Ala Lys Ala Leu Val Asp
                245                 250                 255

Ala Gly Tyr Asp Gly Ile Val Ser Ala Gly Val Gly Asn Gly Asn Leu
            260                 265                 270

Tyr Lys Thr Val Phe Asp Thr Leu Ala Thr Ala Ala Lys Asn Gly Thr
        275                 280                 285

Ala Val Val Arg Ser Ser Arg Val Pro Thr Gly Ala Thr Thr Gln Asp
290                 295                 300

Ala Glu Val Asp Asp Ala Lys Tyr Gly Phe Val Ala Ser Gly Thr Leu
305                 310                 315                 320

Asn Pro Gln Lys Ala Arg Val Leu Leu Gln Leu Ala Leu Thr Gln Thr
                325                 330                 335

Lys Asp Pro Gln Gln Ile Gln Gln Ile Phe Asn Gln Tyr
            340                 345

<210> SEQ ID NO 14
<211> LENGTH: 25
<212> TYPE: PRT
<213> ORGANISM: Pseudomonas fluorescens

<400> SEQUENCE: 14

Met Lys Ser Ala Leu Lys Asn Val Ile Pro Gly Ala Leu Ala Leu Leu
1               5                   10                  15

Leu Leu Phe Pro Val Ala Ala Gln Ala
            20                  25

<210> SEQ ID NO 15
<211> LENGTH: 75
<212> TYPE: DNA
<213> ORGANISM: Pseudomonas fluorescens

<400> SEQUENCE: 15
atgaaatctg cattgaagaa cgttattccg ggcgccctgg cccttctgct gctattcccc      60
gtcgccgccc aggca                                                      75

<210> SEQ ID NO 16
<211> LENGTH: 18
<212> TYPE: PRT
<213> ORGANISM: Pseudomonas fluorescens

<400> SEQUENCE: 16

Met Arg Gln Leu Phe Phe Cys Leu Met Leu Met Val Ser Leu Thr Ala
1               5                   10                  15

His Ala

```
<210> SEQ ID NO 17
<211> LENGTH: 54
<212> TYPE: DNA
<213> ORGANISM: Pseudomonas fluorescens

<400> SEQUENCE: 17
atgcgacaac tattttctg tttgatgctg atggtgtcgc tcacggcgca cgcc         54

<210> SEQ ID NO 18
<211> LENGTH: 31
<212> TYPE: PRT
<213> ORGANISM: Pseudomonas fluorescens

<400> SEQUENCE: 18

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30

<210> SEQ ID NO 19
<211> LENGTH: 93
<212> TYPE: DNA
<213> ORGANISM: Pseudomonas fluorescens

<400> SEQUENCE: 19
atgatccgtg acaaccgact caagacatcc cttctgcgcg gcctgaccct cacctactc   60 agcctgaccc tgctctcgcc cgcggcccat gcc                               93

<210> SEQ ID NO 20
<211> LENGTH: 24
<212> TYPE: PRT
<213> ORGANISM: Pseudomonas fluorescens

<400> SEQUENCE: 20

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 21
<211> LENGTH: 72
<212> TYPE: DNA
<213> ORGANISM: Pseudomonas fluorescens

<400> SEQUENCE: 21
atgaaactga acgtttgat ggcggcaatg acttttgtcg ctgctggcgt tgcgaccgcc   60
aacgcggtgg cc                                                     72

<210> SEQ ID NO 22
<211> LENGTH: 23
<212> TYPE: PRT
<213> ORGANISM: Pseudomonas fluorescens

<400> SEQUENCE: 22

Met Gln Asn Tyr Lys Lys Phe Leu Leu Ala Ala Ala Val Ser Met Ala
1               5                   10                  15

Phe Ser Ala Thr Ala Met Ala
            20

<210> SEQ ID NO 23
<211> LENGTH: 69
<212> TYPE: DNA
```

<213> ORGANISM: Pseudomonas fluorescens

<400> SEQUENCE: 23

```
atgcagaact ataaaaaatt ccttctggcc gcggccgtct cgatggcgtt cagcgccacg    60
gccatggca                                                            69
```

<210> SEQ ID NO 24
<211> LENGTH: 20
<212> TYPE: PRT
<213> ORGANISM: Pseudomonas fluorescens

<400> SEQUENCE: 24

```
Met Phe Ala Lys Leu Val Ala Val Ser Leu Leu Thr Leu Ala Ser Gly
1               5                   10                  15

Gln Leu Leu Ala
            20
```

<210> SEQ ID NO 25
<211> LENGTH: 60
<212> TYPE: DNA
<213> ORGANISM: Pseudomonas fluorescens

<400> SEQUENCE: 25

```
atgtttgcca aactcgttgc tgtttccctg ctgactctgg cgagcggcca gttgcttgct    60
```

<210> SEQ ID NO 26
<211> LENGTH: 24
<212> TYPE: PRT
<213> ORGANISM: Pseudomonas fluorescens

<400> SEQUENCE: 26

```
Met Lys Leu Lys Arg Leu Met Ala Ala Met Thr Phe Val Ala Ala Gly
1               5                   10                  15

Val Ala Thr Val Asn Ala Val Ala
            20
```

<210> SEQ ID NO 27
<211> LENGTH: 72
<212> TYPE: DNA
<213> ORGANISM: Pseudomonas fluorescens

<400> SEQUENCE: 27

```
atgaaactga acgtttgat ggcggcaatg acttttgtcg ctgctggcgt tgcgaccgtc    60
aacgcggtgg cc                                                        72
```

<210> SEQ ID NO 28
<211> LENGTH: 23
<212> TYPE: PRT
<213> ORGANISM: Pseudomonas fluorescens

<400> SEQUENCE: 28

```
Met Pro Pro Arg Ser Ile Ala Ala Cys Leu Gly Leu Leu Gly Leu Leu
1               5                   10                  15

Met Ala Thr Gln Ala Ala Ala
            20
```

<210> SEQ ID NO 29
<211> LENGTH: 69
<212> TYPE: DNA
<213> ORGANISM: Pseudomonas fluorescens

<400> SEQUENCE: 29

```
atgccgcctc gttctatcgc cgcatgtctg gggctgctgg gcttgctcat ggctacccag    60
gccgccgcc                                                            69
```

<210> SEQ ID NO 30
<211> LENGTH: 22
<212> TYPE: PRT
<213> ORGANISM: Escherichia coli

<400> SEQUENCE: 30

```
Met Glu Phe Phe Lys Lys Thr Ala Leu Ala Ala Leu Val Met Gly Phe
1               5                   10                  15

Ser Gly Ala Ala Leu Ala
            20
```

<210> SEQ ID NO 31
<211> LENGTH: 33
<212> TYPE: PRT
<213> ORGANISM: Pseudomonas fluorescens

<400> SEQUENCE: 31

```
Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala
```

<210> SEQ ID NO 32
<211> LENGTH: 99
<212> TYPE: DNA
<213> ORGANISM: Pseudomonas fluorescens

<400> SEQUENCE: 32

```
atgcaaaacc gcactgtgga atcggtgtc ggccttttct tgctggctgg catcctggct    60
ttactgttgt tggccctgcg agtcagcggc ctttcggcc                          99
```

<210> SEQ ID NO 33
<211> LENGTH: 21
<212> TYPE: PRT
<213> ORGANISM: Pseudomonas fluorescens

<400> SEQUENCE: 33

```
Met Asn Arg Ser Ser Ala Leu Leu Leu Ala Phe Val Phe Leu Ser Gly
1               5                   10                  15

Cys Gln Ala Met Ala
            20
```

<210> SEQ ID NO 34
<211> LENGTH: 63
<212> TYPE: DNA
<213> ORGANISM: Pseudomonas fluorescens

<400> SEQUENCE: 34

```
atgaatagat cttccgcgtt gctcctcgct tttgtcttcc tcagcggctg ccaggccatg    60
gcc                                                                  63
```

<210> SEQ ID NO 35
<211> LENGTH: 21
<212> TYPE: PRT
<213> ORGANISM: Pseudomonas fluorescens

```
<400> SEQUENCE: 35

Met Arg Leu Thr Gln Ile Ile Ala Ala Ala Ile Ala Leu Val Ser
1               5                   10                  15

Thr Phe Ala Leu Ala
            20

<210> SEQ ID NO 36
<211> LENGTH: 63
<212> TYPE: DNA
<213> ORGANISM: Pseudomonas fluorescens

<400> SEQUENCE: 36
atgcgcttga cccagattat tgccgccgca gccattgcgt tggttttccac ctttgcgctc      60 gcc                                                                    63

<210> SEQ ID NO 37
<211> LENGTH: 29
<212> TYPE: PRT
<213> ORGANISM: Pseudomonas fluorescens

<400> SEQUENCE: 37

Met Gln Ser Leu Pro Phe Ser Ala Leu Arg Leu Leu Gly Val Leu Ala
1               5                   10                  15

Val Met Val Cys Val Leu Leu Thr Thr Pro Ala Arg Ala
            20                  25

<210> SEQ ID NO 38
<211> LENGTH: 87
<212> TYPE: DNA
<213> ORGANISM: Pseudomonas fluorescens

<400> SEQUENCE: 38
atgcaaagcc tgccgttctc tgcgttacgc ctgctcggtg tgctggcagt catggtctgc      60
gtgctgttga cgacgccagc ccgtgcc                                          87

<210> SEQ ID NO 39
<211> LENGTH: 22
<212> TYPE: PRT
<213> ORGANISM: Pseudomonas fluorescens

<400> SEQUENCE: 39

Met Arg Asn Leu Ile Leu Ser Ala Ala Leu Val Thr Ala Ser Leu Phe
1               5                   10                  15

Gly Met Thr Ala Gln Ala
            20

<210> SEQ ID NO 40
<211> LENGTH: 66
<212> TYPE: DNA
<213> ORGANISM: Pseudomonas fluorescens

<400> SEQUENCE: 40
atgcgtaatc tgatcctcag cgccgctctc gtcactgcca gcctcttcgg catgaccgca      60
caagct                                                                 66

<210> SEQ ID NO 41
<211> LENGTH: 21
<212> TYPE: PRT
<213> ORGANISM: Pseudomonas fluorescens

<400> SEQUENCE: 41
```

Met Arg Asn Leu Leu Arg Gly Met Leu Val Val Ile Cys Cys Met Ala
1               5                   10                  15

Gly Ile Ala Ala Ala
            20

<210> SEQ ID NO 42
<211> LENGTH: 63
<212> TYPE: DNA
<213> ORGANISM: Pseudomonas fluorescens

<400> SEQUENCE: 42
atgagaaacc ttcttcgagg aatgcttgtc gttatttgct gtatggcagg gatagcggcg    60
gcg                                                                  63

<210> SEQ ID NO 43
<211> LENGTH: 24
<212> TYPE: PRT
<213> ORGANISM: Pseudomonas fluorescens

<400> SEQUENCE: 43

Met Leu Phe Arg Thr Leu Leu Ala Ser Leu Thr Phe Ala Val Ile Ala
1               5                   10                  15

Gly Leu Pro Ser Thr Ala His Ala
            20

<210> SEQ ID NO 44
<211> LENGTH: 72
<212> TYPE: DNA
<213> ORGANISM: Pseudomonas fluorescens

<400> SEQUENCE: 44 atgcttttc gcacattact ggcgagcctt acctttgctg tcatcgccgg cttaccgtcc     60
acggcccacg cg                                                        72

<210> SEQ ID NO 45
<211> LENGTH: 6
<212> TYPE: DNA
<213> ORGANISM: Artificial Sequence
<220> FEATURE:
<223> OTHER INFORMATION: Description of Artificial Sequence: Synthetic
      consensus RBS sequence

<400> SEQUENCE: 45 aggagg                                                                6

<210> SEQ ID NO 46
<211> LENGTH: 6
<212> TYPE: DNA
<213> ORGANISM: Unknown
<220> FEATURE:
<223> OTHER INFORMATION: Description of Unknown:
      RBS2 sequence

<400> SEQUENCE: 46 ggagcg                                                                6

<210> SEQ ID NO 47
<211> LENGTH: 6
<212> TYPE: DNA
<213> ORGANISM: Unknown
<220> FEATURE:
<223> OTHER INFORMATION: Description of Unknown:
      RBS34 sequence

```
<400> SEQUENCE: 47 ggagcg                                                                    6

<210> SEQ ID NO 48
<211> LENGTH: 6
<212> TYPE: DNA
<213> ORGANISM: Unknown
<220> FEATURE:
<223> OTHER INFORMATION: Description of Unknown:
      RBS41 sequence

<400> SEQUENCE: 48 aggagt                                                                    6

<210> SEQ ID NO 49
<211> LENGTH: 6
<212> TYPE: DNA
<213> ORGANISM: Unknown
<220> FEATURE:
<223> OTHER INFORMATION: Description of Unknown:
      RBS43 sequence

<400> SEQUENCE: 49 ggagtg                                                                    6

<210> SEQ ID NO 50
<211> LENGTH: 6
<212> TYPE: DNA
<213> ORGANISM: Unknown
<220> FEATURE:
<223> OTHER INFORMATION: Description of Unknown:
      RBS48 sequence

<400> SEQUENCE: 50 gagtaa                                                                    6

<210> SEQ ID NO 51
<211> LENGTH: 6
<212> TYPE: DNA
<213> ORGANISM: Unknown
<220> FEATURE:
<223> OTHER INFORMATION: Description of Unknown:
      RBS1 sequence

<400> SEQUENCE: 51 agagag                                                                    6

<210> SEQ ID NO 52
<211> LENGTH: 6
<212> TYPE: DNA
<213> ORGANISM: Unknown
<220> FEATURE:
<223> OTHER INFORMATION: Description of Unknown:
      RBS35 sequence

<400> SEQUENCE: 52 aaggca                                                                    6

<210> SEQ ID NO 53
<211> LENGTH: 6
<212> TYPE: DNA
<213> ORGANISM: Unknown
<220> FEATURE:
<223> OTHER INFORMATION: Description of Unknown:
      RBS49 sequence
```

<400> SEQUENCE: 53 ccgaac                                                                    6

<210> SEQ ID NO 54
<211> LENGTH: 325
<212> TYPE: PRT
<213> ORGANISM: Pseudomonas fluorescens

<400> SEQUENCE: 54

```
Met Gln Ser Ala Asn Asn Val Met Val Leu Tyr Thr Gly Gly Thr Ile
1               5                   10                  15

Gly Met Gln Ala Ser Ala Asn Gly Leu Ala Pro Ala Ser Gly Phe Glu
            20                  25                  30

Val Arg Met Arg Glu Gln Phe Ala Gly Ala Asp Leu Pro Ala Trp Arg
        35                  40                  45

Phe Gln Glu Met Ser Pro Leu Ile Asp Ser Ala Asn Met Asn Pro Ala
    50                  55                  60

Tyr Trp Gln Arg Leu Arg Ser Ala Val Glu Ala Val Asp Ala Gly
65                  70                  75                  80

Cys Asp Ala Val Leu Ile Leu His Gly Thr Asp Thr Leu Ala Tyr Ser
                85                  90                  95

Ala Ala Ala Met Ser Phe Gln Leu Leu Gly Leu Pro Ala Pro Val Val
            100                 105                 110

Phe Thr Gly Ser Met Leu Pro Ala Gly Val Pro Asp Ser Asp Ala Trp
        115                 120                 125

Glu Asn Val Ser Gly Ala Leu Thr Ala Leu Gly Glu Gly Leu Lys Pro
    130                 135                 140

Gly Val His Leu Tyr Phe His Gly Ala Leu Met Ala Pro Thr Arg Cys
145                 150                 155                 160

Ala Lys Ile Arg Ser Phe Gly Arg Asn Pro Phe Ala Ala Leu Gln Arg
                165                 170                 175

Asn Gly Gly Val Ala Leu Ala Asp Lys Leu Pro Ala Ala Leu Ala Tyr
            180                 185                 190

Arg Asn Asp Lys Ala Pro Ala Asn Val Gly Val Leu Pro Leu Val Pro
        195                 200                 205

Gly Ile Ala Ala Ala Gln Leu Asp Ala Leu Ile Asp Ser Gly Ile Gln
    210                 215                 220

Ala Leu Val Leu Glu Cys Phe Gly Ser Gly Thr Gly Pro Ser Asp Asn
225                 230                 235                 240

Pro Ala Phe Leu Ala Ser Leu Lys Arg Ala Gln Asp Gln Glu Val Val
                245                 250                 255

Val Val Ala Ile Thr Gln Cys His Glu Gly Val Glu Leu Asp Val
            260                 265                 270

Tyr Glu Ala Gly Ser Arg Leu Arg Ser Val Gly Val Leu Ser Gly Gly
        275                 280                 285

Gly Met Thr Arg Glu Ala Ala Phe Gly Lys Leu Asn Ala Leu Ile Gly
    290                 295                 300

Ala Gly Leu Asp Ser Ala Glu Ile Arg Arg Leu Val Glu Leu Asp Leu
305                 310                 315                 320

Cys Gly Glu Leu Ser
                325
```

<210> SEQ ID NO 55
<211> LENGTH: 362
<212> TYPE: PRT

<213> ORGANISM: Pseudomonas fluorescens

<400> SEQUENCE: 55

Met Lys Ser Ala Leu Lys Asn Val Ile Pro Gly Ala Leu Ala Leu Leu
1               5                   10                  15

Leu Leu Phe Pro Val Ala Ala Gln Ala Lys Glu Val Gly Ser Lys Thr
            20                  25                  30

Lys Leu Ser Asn Val Val Ile Leu Ala Thr Gly Gly Thr Ile Ala Gly
        35                  40                  45

Ala Gly Ala Ser Ala Ala Asn Ser Ala Thr Tyr Gln Ala Ala Lys Val
    50                  55                  60

Gly Ile Glu Gln Leu Ile Ala Gly Val Pro Glu Leu Ser Gln Ile Ala
65                  70                  75                  80

Asn Val Arg Gly Glu Gln Val Met Gln Ile Ala Ser Glu Ser Ile Asn
                85                  90                  95

Asn Glu Asn Leu Leu Gln Leu Gly Arg Arg Val Ala Glu Leu Ala Asp
            100                 105                 110

Asn Lys Asp Val Asp Gly Ile Val Ile Thr His Gly Thr Asp Thr Leu
        115                 120                 125

Glu Glu Thr Ala Tyr Phe Leu Asn Leu Val Lys Thr Asp Lys Pro
130                 135                 140

Ile Val Val Val Gly Ser Met Arg Pro Gly Thr Ala Met Ser Ala Asp
145                 150                 155                 160

Gly Met Leu Asn Leu Tyr Asn Ala Val Ala Val Ala Gly Ser Lys Glu
                165                 170                 175

Ala Arg Gly Lys Gly Val Leu Val Thr Met Asn Asp Glu Ile Gln Ser
            180                 185                 190

Gly Arg Asp Val Ser Lys Met Ile Asn Ile Lys Thr Glu Ala Phe Lys
        195                 200                 205

Ser Pro Trp Gly Pro Met Gly Met Val Val Glu Gly Lys Ser Tyr Trp
210                 215                 220

Phe Arg Leu Pro Ala Lys Arg His Thr Met Asp Ser Glu Phe Asp Ile
225                 230                 235                 240

Lys Thr Ile Lys Ser Leu Pro Asp Val Glu Ile Ala Tyr Gly Tyr Gly
                245                 250                 255

Asn Val Ser Asp Thr Ala Tyr Lys Ala Leu Ala Gln Ala Gly Ala Lys
            260                 265                 270

Ala Ile Ile His Ala Gly Thr Gly Asn Gly Ser Val Ser Ser Lys Val
        275                 280                 285

Val Pro Ala Leu Val Glu Leu Arg Lys Gln Gly Val Gln Ile Ile Arg
290                 295                 300

Ser Ser His Val Asn Ala Gly Gly Met Val Leu Arg Asn Ala Glu Gln
305                 310                 315                 320

Pro Asp Asp Lys Tyr Asp Trp Val Ala Ala Leu Asp Leu Asn Pro Gln
                325                 330                 335

Lys Ala Arg Ile Leu Ala Met Val Ala Leu Thr Lys Thr Gln Asp Ser
            340                 345                 350

Lys Glu Leu Gln Arg Ile Phe Trp Glu Tyr
        355                 360

<210> SEQ ID NO 56
<211> LENGTH: 167
<212> TYPE: PRT
<213> ORGANISM: Pseudomonas fluorescens

```
<400> SEQUENCE: 56

Val Arg Lys Leu Thr Gln Leu Val Leu Leu Ala Thr Val Leu Val Thr
1               5                   10                  15

Thr Pro Ala Phe Ala Glu Met Lys Ile Ala Val Leu Asn Tyr Gln Met
                20                  25                  30

Ala Leu Leu Glu Ser Asp Ala Ala Lys Arg Tyr Ala Val Asp Ala Glu
                35                  40                  45

Lys Lys Phe Gly Pro Gln Leu Thr Lys Leu Lys Thr Leu Glu Ser Ser
        50                  55                  60

Ala Lys Gly Ile Gln Asp Arg Leu Val Ala Gly Gly Asp Lys Met Gln
65                  70                  75                  80

Gln Gly Glu Arg Glu Arg Leu Glu Leu Glu Phe Lys Gln Lys Ala Arg
                85                  90                  95

Asp Tyr Gln Phe Gln Ser Lys Glu Leu Asn Glu Ala Lys Ala Val Ala
                100                 105                 110

Asp Arg Glu Met Leu Lys Gln Leu Lys Pro Lys Leu Asp Ser Ala Val
            115                 120                 125

Glu Glu Val Ile Lys Lys Gly Ala Phe Asp Leu Val Phe Glu Arg Gly
        130                 135                 140

Ala Val Ile Asp Val Lys Pro Gln Tyr Asp Ile Thr Arg Gln Val Ile
145                 150                 155                 160

Glu Arg Met Asn Gln Leu Lys
                165

<210> SEQ ID NO 57
<211> LENGTH: 504
<212> TYPE: DNA
<213> ORGANISM: Pseudomonas fluorescens

<400> SEQUENCE: 57
gtgcgtaagt tgactcaatt ggtcttgctg gccactgtgc tggtcaccac cccggccttc      60
gccgaaatga aaatcgccgt tctgaactat cagatggccc tgctggaatc cgatgcggcc     120
aagcgatacg ccgtggatgc cgagaagaag ttcggtccgc aactgaccaa gctcaagaca     180
ctggaaagca gcgccaaagg catccaggac cgcctggtag ccggtggcga caagatgcag     240
caaggcgagc gcgagcgtct ggagcttgaa ttcaagcaaa aggcccgtga ctaccagttc     300
caatccaagg agctgaacga agccaaggct gtggccgacc gcgaaatgct caagcagctc     360
aagcctaaat tggacagcgc tgtggaagaa gtcatcaaga agggtgcctt tgacctggtg     420
ttcgagcgtg gcgccgtgat cgacgtcaag cctcaatacg acatcacccg ccaggtgatc     480
gagcgcatga accagctgaa gtga                                            504
```